US007232684B2

(12) United States Patent
DeAngelis

(10) Patent No.: US 7,232,684 B2
(45) Date of Patent: Jun. 19, 2007

(54) **DNA ENCODING HYALURONAN SYNTHASE FROM *PASTEURELLA MULTOCIDA* AND METHODS OF USE**

(75) Inventor: Paul DeAngelis, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 11/124,215

(22) Filed: May 9, 2005

(65) Prior Publication Data

US 2005/0266460 A1 Dec. 1, 2005

Related U.S. Application Data

(63) Continuation of application No. 10/217,613, filed on Aug. 12, 2002, now Pat. No. 6,987,023, which is a continuation of application No. 09/283,402, filed on Apr. 1, 1999, now abandoned, which is a continuation-in-part of application No. 09/178,851, filed on Oct. 26, 1998, now abandoned.

(60) Provisional application No. 60/080,414, filed on Apr. 2, 1998.

(51) Int. Cl.
*C12N 5/10* (2006.01)
*C12N 1/21* (2006.01)
*C12N 15/63* (2006.01)
*C12N 9/10* (2006.01)
*C07H 21/04* (2006.01)

(52) U.S. Cl. .............. 435/325; 435/252.3; 435/254.11; 435/320.1; 435/193; 536/23.2

(58) Field of Classification Search ..................... None
See application file for complete search history.

(56) References Cited

U.S. PATENT DOCUMENTS

| | | | |
|---|---|---|---|
| 4,169,886 | A | 10/1979 | Hertman et al. |
| 4,224,179 | A | 9/1980 | Schneider |
| 4,235,871 | A | 11/1980 | Papahadjopoulos et al. |
| 4,511,478 | A | 4/1985 | Nowinski et al. |
| 4,517,295 | A | 5/1985 | Bracke et al. |
| 4,708,861 | A | 11/1987 | Popescu et al. |
| 4,780,414 | A | 10/1988 | Nimrod et al. |
| 4,782,046 | A | 11/1988 | Brown et al. |
| 4,784,990 | A | 11/1988 | Nimrod et al. |
| 4,801,539 | A | 1/1989 | Akasaka et al. |
| 4,885,244 | A | 12/1989 | Miyamori et al. |
| 5,015,577 | A | 5/1991 | Weigel et al. |
| 5,023,175 | A | 6/1991 | Hosoya et al. |
| 5,071,751 | A | 12/1991 | Morita et al. |
| RE37,336 | E | 8/2001 | Weigel et al. |
| 6,423,514 | B1 | 7/2002 | Briskin |

FOREIGN PATENT DOCUMENTS

| | | |
|---|---|---|
| EP | 0036776 | 5/1988 |
| EP | 0195303 | 11/1989 |
| EP | 0144019 | 6/1990 |
| EP | 0266578 | 7/1993 |
| EP | 0244757 | 11/1994 |
| GB | 2249315 | 5/1992 |
| JP | 4-158796 | 0/1992 |
| JP | 62032893 | 0/1987 |
| JP | 63094988 | 0/1988 |
| JP | 4-80202 | 3/1992 |
| WO | 91/03559 WO | 3/1991 |
| WO | 94/00463 WO | 1/1994 |
| WO | 95/24497 WO | 9/1995 |
| WO | 95/33067 WO | 12/1995 |
| WO | 97/20061 WO | 6/1997 |

OTHER PUBLICATIONS

"The Production of Capsules, Hyaluronic Acid and Hyaluronidase by Group A and Group C *Streptococci*", MacLennan, J. Gen. Microbiol., 14:134-142 (1956).
"The Isolation and Characterization of a Hyaluronidase Produced by a Capsulated Strain of Group C *Streptococcus*", MacLennan, J. Gen. Microbiol., 14:143-152 (1956).
"The Biosynthesis of Hyaluronic Acid by Group A *Streptococcus*", Markovitz et al., J. Biol. Chem., 234 (9):2343-2350 (1959).
"The Biosynthesis of Hyaluronic Acid by *Streptococcus*," Stoolmiller, et al., Journal of Biological Chemistry, vol. 244, No. 2, pp. 236-246 (1969).
"The Isolation and Characterization of Hyaluronic Acid From *Pasteurella multocida*", Cifonelli, et al., Carbohydrate Research, 14, 272-276, (1970).
"Biosynthesis of Hyaluronic Acid by *Streptococcus*", Sugahara et al., J. Biol. Chem., 254:6252-6261 (1979).
"Modern Genetics," Ayala, et al., Benjamin/Cummings Publishing Col., Menlo Park CA, p. 45 (1980).
"Hyaluronidase Production by Type B *Pasteurella multocida* From Cases of *Hemorrhagic septicemia*", Carter, et al., Journal of Clinical Microbiology, p. 94-96, (1980).
"Strains of *Escherichia coli* Carrying the Structural Gene for Histidyl-tRNA Synthetase on a High Copy-Number Plasmid," Eisenbeis, et al., Mol. Gen. Genet. 183:115-122 (1981).
"Synthesis of Hyaluronate in Differentiated Teratocarcinoma Cells," Prehm, et al., J. Biochem, vol. 211, pp. 181-189 (1983).
"Streptococcal Hyaluronic Acid: Proposed Mechanisms of Degradation and Loss of Synthesis During Stationary Phase", Van de Rijn, J. Bacteriol., 156(3):1059-1065 (1983).
"Solubilization of Hyaluronic Acid Synthetic Activity From *Streptococci* and its Activation With Phospholipids", Triscott et al., J. Biol. Chem., 261(13):6004-6009 (1986).
"Isolation of Streptococcal Hyaluronate Synthase", Prehm et al., Biochem. J., 235:887-889 (1986).

(Continued)

*Primary Examiner*—Robert A. Wax
(74) *Attorney, Agent, or Firm*—Dunlap, Codding & Rogers, P.C.

(57) ABSTRACT

The present invention relates to a nucleic acid segment having a coding region segment encoding enzymatically active *Pasteurella multocida* hyaluronate synthase (PmHAS), and to the use of this nucleic acid segment in the preparation of recombinant cells which produce hyaluronate synthase and its hyaluronic acid product.

20 Claims, 17 Drawing Sheets

OTHER PUBLICATIONS

"Isolation, Structure and Expression of Mammalian Genes for Histidyl-tRNA Synthetase," Tsui, et al., Nucleic Acids Research, vol. 15, No. 8, pp. 3349-3367, (1987).

"Shuttle Vectors Containing a Multiple Cloning Site and a Lacza Gena for Conjugal Transfer of DNA From *Escherichia coli* to Gram-Positive Bacteria," Trieu-Cout, et al., Gene, vol. 102, pp. 99-104, (1991).

"Analysis of the Streptococcal Hyaluronic Acid Synthase Complex Using the Photoaffinity Probe 5-Azido-UDP-Glucuronic Acid," Van de Rijn, et al., J. Biol., Chem., vol. 267, No. 34, pp. 24302-24306, (1992).

"Molecular Characterization of a Locus Required for Hyaluronic Acid Capsule Production in Group A *Streptococci*," Dougherty, et al., J. Exp. Med., vol. 175, pp. 1291-1299, (1992).

"Hyaluronan," Laurent, et al., FASEB Journal, vol. 6, pp. 2397-2404, (1992).

"Hyaluronic Acid and a (1-4)-B-D-Xylan, Extracellular Polysaccharides of *Pasteurella multocida* (Carter Type A) Strain 880", Rosner, et al., Carbohydrate Research, 223, 329-333 (1992).

"Isolation of a Streptococcus Pyogenes Gene Locus That Directs Hyaluronan Biosynthesis in Acapsular Mutants and in Heterologous Bacteria," DeAngelis, et al., J. Biol. Chem., vol. 268, No. 20, pp. 14568-14571, (1993).

"Hyaluronate Synthase: Cloning and Sequencing of the Gene From *Streptococcus* sp.," Lansing, et al., J. Biochem., vol. 289, pp. 179-184, (1993).

"Molecular Characterization of HASB From an Operon Required for Hyaluronic Acid Synthesis in Group A *Streptococci*," Dougherty, et al., J. Biol. Chem., vol. 268, No. 10, pp. 7118-7124, (1993).

"Molecular Cloning, Identification, and Sequence of the Hyaluronan Synthase Gene From Group A *Streptococcus pyogenes*," DeAngelis, et al., J. Biol. Chem., vol. 268, No. 26, pp. 19181-19184, (1993).

"Capsular Hyaluronic Acid in *Pasteurella multocida* Type A and its Counterpart in Type D", Pandit, Research in Veterinary Science 54, 20-24 (1993).

"Molecular Characterization of HASA From an Operon Required for Hyaluronic Acid Synthesis in Group A *Streptococci*," Dougherty, et al., J. Biol. Chem., vol. 269, No. 1, pp. 169-175.

"The *Streptococcus pyogenes* Hyaluronan Sytnhase: Sequence Comparison and Conservation Among Various Group A Strains," DeAngelis, et al., Biochem. and Biophy. Res. Comm., vol. 199, No. 1, pp. 1-10, (1994).

"Hyaluronidase and Chondroitinase Activity of *Pasteurella multocida* Serotype B:2 Involved in *Haemorrhagic septicaemia*", Rimler, et al., Veterinary Record 134, 67-68 (1994).

"Molecular Fingerprinting of *Pasteurella multocida* Associated With Progressive Atrophic Rhinitis in Swine Herds". Gardner et al. Database Medline on Diaolog, US Nat'l. Library of Medicine (Bethesda, MD, USA) No. 95161494, Abstract, J. Vet. Diagn. Invest. Oct. 1994. vol. 6, No. 4 pages.

The Elucidation of Novel Capsular Genotypes of *Haemophilus influenzae* Type B With the Polymerase Chain Reaction. Leaves et al. J. Medical Microbiology, 1995, vol. 43, pp. 120-124, entire document.

"Capsular Hyaluronic Acid-Mediated Adhesion of *Pasteurella multocida* to Turkey Air SAC Macrophages", Pruimboom, et al., Avian Diseases 40:887-893, (1996).

"Homologs of the *Xenopus* Developmental Gene DG42 are Present in Zebrafish and Mouse and are Involved in the Synthesis of Nod-Like Chitin Oligosaccharides During Early Embryogenesis", Semino et al., Proc. Natl Acad. Sci. USA, 93:4548-4553 (1996).

"Enzymological Characterization of the *Pasteurella multocida* Hyaluronic Acid Synthase", DeAngelis, Biochemistry, 35 (30): 9768-9771 (1996).

"Construction and Characterization of a Potential Live Oral Carrier-Based Vaccine Against *Vibrio chlolerae*". Favre et al. Infection and Immunity. Sep. 1996, vol. 64, No. 9 pagres 3565-3570, entire document.

"Molecular Cloning, Expression, and Characterization of the Authentic Hyaluronan Synthase From Group C *Streptococcus equisimilis*", Kumari and Weigel, J. Biol. Chem., 272(51): 32539-32546 (1997).

"Hyaluronan Synthases", Weigel et al., J. Biol. Chem., 272 (22): 13997-14000 (1997).

"Identification and Molecular Cloning of a Unique Hyaluronan Synthase From *Pasterrella multocida*", DeAngelis et al., J. Biol. Chem., 273(14): 8454-8458 (1998).

"The Capsule Biosynthetic Locus of *Pasteurella multocida* A:1", Chung, et al. FEMS Microbiol. Lett. Sep. 15, 1998, vol. 166, No. 2, pp. 289-296, entire document.

"Transposon Tn916 Insertional Mutagenesis of *Pasteurella multocida* and Direct Sequencing of Disruption Site", Paul L. DeAngelis, Microbial Pathogenesis, 24: 203-209 (1998).

```
                                                                          (SEQ ID NO:)
PmHAS      INRVPLVSIYIPAYNC.ANYIQRCVDSALNQTVVDLEVCICNDGSTDNTL              8
EpsI       MYLKSLISIVIPVYNV.EKYLEKCLQSVQNQTYNNFEVILVNDGSTDSSL              9
Cps14E     ..MEDLVSIVVPVYNV.EKYLKKSIESILNQTYDNLEVLLVDDGSTDSSG              10
LgtD       .MNMPLISIIMPVYNA.ECYLNQGILSCLNQSYQNIELILIDDGSTDKSI              11
SpHasA     .PHDYKVAAVIPSYNEDAESLLETLKSVLAQTYPLSEIYIVDDGSSNTDA              12
Consensus  .....l!si.iP.YN......yl......S.LnQty....E....#DGSt#...

PmHAS      .....EVINKLYGNNPRVRIM.SKPNGGIASASNAAVSFAKGYYIGQLDSDDYLEPDA
EpsI       .....SICEKFVNQDKRFSVF.SKENGGMSSARNFGIKKAKGSFITFVDSDDYIVKDY
Cps14E     .....EICDSFIKVDSRIRVF.HKENGGLSDARNFGIEHMKGQYVSFIDGDDYISKDY
LgtD       .....EIINNIIDKDKRVKLFFTPTNQGPAAARNIGLEKAQGDYITFLDSDDFIANDK
SpHasA     IQLIEEYVNREVDICRNVIVHRSLVNKGKRHAQAWAFERSDADVFLTVDSDTYIYPNA
Consensus  ......E.........r!.....s..N.G...A.n....e...g......DSDd%i..#.

Fig. 1

(SEQ ID NO:)
PmHAS              FAAGNVAFAFAKKWLNKSGFFDEEFNHWGGEDVEFGYRL                 14
U-GalNAc:polypep   FAGGLFSISKKYFEHIGSYDEEMEIWGGENIEMSFRV                   15
Consensus          FA.G.....KK..#..G.%DEE.#.WGGE#!E..%R.                   16

Fig. 2
```

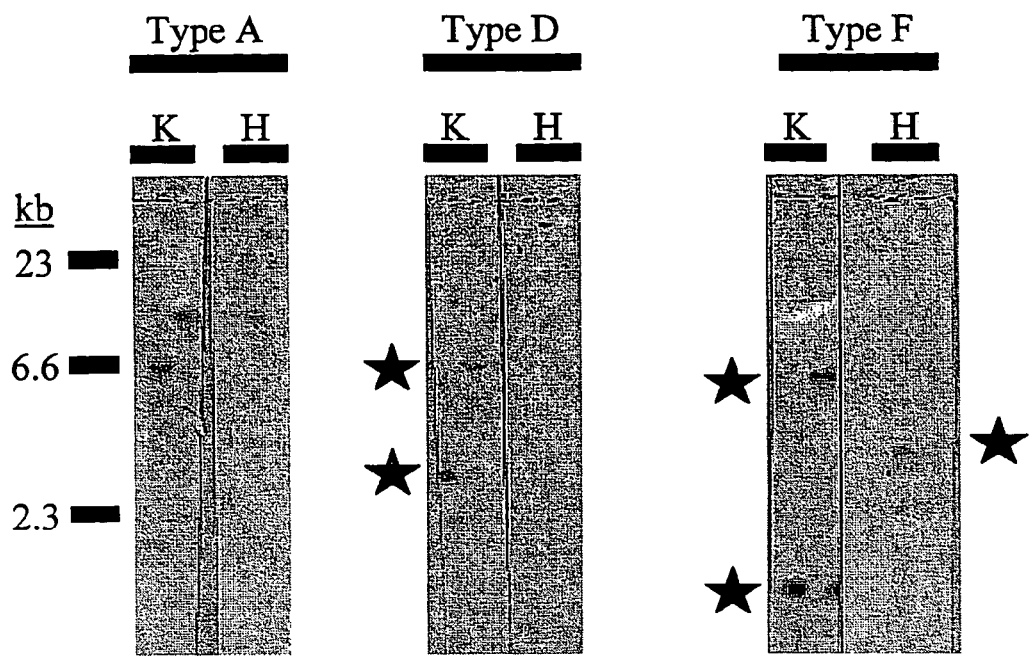
Fig. 15
A. KfaA analog primers
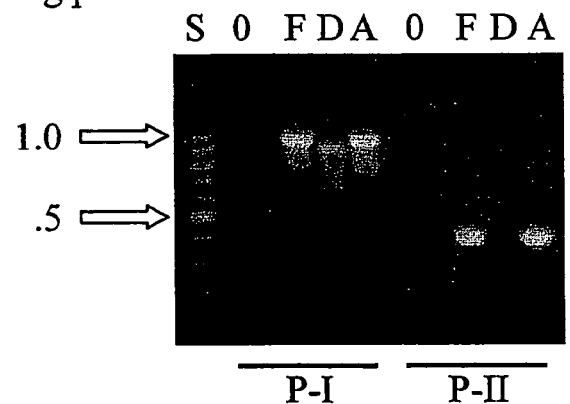
B. HA synthase primers
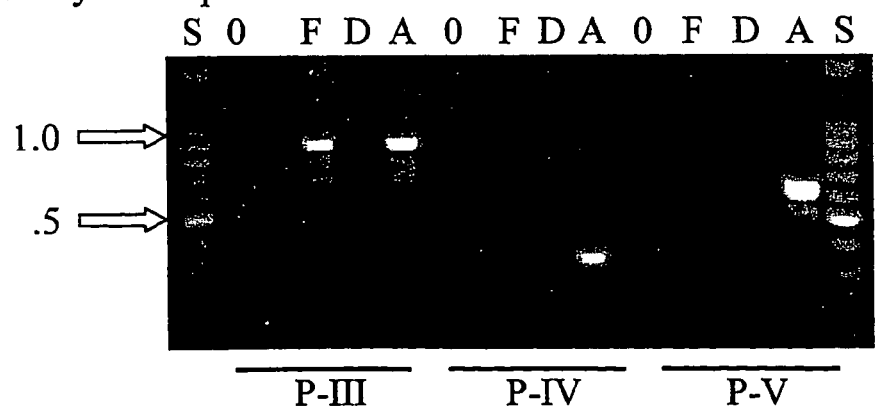
Fig. 16

| | | (SEQ ID NO:) |
|---|---|---|
| Type F | YIDNQVLKAK..PRLYGARDRIKNQLTYRLGYKIQRHEKSIWSHFSS | 4 |
| Type A | YIDNQVLKAK..PRLYGAADRIKNQLTYRLGYKIQRHGRSLFGLIFL | 5 |
| E.coli | FIENQEIKKKLPPVLYGAAEQIKQELGYRLGYIIVSYSKSLKGIITM | 6 |

A. Southern Blot Analysis      B. PCR Analysis
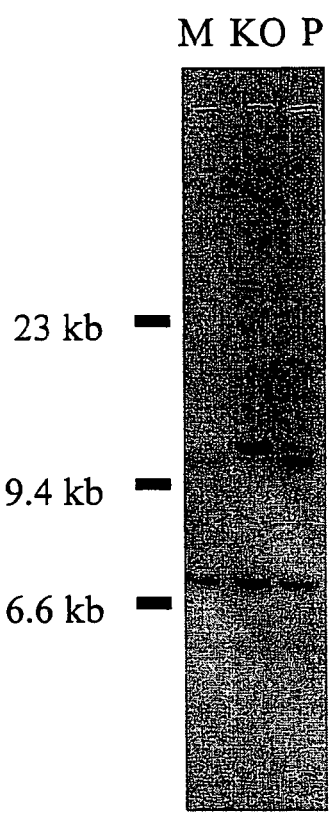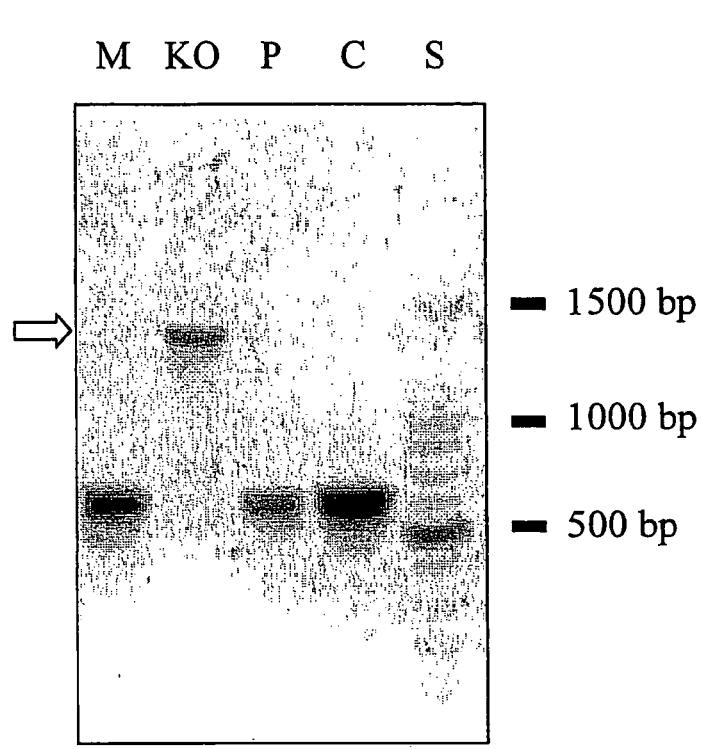
Fig. 19

```
             1                                                    50
PmHAS        MNTLSQAIKA  YNSNDYQLAL  KLFEKSAEIY  GRKIVEFQIT  KCQEKLSAHP
PmCS         MNTLSQAIKA  YNCNDYELAL  KLFEKSAETY  GRKIVEFQII  KCKEKLSTNS
Consensus    MNTLSQAIKA  YNcNDY#LAL  KLFEKSAEiY  GRKIVEFQIi  KCqEKLSanp 51                                                   100
PmHAS        SVNSAHLSVN  KEEKVNVCDS  PLDIATQLLL  SNVKKLVLSD  SEKNTLKNKW
PmCS         YVSEDNSYVS  EDKKNSVCDS  SLDIATQLLI  SNVKKLTLSE  SEKNSLKNKW
Consensus    sVneanlsVn  e#eKnnVCDS  pLDIATQLLi  SNVKKLtLS#  SEKNsLKNKW 101                                                  150
PmHAS        KLLTEKKSEN  AEVRAVALVP  KDFPKDLVLA  PLPDHVNDFT  WYKKRKKRLG
PmCS         KSITGKKSEN  AEIRKVELVP  KDFPKDLVLA  PLPDHVNDFT  WYKNRKKRLG
Consensus    KliTeKKSEN  AE!RaVaLVP  KDFPKDLVLA  PLPDHVNDFT  WYKnRKKRLG 151                                                  200
PmHAS        IKPEHQHVGL  SIIVTTFNRP  AILSITLACL  VNQKTHYPFE  VIVTDDGSQE
PmCS         IKPVNKNIGL  SIIIPTFNRS  RILDITLACL  VNQKTNYPFE  VVVADDGSKE
Consensus    IKPenqn!GL  SII!pTFNRp  aILDITLACL  VNQKTnYPFE  V!VaDDGSqE
```

Fig. 20A

```
            201                                                        250
PmHAS       DLSPIIRQYE  NKLDIRYVRQ  KDNGFQASAA  RNMGLRLAKY  DFIGLLDCDM
PmCS        NLLTIVQKYE  QKLDIKYVRQ  KDYGYQLCAV  RNLGLRTAKY  DFVSILDCDM
Consensus   #LlpI!rqYE  #KLDIrYVRQ  KDnG%QaCAa  RNsGLRlAKY  DF!gilDCDM 251                                                        300
PmHAS       APNPLWVHSY  VAELLEDDDL  TIIGPRKYID  TQHIDPKDFL  NNASLLESLP
PmCS        APQQLWVHSY  LTELLEDIDI  VLIGPRKYVD  THNITAEQFL  NDPYLIESLP
Consensus   AP#qLWVHSY  laElLEDdDi  tiiGPRKY!D  TqnIdae#FL  N#asLiESLP 301                                                        350
PmHAS       EVKTNNSVAA  KGEGTVSLDW  RLEQFEKTEN  LRLSDSPFRF  FAAGNVAFAK
PmCS        ETATNNNPSI  TSKGNISLDW  RLEHFKKTDN  LRLCDSPFRY  FVAGNVAFSK
Consensus   EtaTNNNpaa  kgeGn!SLDW  RLEqFeKT#N  LRLCDSPFR%  FaAGNVAFaK 351                                                        400
PmHAS       KWLNKSGFFD  EEFNHWGGED  VEFGYRLFRY  GSFFKTIDGI  MAYHQEPPGK
PmCS        EWLNKVGWFD  EEFNHWGGED  VEFGYRLFPK  GCFFRVIDGG  MAYHQEPPGK
Consensus   eWLNKsGfFD  EEFNHWGGED  VEFGYRLFrk  GcFFrtIDGg  MAYHQEPPGK
```

Fig. 20B

```
          401
PmHAS     ENETDREAGK  NITLDIMREK  VPYIYRKLLP  IEDSHINRVP  LVSIYIPAYN
PmCS      ENETEREAGK  SITLKIVKEK  VPYIYRKLLP  IEDSHIHRIP  LVSIYIPAYN
Consensus ENET#REAGK  nITLdImrEK  VPYIYRKLLP  IEDSHInR!P  LVSIYIPAYN 451                                                     500
PmHAS     CANYIQRCVD  SALNQTVVDL  EVCICNDGST  DNTLEVINKL  YGNNPRVRIM
PmCS      CANYIQRCVD  SALNQTVVDL  EVCICNDGST  DNTIEVINKL  YGNNPRVRIM
Consensus CANYIQRCVD  SALNQTVVDL  EVCICNDGST  DNTiEVINKL  YGNNPRVRIM 501                                                     550
PmHAS     SKPNGGIASA  SNAAVSFAKG  YYIGQLDSDD  YLEPDAVELC  LKEFLKDKTL
PmCS      SKPNGGIASA  SNAAVSFAKG  YYIGQLDSDD  YVEPDAVELC  LKEFLKDKTL
Consensus SKPNGGIASA  SNAAVSFAKG  YYIGQLDSDD  YlEPDAVELC  LKEFLKDKTL 551                                                     600
PmHAS     ACVYTTNRNV  NPDGSLIANG  YNWPEFSREK  LTTAMIAHHF  RMFTIRAWHL
PmCS      ACVYTTNRNV  NPDGSLIANG  YNWPEFSREK  LTTAMIAHHF  RMFTIRAWHL
Consensus ACVYTTNRNV  NPDGSLIANG  YNWPEFSREK  LTTAMIAHHF  RMFTIRAWHL
```

Fig. 20C

```
           601                                                              650
PmHAS      TDGFNEKIEN AVDYDMFLKL SEVGKFKHLN KICYNRVLHG DNTSIKKLGI
PmCS       TDGFNENIEN AVDYDMFLKL SEVGKFKHLN KICYNRVLHG DNTSIKKLGI
Consensus  TDGFNEnIEN AVDYDMFLKL SEVGKFKHLN KICYNRVLHG DNTSIKKLGI 651                                                              700
PmHAS      QKKNHFVVVN QSLNRQGITY YNYDEFDDLD ESRKYIFNKT AEYQEEIDIL
PmCS       QKKNHFVVVN QSLNRQGINY YNYDKFDDLD ESRKYIFNKT AEYQEEIDML
Consensus  QKKNHFVVVN QSLNRQGInY YNYDeFDDLD ESRKYIFNKT AEYQEEIDiL 701                                                              750
PmHAS      KDIKIIQNKD AKIAVSIFYP NTLNGLVKKL NNIIEYNKNI FVIVLHVDKN
PmCS       KDLKLIQNKD AKIAVSIFYP NTLNGLVKKL NNIIEYNKNI FVIILHLDKN
Consensus  KDiKiIQNKD AKIAVSIFYP NTLNGLVKKL NNIIEYNKNI FVIiLHlDKN 751                                                              800
PmHAS      HLTPDIKKEI LAFYHKHQVN ILLNNDISYY TSNRLIKTEA HLSNINKLSQ
PmCS       HLTPDIKKEI LAFYHKHQVN ILLNNDISYY TSNRLIKTEA HLSNINKLSQ
Consensus  HLTPDIKKEI LAFYHKHQVN ILLNNDISYY TSNRLIKTEA HLSNINKLSQ
```

Fig. 20D

```
            801                                                      850
PmHAS       LNLNCEYIIF  DNHDSLFVKN  DSYAYMKKYD  VGMNFSALTH  DWIEKINAHP
PmCS        LNLNCEYIIF  DNHDSLFVKN  DSYAYMKKYD  VGMNFSALTH  DWIEKINAHP
Consensus   LNLNCEYIIF  DNHDSLFVKN  DSYAYMKKYD  VGMNFSALTH  DWIEKINAHP 851                                                      900
PmHAS       PFKKLIKTYF  NDNDLKSMNV  KGASQGMFMT  YALAHELLTI  IKEVITSCQS
PmCS        PFKKLIKTYF  NDNDLRSMNV  KGASQGMFMK  YALPHELLTI  IKEVITSCQS
Consensus   PFKKLIKTYF  NDNDLrSMNV  KGASQGMFMk  YALaHaLLTI  IKEVITSCQS 901                                                      950
PmHAS       IDSVPEYNTE  DIWFQFALLI  LEKKTGHVFN  KTSTLTYMPW  ERKLQWTNEQ
PmCS        IDSVPEYNTE  DIWFQFALLI  LEKKTGHVFN  KTSTLTYMPW  ERKLQWTNEQ
Consensus   IDSVPEYNTE  DIWFQFALLI  LEKKTGHVFN  KTSTLTYMPW  ERKLQWTNEQ 951              965  (SEQ ID NO:)
PmHAS       IESAKRGENI  PVNKFIINSI  TL    1
PmCS        IQSAKKGENI  PVNKFIINSI  TL    3
Consensus   I#SAKrGENI  PVNKFIINSI  TL    7
```

Fig. 20E

SEQUENCE LISTING

```
<160> NUMBER OF SEQ ID NOS: 28

<210> SEQ ID NO 1
<211> LENGTH: 972
<212> TYPE: PRT
<213> ORGANISM: Pasteurella multocida

<400> SEQUENCE: 1

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Gln Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220
```

```
Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
            245                 250                 255

Val His Ser Tyr Val Ala Glu Leu Leu Glu Asp Asp Leu Thr Ile
        260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
            355                 360                 365

Glu Asp Val Glu Phe Gly Tyr Arg Leu Phe Arg Tyr Gly Ser Phe Phe
        370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
            435                 440                 445

Tyr Asn Cys Ala Asn Tyr Ile Gln Arg Cys Val Asp Ser Ala Leu Asn
450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
            485                 490                 495

Val Arg Ile Met Ser Lys Pro Asn Gly Gly Ile Ala Ser Ala Ser Asn
            500                 505                 510

Ala Ala Val Ser Phe Ala Lys Gly Tyr Tyr Ile Gly Gln Leu Asp Ser
            515                 520                 525

Asp Asp Tyr Leu Glu Pro Asp Ala Val Glu Leu Cys Leu Lys Glu Phe
530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
            565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
            595                 600                 605

Glu Asn Ala Val Asp Tyr Asp Met Phe Leu Lys Leu Ser Glu Val Gly
            610                 615                 620

Lys Phe Lys His Leu Asn Lys Ile Cys Tyr Asn Arg Val Leu His Gly
625                 630                 635                 640
```

-continued

```
Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile Lys
    690                 695                 700
Ile Ile Gln Asn Lys Asp Ala Lys Ile Ala Val Ser Ile Phe Tyr Pro
705                 710                 715                 720
Asn Thr Leu Asn Gly Leu Val Lys Lys Leu Asn Asn Ile Ile Glu Tyr
                725                 730                 735
Asn Lys Asn Ile Phe Val Ile Val Leu His Val Asp Lys Asn His Leu
            740                 745                 750
Thr Pro Asp Ile Lys Lys Glu Ile Leu Ala Phe Tyr His Lys His Gln
        755                 760                 765

Val Asn Ile Leu Leu Asn Asn Asp Ile Ser Tyr Tyr Thr Ser Asn Arg
    770                 775                 780

Leu Ile Lys Thr Glu Ala His Leu Ser Asn Ile Asn Lys Leu Ser Gln
785                 790                 795                 800
Leu Asn Leu Asn Cys Glu Tyr Ile Ile Phe Asp Asn His Asp Ser Leu
                805                 810                 815
Phe Val Lys Asn Asp Ser Tyr Ala Tyr Met Lys Lys Tyr Asp Val Gly
            820                 825                 830
Met Asn Phe Ser Ala Leu Thr His Asp Trp Ile Glu Lys Ile Asn Ala
        835                 840                 845
His Pro Pro Phe Lys Lys Leu Ile Lys Thr Tyr Phe Asn Asp Asn Asp
    850                 855                 860
Leu Lys Ser Met Asn Val Lys Gly Ala Ser Gln Gly Met Phe Met Thr
865                 870                 875                 880
Tyr Ala Leu Ala His Glu Leu Leu Thr Ile Ile Lys Glu Val Ile Thr
                885                 890                 895
Ser Cys Gln Ser Ile Asp Ser Val Pro Glu Tyr Asn Thr Glu Asp Ile
            900                 905                 910
Trp Phe Gln Phe Ala Leu Leu Ile Leu Glu Lys Lys Thr Gly His Val
        915                 920                 925
Phe Asn Lys Thr Ser Thr Leu Thr Tyr Met Pro Trp Glu Arg Lys Leu
    930                 935                 940
Gln Trp Thr Asn Glu Gln Ile Glu Ser Ala Lys Arg Gly Glu Asn Ile
945                 950                 955                 960
Pro Val Asn Lys Phe Ile Ile Asn Ser Ile Thr Leu
                965                 970
```

<210> SEQ ID NO 2
<211> LENGTH: 2937
<212> TYPE: DNA
<213> ORGANISM: Pasteurella multocida

<400> SEQUENCE: 2

```
atttttaag gacagaaaat gaatacatta tcacaagcaa taaaagcata taacagcaat      60
gactatcaat tagcactcaa attatttgaa aagtcggcgg aaatctatgg acggaaaatt     120
gttgaatttc aaattaccaa atgccaagaa aaactctcag cacatccttc tgttaattca     180
gcacatcttt ctgtaaataa agaagaaaaa gtcaatgttt gcgatagtcc gttagatatt     240
```

-continued

```
gcaacacaac tgttactttc aacgtaaaa aaattagtac tttctgactc ggaaaaaaac    300
acgttaaaaa ataaatggaa attgctcact gagaagaaat ctgaaaatgc ggaggtaaga    360
gcggtcgccc ttgtaccaaa agattttccc aaagatctgg ttttagcgcc tttacctgat    420
catgttaatg attttacatg gtacaaaaag cgaaagaaaa gacttggcat aaaacctgaa    480
catcaacatg ttggtctttc tattatcgtt acaacattca atcgaccagc aattttatcg    540
attacattag cctgtttagt aaaccaaaaa acacattacc cgtttgaagt tatcgtgaca    600
gatgatggta gtcaggaaga tctatcaccg atcattcgcc aatatgaaaa taaattggat    660
attcgctacg tcagacaaaa agataacggt tttcaagcca gtgccgctcg gaatatggga    720
ttacgcttag caaaatatga ctttattggc ttactcgact gtgatatggc gccaaatcca    780
ttatgggttc attcttatgt tgcagagcta ttagaagatg atgatttaac aatcattggt    840
ccaagaaaat acatcgatac acaacatatt gacccaaaag acttcttaaa taacgcgagt    900
ttgcttgaat cattaccaga agtgaaaacc aataatagtg ttgccgcaaa aggggaagga    960
acagtttctc tggattggcg cttagaacaa ttcgaaaaaa cagaaaatct ccgcttatcc    1020
gattcgcctt tccgtttttt tgcggcgggt aatgttgctt tcgctaaaaa atggctaaat    1080
aaatccggtt tctttgatga ggaatttaat cactggggtg gagaagatgt ggaatttgga    1140
tatcgcttat tccgttacgg tagtttcttt aaaactattg atggcattat ggcctaccat    1200
caagagccac caggtaaaga aaatgaaacc gatcgtgaag cgggaaaaaa tattacgctc    1260
gatattatga gagaaaaggt cccttatatc tatagaaaac ttttaccaat agaagattcg    1320
catatcaata gagtaccttt agtttcaatt tatatcccag cttataactg tgcaaactat    1380
attcaacgtt gcgtagatag tgcactgaat cagactgttg ttgatctcga ggtttgtatt    1440
tgtaacgatg gttcaacaga taataccta gaagtgatca ataagcttta tggtaataat    1500
cctagggtac gcatcatgtc taaaccaaat ggcggaatag cctcagcatc aaatgcagcc    1560
gtttcttttg ctaaaggtta ttacattggg cagttagatt cagatgatta tcttgagcct    1620
gatgcagttg aactgtgttt aaaagaattt ttaaaagata aaacgctagc ttgtgtttat    1680
accactaata gaaacgtcaa tccggatggt agcttaatcg ctaatggtta caattggcca    1740
gaattttcac gagaaaaact cacaacggct atgattgctc accactttag aatgttcacg    1800
attagagctt ggcatttaac tgatggattc aatgaaaaaa ttgaaaatgc cgtagactat    1860
gacatgttcc tcaaactcag tgaagttgga aaatttaaac atcttaataa aatctgctat    1920
aaccgtgtat tacatggtga taacacatca attaagaaac ttggcattca aaagaaaaac    1980 catttgttg tagtcaatca gtcattaaat agacaaggca taacttatta taattatgac    2040
gaatttgatg atttagatga agtagaaag tatattttca ataaaaccgc tgaatatcaa    2100
gaagagattg atatcttaaa agatattaaa atcatccaga ataaagatgc caaaatcgca    2160
gtcagtattt tttatcccaa tacattaaac ggcttagtga aaaaactaaa caatattatt    2220
gaatataata aaaatatatt cgttattgtt ctacatgttg ataagaatca tcttacacca    2280
gatatcaaaa aagaaatact agccttctat cataaacatc aagtgaatat tttactaaat    2340
aatgatatct catattacac gagtaataga ttaataaaaa ctgaggcgca tttaagtaat    2400
attaataaat taagtcagtt aaatctaaat tgtgaataca tcattttga taatcatgac    2460 agcctattcg ttaaaaatga cagctatgct tatatgaaaa aatatgatgt cggcatgaat    2520
ttctcagcat taacacatga ttggatcgag aaaatcaatg cgcatccacc atttaaaaag    2580
ctcattaaaa cttatttta tgacaatgac ttaaaaagta tgaatgtgaa agggcatca    2640
```

```
caaggtatgt ttatgacgta tgcgctagcg catgagcttc tgacgattat taaagaagtc    2700
atcacatctt gccagtcaat tgatagtgtg ccagaatata acactgagga tatttggttc    2760
caatttgcac ttttaatctt agaaaagaaa accggccatg tatttaataa acatcgacc     2820 ctgacttata tgccttggga acgaaaatta caatggacaa atgaacaaat tgaaagtgca    2880
aaaagaggag aaaatatacc tgttaacaag ttcattatta atagtataac tctataa      2937
```

```
<210> SEQ ID NO 3
<211> LENGTH: 972
<212> TYPE: PRT
<213> ORGANISM: Pasteurella multocida

<400> SEQUENCE: 3

Met Asn Thr Leu Ser Gln Ala Ile Lys Ala Tyr Asn Cys Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Asn Ser Tyr Val Ser Glu Asp Lys Lys
    50                  55                  60

Asn Ser Val Cys Asp Ser Ser Leu Asp Ile Ala Thr Gln Leu Leu Leu
65                  70                  75                  80

Ser Asn Val Lys Lys Leu Thr Leu Ser Glu Ser Glu Lys Asn Ser Leu
                85                  90                  95

Lys Asn Lys Trp Lys Ser Ile Thr Gly Lys Lys Ser Glu Asn Ala Glu
            100                 105                 110

Ile Arg Lys Val Glu Leu Val Pro Lys Asp Phe Pro Lys Asp Leu Val
        115                 120                 125

Leu Ala Pro Leu Pro Asp His Val Asn Asp Phe Thr Trp Tyr Lys Asn
    130                 135                 140

Arg Lys Lys Ser Leu Gly Ile Lys Pro Val Asn Lys Asn Ile Gly Leu
145                 150                 155                 160

Ser Ile Ile Ile Pro Thr Phe Asn Arg Ser Arg Ile Leu Asp Ile Thr
                165                 170                 175

Leu Ala Cys Leu Val Asn Gln Lys Thr Asn Tyr Pro Phe Glu Val Val
            180                 185                 190

Val Ala Asp Asp Gly Ser Lys Glu Asn Leu Leu Thr Ile Val Gln Lys
        195                 200                 205

Tyr Glu Gln Lys Leu Asp Ile Lys Tyr Val Arg Gln Lys Asp Tyr Gly
    210                 215                 220

Tyr Gln Leu Cys Ala Val Arg Asn Leu Gly Leu Arg Thr Ala Lys Tyr
225                 230                 235                 240

Asp Phe Val Ser Ile Leu Asp Cys Asp Met Ala Pro Gln Gln Leu Trp
                245                 250                 255

Val His Ser Tyr Leu Thr Glu Leu Leu Glu Asp Asn Asp Ile Val Leu
            260                 265                 270

Ile Gly Pro Arg Lys Tyr Val Asp Thr His Asn Ile Thr Ala Glu Gln
        275                 280                 285

Phe Leu Asn Asp Pro Tyr Leu Ile Glu Ser Leu Pro Glu Thr Ala Thr
    290                 295                 300

Asn Asn Asn Pro Ser Ile Thr Ser Lys Gly Asn Ile Ser Leu Asp Trp
305                 310                 315                 320
```

-continued

Arg Leu Glu His Phe Lys Lys Thr Asp Asn Leu Arg Leu Cys Asp Ser
                325                 330                 335

Pro Phe Arg Tyr Phe Ser Cys Gly Asn Val Ala Phe Ser Lys Glu Trp
                340                 345                 350

Leu Asn Lys Val Gly Trp Phe Asp Glu Phe Asn His Trp Gly Gly
                355                 360                 365

Glu Asp Val Glu Phe Gly Tyr Arg Leu Phe Ala Lys Gly Cys Phe Phe
                370                 375                 380

Arg Val Ile Asp Gly Gly Met Ala Tyr His Gln Glu Pro Pro Gly Lys
385                 390                 395                 400

Glu Asn Glu Thr Asp Arg Glu Ala Gly Lys Ser Ile Thr Leu Lys Ile
                405                 410                 415

Val Lys Glu Lys Val Pro Tyr Ile Tyr Arg Lys Leu Leu Pro Ile Glu
                420                 425                 430

Asp Ser His Ile His Arg Ile Pro Leu Val Ser Ile Tyr Ile Pro Ala
                435                 440                 445

Tyr Asn Cys Ala Asn Tyr Ile Gln Arg Cys Val Asp Ser Ala Leu Asn
                450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
                500                 505                 510

Ala Ala Val Ser Phe Ala Lys Gly Tyr Tyr Ile Gly Gln Leu Asp Ser
                515                 520                 525

Asp Asp Tyr Leu Glu Pro Asp Ala Val Glu Leu Cys Leu Lys Glu Phe
                530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
                580                 585                 590

Phe Thr Ile Arg Ala Trp His Leu Thr Asp Gly Phe Asn Glu Asn Ile
                595                 600                 605

Glu Asn Ala Val Asp Tyr Asp Met Phe Leu Lys Leu Ser Glu Val Gly
                610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Asn Tyr Tyr Asn
                660                 665                 670

Tyr Asp Lys Phe Asp Asp Leu Asp Glu Ser Arg Lys Tyr Ile Phe Asn
                675                 680                 685

Lys Thr Ala Glu Tyr Gln Glu Glu Met Asp Ile Leu Lys Asp Leu Lys
                690                 695                 700

Leu Ile Gln Asn Lys Asp Ala Lys Ile Ala Val Ser Ile Phe Tyr Pro
705                 710                 715                 720

Asn Thr Leu Asn Gly Leu Val Lys Lys Leu Asn Asn Ile Ile Glu Tyr
                725                 730                 735

Asn Lys Asn Ile Phe Val Ile Ile Leu His Val Asp Lys Asn His Leu

```
                    740                 745                 750
Thr Pro Asp Ile Lys Lys Glu Ile Leu Ala Phe Tyr His Lys His Gln
            755                 760                 765
Val Asn Ile Leu Leu Asn Asn Asp Ile Ser Tyr Tyr Thr Ser Asn Arg
        770                 775                 780
Leu Ile Lys Thr Glu Ala His Leu Ser Asn Ile Asn Lys Leu Ser Gln
785                 790                 795                 800
Leu Asn Leu Asn Cys Glu Tyr Ile Ile Phe Asp Asn His Asp Ser Leu
                805                 810                 815
Phe Val Lys Asn Asp Ser Tyr Ala Tyr Met Lys Lys Tyr Asp Val Gly
            820                 825                 830
Met Asn Phe Ser Ala Leu Thr His Asp Trp Ile Glu Lys Ile Asn Ala
        835                 840                 845
His Pro Pro Phe Lys Lys Leu Ile Lys Thr Tyr Phe Asn Asp Asn Asp
    850                 855                 860
Leu Arg Ser Met Asn Val Lys Gly Ala Ser Gln Gly Met Phe Met Lys
865                 870                 875                 880
Tyr Ala Leu Pro His Glu Leu Leu Thr Ile Ile Lys Glu Val Ile Thr
                885                 890                 895
Ser Cys Gln Ser Ile Asp Ser Val Pro Glu Tyr Asn Thr Glu Asp Ile
            900                 905                 910
Trp Phe Gln Phe Ala Leu Leu Ile Leu Glu Lys Lys Thr Gly His Val
        915                 920                 925
Phe Asn Lys Thr Ser Thr Leu Thr Tyr Met Pro Trp Glu Arg Lys Leu
    930                 935                 940
Gln Trp Thr Asn Glu Gln Ile Gln Ser Ala Lys Lys Gly Glu Asn Ile
945                 950                 955                 960
Pro Val Asn Lys Phe Ile Ile Asn Ser Ile Thr Leu
                965                 970

<210> SEQ ID NO 4
<211> LENGTH: 45
<212> TYPE: PRT
<213> ORGANISM: Pasteurella multocida

<400> SEQUENCE: 4

Tyr Ile Asp Asn Gln Val Leu Lys Ala Lys Pro Arg Leu Tyr Gly Ala
1               5                   10                  15

```
<210> SEQ ID NO 6
<211> LENGTH: 47
<212> TYPE: PRT
<213> ORGANISM: Escherichia coli

<400> SEQUENCE: 6

Phe Ile Glu Asn Gln Glu Ile Lys Lys Leu Pro Pro Val Leu Tyr
1               5                   10                  15
Gly Ala Ala Glu Gln Ile Lys Gln Glu Leu Gly Tyr Arg Leu Gly Tyr
            20                  25                  30
Ile Ile Val Ser Tyr Ser Lys Ser Leu Lys Gly Ile Ile Thr Met
        35                  40                  45

<210> SEQ ID NO 7
<211> LENGTH: 972
<212> TYPE: PRT
<213> ORGANISM: Artificial Sequence
<220> FEATURE:
<223> OTHER INFORMATION: Consensus of alignment of SEQ ID NOS:1 and 3
<220> FEATURE:
<221> NAME/KEY: MISC_FEATURE
<222> LOCATION: (17)..(17)
<223> OTHER INFORMATION: Asn, Asp, Glu or Gln
<220> FEATURE:
<221> NAME/KEY: MISC_FEATURE
<222> LOCATION: (62)..(62)
<223> OTHER INFORMATION: Asn, Asp, Glu or Gln
<220> FEATURE:
<221> NAME/KEY: MISC_FEATURE
<222> LOCATION: (90)..(90)
<223> OTHER INFORMATION: Asn, Asp, Glu or Gln
<220> FEATURE:
<221> NAME/KEY: MISC_FEATURE
<222> LOCATION: (113)..(113)
<223> OTHER INFORMATION: Ile or Val
<220> FEATURE:
<221> NAME/KEY: MISC_FEATURE
<222> LOCATION: (158)..(158)
<223> OTHER INFORMATION: Ile or Val
<220> FEATURE:
<221> NAME/KEY: MISC_FEATURE
<222> LOCATION: (164)..(164)
<223> OTHER INFORMATION: Ile or Val
<220> FEATURE:
<221> NAME/KEY: MISC_FEATURE
<222> LOCATION: (192)..(192)
<223> OTHER INFORMATION: Ile or Val
<220> FEATURE:
<221> NAME/KEY: MISC_FEATURE
<222> LOCATION: (201)..(201)
<223> OTHER INFORMATION: Asn, Asp, Glu or Gln
<220> FEATURE:
<221> NAME/KEY: MISC_FEATURE
<222> LOCATION: (206)..(206)
<223> OTHER INFORMATION: Ile or Val
<220> FEATURE:
<221> NAME/KEY: MISC_FEATURE
<222> LOCATION: (211)..(211)
<223> OTHER INFORMATION: Asn, Asp, Glu or Gln
<220> FEATURE:
<221> NAME/KEY: MISC_FEATURE
<222> LOCATION: (225)..(225)
<223> OTHER INFORMATION: Phe or Tyr
<220> FEATURE:
<221> NAME/KEY: MISC_FEATURE
<222> LOCATION: (233)..(233)
<223> OTHER INFORMATION: Met or Leu
<220> FEATURE:
<221> NAME/KEY: MISC_FEATURE
<222> LOCATION: (243)..(243)
<223> OTHER INFORMATION: Ile or Val
<220> FEATURE:
<221> NAME/KEY: MISC_FEATURE
<222> LOCATION: (253)..(253)
<223> OTHER INFORMATION: Asn, Asp, Glu or Gln
```

```
<220> FEATURE:
<221> NAME/KEY: MISC_FEATURE
<222> LOCATION: (279)..(279)
<223> OTHER INFORMATION: Ile or Val
<220> FEATURE:
<221> NAME/KEY: MISC_FEATURE
<222> LOCATION: (288)..(288)
<223> OTHER INFORMATION: Asn, Asp, Glu or Gln
<220> FEATURE:
<221> NAME/KEY: MISC_FEATURE
<222> LOCATION: (292)..(292)
<223> OTHER INFORMATION: Asn, Asp, Glu or Gln
<220> FEATURE:
<221> NAME/KEY: MISC_FEATURE
<222> LOCATION: (316)..(316)
<223> OTHER INFORMATION: Ile or Val
<220> FEATURE:
<221> NAME/KEY: MISC_FEATURE
<222> LOCATION: (329)..(329)
<223> OTHER INFORMATION: Phe or Tyr
<220> FEATURE:
<221> NAME/KEY: MISC_FEATURE
<222> LOCATION: (340)..(340)
<223> OTHER INFORMATION: Phe or Tyr
<220> FEATURE:
<221> NAME/KEY: MISC_FEATURE
<222> LOCATION: (405)..(405)
<223> OTHER INFORMATION: Asn, Asp, Glu or Gln
<220> FEATURE:
<221> NAME/KEY: MISC_FEATURE
<222> LOCATION: (439)..(439)
<223> OTHER INFORMATION: Ilr or Val
<220> FEATURE:
<221> NAME/KEY: MISC_FEATURE
<222> LOCATION: (744)..(744)
<223> OTHER INFORMATION: Ilr or Val
<220> FEATURE:
<221> NAME/KEY: MISC_FEATURE
<222> LOCATION: (952)..(952)
<223> OTHER INFORMATION: Asn, Asp, Glu or Gln

<400> SEQUENCE: 7

Met Asn Thr Leu Ser Gln Ala Ile Lys Ala Tyr Asn Cys Asn Asp Tyr
1               5                   10                  15

Xaa Leu Ala Leu Lys Leu Phe Glu Lys Ser Ala Glu Ile Tyr Gly Arg
            20                  25                  30

Lys Ile Val Glu Phe Gln Ile Ile Lys Cys Gln Glu Lys Leu Ser Ala
        35                  40                  45

Asn Pro Ser Val Asn Glu Ala Asn Leu Ser Val Asn Glu Xaa Glu Lys
    50                  55                  60

Asn Asn Val Cys Asp Ser Pro Leu Asp Ile Ala Thr Gln Leu Leu Ile
65                  70                  75                  80

Ser Asn Val Lys Lys Leu Thr Leu Ser Xaa Ser Glu Lys Asn Ser Leu
                85                  90                  95

Lys Asn Lys Trp Lys Leu Ile Thr Glu Lys Lys Ser Glu Asn Ala Glu
            100                 105                 110

Xaa Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Asn
    130                 135                 140

Arg Lys Lys Arg Leu Gly Ile Lys Pro Glu Asn Gln Asn Xaa Gly Leu
145                 150                 155                 160

Ser Ile Ile Xaa Pro Thr Phe Asn Arg Pro Ala Ile Leu Asp Ile Thr
                165                 170                 175

Leu Ala Cys Leu Val Asn Gln Lys Thr Asn Tyr Pro Phe Glu Val Xaa
            180                 185                 190
```

```
Val Ala Asp Asp Gly Ser Gln Glu Xaa Leu Leu Pro Ile Xaa Arg Gln
        195                 200                 205

Tyr Glu Xaa Lys Leu Asp Ile Arg Tyr Val Arg Gln Lys Asp Asn Gly
    210                 215                 220

Xaa Gln Ala Cys Ala Ala Arg Asn Xaa Gly Leu Arg Leu Ala Lys Tyr
225                 230                 235                 240

Asp Phe Xaa Gly Ile Leu Asp Cys Asp Met Ala Pro Xaa Gln Leu Trp
            245                 250                 255

Val His Ser Tyr Leu Ala Glu Leu Leu Glu Asp Asp Ile Thr Ile
                260                 265                 270

Ile Gly Pro Arg Lys Tyr Xaa Asp Thr Gln Asn Ile Asp Ala Glu Xaa
            275                 280                 285

Phe Leu Asn Xaa Ala Ser Leu Ile Glu Ser Leu Pro Glu Thr Ala Thr
        290                 295                 300

Asn Asn Asn Pro Ala Ala Lys Gly Gly Asn Xaa Ser Leu Asp Trp
305                 310                 315                 320

Arg Leu Glu Gln Phe Glu Lys Thr Xaa Asn Leu Arg Leu Cys Asp Ser
                325                 330                 335

Pro Phe Arg Xaa Phe Ala Ala Gly Asn Val Ala Phe Ala Lys Glu Trp
            340                 345                 350

Leu Asn Lys Ser Gly Phe Phe Asp Glu Glu Phe Asn His Trp Gly Gly
                355                 360                 365

Glu Asp Val Glu Phe Gly Tyr Arg Leu Phe Arg Lys Gly Cys Phe Phe
        370                 375                 380

Arg Thr Ile Asp Gly Gly Met Ala Tyr His Gln Glu Pro Pro Gly Lys
385                 390                 395                 400

Glu Asn Glu Thr Xaa Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Xaa Pro Leu Val Ser Ile Tyr Ile Pro Ala
        435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Ile Glu Val Ile Asn Lys Leu Tyr Gly Asn Asn Pro Arg
            485                 490                 495

Val Arg Ile Met Ser Lys Pro Asn Gly Ile Ala Ser Ala Ser Asn
        500                 505                 510

Ala Ala Val Ser Phe Ala Lys Gly Tyr Tyr Ile Gly Gln Leu Asp Ser
            515                 520                 525

Asp Asp Tyr Leu Glu Pro Asp Ala Val Glu Leu Cys Leu Lys Glu Phe
        530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Asn Ile
        595                 600                 605

Glu Asn Ala Val Asp Tyr Asp Met Phe Leu Lys Leu Ser Glu Val Gly
```

-continued

```
            610                 615                 620
Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Asn Tyr Tyr Asn
                660                 665                 670

Tyr Asp Glu Phe Asp Asp Leu Asp Glu Ser Arg Lys Tyr Ile Phe Asn
                675                 680                 685

Lys Thr Ala Glu Tyr Gln Glu Glu Ile Asp Ile Leu Lys Asp Ile Lys
690                 695                 700

Ile Ile Gln Asn Lys Asp Ala Lys Ile Ala Val Ser Ile Phe Tyr Pro
705                 710                 715                 720

Asn Thr Leu Asn Gly Leu Val Lys Lys Leu Asn Asn Ile Ile Glu Tyr
                725                 730                 735

Asn Lys Asn Ile Phe Val Ile Xaa Leu His Leu Asp Lys Asn His Leu
                740                 745                 750

Thr Pro Asp Ile Lys Lys Glu Ile Leu Ala Phe Tyr His Lys His Gln
                755                 760                 765

Val Asn Ile Leu Leu Asn Asn Asp Ile Ser Tyr Tyr Thr Ser Asn Arg
770                 775                 780

Leu Ile Lys Thr Glu Ala His Leu Ser Asn Ile Asn Lys Leu Ser Gln
785                 790                 795                 800

Leu Asn Leu Asn Cys Glu Tyr Ile Ile Phe Asp Asn His Asp Ser Leu
                805                 810                 815

Phe Val Lys Asn Asp Ser Tyr Ala Tyr Met Lys Lys Tyr Asp Val Gly
                820                 825                 830

Met Asn Phe Ser Ala Leu Thr His Asp Trp Ile Glu Lys Ile Asn Ala
                835                 840                 845

His Pro Pro Phe Lys Lys Leu Ile Lys Thr Tyr Phe Asn Asp Asn Asp
850                 855                 860

Leu Arg Ser Met Asn Val Lys Gly Ala Ser Gln Gly Met Phe Met Lys
865                 870                 875                 880

Tyr Ala Leu Ala His Ala Leu Leu Thr Ile Ile Lys Glu Val Ile Thr
                885                 890                 895

Ser Cys Gln Ser Ile Asp Ser Val Pro Glu Tyr Asn Thr Glu Asp Ile
                900                 905                 910

Trp Phe Gln Phe Ala Leu Leu Ile Leu Glu Lys Lys Thr Gly His Val
                915                 920                 925

Phe Asn Lys Thr Ser Thr Leu Thr Tyr Met Pro Trp Glu Arg Lys Leu
                930                 935                 940

Gln Trp Thr Asn Glu Gln Ile Xaa Ser Ala Lys Arg Gly Glu Asn Ile
945                 950                 955                 960

Pro Val Asn Lys Phe Ile Ile Asn Ser Ile Thr Leu
                965                 970
```

<210> SEQ ID NO 8
<211> LENGTH: 101
<212> TYPE: PRT
<213> ORGANISM: Pasteurella multocida

<400> SEQUENCE: 8

```
Ile Asn Arg Val Pro Leu Val Ser Ile Tyr Ile Pro Ala Tyr Asn Cys
1               5                   10                  15
```

```
Ala Asn Tyr Ile Gln Arg Cys Val Asp Ser Ala Leu Asn Gln Thr Val
            20                  25                  30

Val Asp Leu Glu Val Cys Ile Cys Asn Asp Gly Ser Thr Asp Asn Thr
        35                  40                  45

Leu Glu Val Ile Asn Lys Leu Tyr Gly Asn Asn Pro Arg Val Arg Ile
    50                  55                  60

Met Ser Lys Pro Asn Gly Gly Ile Ala Ser Ala Ser Asn Ala Ala Val
65                  70                  75                  80

Ser Phe Ala Lys Gly Tyr Tyr Ile Gly Gln Leu Asp Ser Asp Asp Tyr
                85                  90                  95

Leu Glu Pro Asp Ala
            100

<210> SEQ ID NO 9
<211> LENGTH: 101
<212> TYPE: PRT
<213> ORGANISM: Streptococcus thermophilus

<400> SEQUENCE: 9

Met Tyr Leu Lys Ser Leu Ile Ser Ile Val Ile Pro Val Tyr Asn Val
1               5                   10                  15

Glu Lys Tyr Leu Glu Lys Cys Leu Gln Ser Val Gln Asn Gln Thr Tyr
            20                  25                  30

Asn Asn Phe Glu Val Ile Leu Val Asn Asp Gly Ser Thr Asp Ser Ser
        35                  40                  45

Leu Ser Ile Cys Glu Lys Phe Val Asn Gln Asp Lys Arg Phe Ser Val
    50                  55                  60

Phe Ser Lys Glu Asn Gly Gly Met Ser Ser Ala Arg Asn Phe Gly Ile
65                  70                  75                  80

Lys Lys Ala Lys Gly Ser Phe Ile Thr Phe Val Asp Ser Asp Asp Tyr
                85                  90                  95

Ile Val Lys Asp Tyr
            100

<210> SEQ ID NO 10
<211> LENGTH: 99
<212> TYPE: PRT
<213> ORGANISM: Streptococcus pneumoniae

<400> SEQUENCE: 10

Met Glu Asp Leu Val Ser Ile Val Val Pro Val Tyr Asn Val Glu Lys
1               5                   10                  15

Tyr Leu Lys Lys Ser Ile Glu Ser Ile Leu Asn Gln Thr Tyr Asp Asn
            20                  25                  30

Leu Glu Val Leu Leu Val Asp Asp Gly Ser Thr Asp Ser Ser Gly Glu
        35                  40                  45

Ile Cys Asp Ser Phe Ile Lys Val Asp Ser Arg Ile Arg Val Phe His
    50                  55                  60

Lys Glu Asn Gly Gly Leu Ser Asp Ala Arg Asn Phe Gly Ile Glu His
65                  70                  75                  80

Met Lys Gly Gln Tyr Val Ser Phe Ile Asp Gly Asp Tyr Ile Ser
                85                  90                  95

Lys Asp Tyr

<210> SEQ ID NO 11
<211> LENGTH: 101
<212> TYPE: PRT
```

<213> ORGANISM: Haemophilus influenzae

<400> SEQUENCE: 11

```
Met Met Met Pro Leu Ile Ser Ile Ile Met Pro Val Tyr Asn Ala Glu
1               5                   10                  15

Cys Tyr Leu Asn Gln Gly Ile Leu Ser Cys Leu Asn Gln Ser Tyr Gln
                20                  25                  30

Asn Ile Glu Leu Ile Leu Ile Asp Asp Gly Ser Thr Asp Lys Ser Ile
            35                  40                  45

Glu Ile Ile Asn Asn Ile Asp Lys Asp Lys Arg Val Lys Leu Phe
50                  55                  60

Phe Thr Pro Thr Asn Gln Gly Pro Ala Ala Arg Asn Ile Gly Leu
65                  70                  75                  80

Glu Lys Ala Gln Gly Asp Tyr Ile Thr Phe Leu Asp Ser Asp Asp Phe
                85                  90                  95

Ile Ala Asn Asp Lys
            100
```

<210> SEQ ID NO 12
<211> LENGTH: 107
<212> TYPE: PRT
<213> ORGANISM: Streptococcus pyogenes

<400> SEQUENCE: 12

```
Pro His Asp Tyr Lys Val Ala Ala Val Ile Pro Ser Tyr Asn Glu Asp
1               5                   10                  15

Ala Glu Ser Leu Leu Glu Thr Leu Lys Ser Val Leu Ala Gln Thr Tyr
                20                  25                  30

Pro Leu Ser Glu Ile Tyr Ile Val Asp Asp Gly Ser Ser Asn Thr Asp
            35                  40                  45

Ala Ile Gln Leu Ile Glu Glu Tyr Val Asn Arg Glu Val Asp Ile Cys
50                  55                  60

Arg Asn Val Ile Val His Arg Ser Leu Val Asn Lys Gly Lys Arg His
65                  70                  75                  80

Ala Gln Ala Trp Ala Phe Glu Arg Ser Asp Ala Asp Val Phe Leu Thr
                85                  90                  95

Val Asp Ser Asp Thr Tyr Ile Tyr Pro Asn Ala
            100                 105
```

<210> SEQ ID NO 13
<211> LENGTH: 108
<212> TYPE: PRT
<213> ORGANISM: Artificial Sequence
<220> FEATURE:
<223> OTHER INFORMATION: Consensus of Alignment of SEQ ID NOS:8-12
<220> FEATURE:
<221> NAME/KEY: MISC_FEATURE
<222> LOCATION: (1)..(5)
<223> OTHER INFORMATION: any amino acid
<220> FEATURE:
<221> NAME/KEY: MISC_FEATURE
<222> LOCATION: (7)..(7)
<223> OTHER INFORMATION: Ile or Val
<220> FEATURE:
<221> NAME/KEY: MISC_FEATURE
<222> LOCATION: (10)..(10)
<223> OTHER INFORMATION: any amino acid
<220> FEATURE:
<221> NAME/KEY: MISC_FEATURE
<222> LOCATION: (12)..(12)
<223> OTHER INFORMATION: any amino acid
<220> FEATURE:
<221> NAME/KEY: MISC_FEATURE

```
<222> LOCATION: (13)..(13)
<223> OTHER INFORMATION: any amino acid
<220> FEATURE:
<221> NAME/KEY: MISC_FEATURE
<222> LOCATION: (15)..(19)
<223> OTHER INFORMATION: any amino acid
<220> FEATURE:
<221> NAME/KEY: MISC_FEATURE
<222> LOCATION: (22)..(26)
<223> OTHER INFORMATION: any amino acid
<220> FEATURE:
<221> NAME/KEY: MISC_FEATURE
<222> LOCATION: (28)..(28)
<223> OTHER INFORMATION: any amino acid
<220> FEATURE:
<221> NAME/KEY: MISC_FEATURE
<222> LOCATION: (34)..(36)
<223> OTHER INFORMATION: any amino acid
<220> FEATURE:
<221> NAME/KEY: MISC_FEATURE
<222> LOCATION: (38)..(41)
<223> OTHER INFORMATION: any amino acid
<220> FEATURE:
<221> NAME/KEY: MISC_FEATURE
<222> LOCATION: (42)..(42)
<223> OTHER INFORMATION: Asn, Asp, Glu or Gln
<220> FEATURE:
<221> NAME/KEY: MISC_FEATURE
<222> LOCATION: (47)..(47)
<223> OTHER INFORMATION: Asn, Asp, Glu or Gln
<220> FEATURE:
<221> NAME/KEY: MISC_FEATURE
<222> LOCATION: (48)..(55)
<223> OTHER INFORMATION: any amino acid
<220> FEATURE:
<221> NAME/KEY: MISC_FEATURE
<222> LOCATION: (57)..(58)
<223> OTHER INFORMATION: any amino acid
<220> FEATURE:
<221> NAME/KEY: MISC_FEATURE
<222> LOCATION: (59)..(59)
<223> OTHER INFORMATION: Asn, Asp, Glu or Gln
<220> FEATURE:
<221> NAME/KEY: MISC_FEATURE
<222> LOCATION: (60)..(66)
<223> OTHER INFORMATION: any amino acid
<220> FEATURE:
<221> NAME/KEY: MISC_FEATURE
<222> LOCATION: (68)..(68)
<223> OTHER INFORMATION: Ile or Val
<220> FEATURE:
<221> NAME/KEY: MISC_FEATURE
<222> LOCATION: (69)..(72)
<223> OTHER INFORMATION: any amino acid
<220> FEATURE:
<221> NAME/KEY: MISC_FEATURE
<222> LOCATION: (74)..(75)
<223> OTHER INFORMATION: any amino acid
<220> FEATURE:
<221> NAME/KEY: MISC_FEATURE
<222> LOCATION: (77)..(77)
<223> OTHER INFORMATION: any amino acid
<220> FEATURE:
<221> NAME/KEY: MISC_FEATURE
<222> LOCATION: (79)..(81)
<223> OTHER INFORMATION: any amino acid
<220> FEATURE:
<221> NAME/KEY: MISC_FEATURE
<222> LOCATION: (83)..(83)
<223> OTHER INFORMATION: any amino acid
<220> FEATURE:
<221> NAME/KEY: MISC_FEATURE
<222> LOCATION: (85)..(87)
<223> OTHER INFORMATION: any amino acid
<220> FEATURE:
<221> NAME/KEY: MISC_FEATURE
<222> LOCATION: (89)..(91)
<223> OTHER INFORMATION: any amino acid
<220> FEATURE:
```

-continued

<221> NAME/KEY: MISC_FEATURE
<222> LOCATION: (93)..(98)
<223> OTHER INFORMATION: any amino acid
<220> FEATURE:
<221> NAME/KEY: MISC_FEATURE
<222> LOCATION: (103)..(103)
<223> OTHER INFORMATION: Phe or Tyr
<220> FEATURE:
<221> NAME/KEY: MISC_FEATURE
<222> LOCATION: (105)..(106)
<223> OTHER INFORMATION: any amino acid
<220> FEATURE:
<221> NAME/KEY: MISC_FEATURE
<222> LOCATION: (107)..(107)
<223> OTHER INFORMATION: Asn, Asp, Glu or Gln
<220> FEATURE:
<221> NAME/KEY: MISC_FEATURE
<222> LOCATION: (108)..(108)
<223> OTHER INFORMATION: any amino acid

<400> SEQUENCE: 13

```
Xaa Xaa Xaa Xaa Xaa Leu Xaa Ser Ile Xaa Ile Pro Xaa Tyr Asn Xaa
1               5                   10                  15

Xaa Xaa Xaa Tyr Leu Xaa Xaa Xaa Xaa Xaa Ser Xaa Leu Asn Gln Thr
            20                  25                  30

Tyr Xaa Xaa Xaa Glu Xaa Xaa Xaa Xaa Xaa Asp Gly Ser Thr Xaa Xaa
        35                  40                  45

Xaa Xaa Xaa Xaa Xaa Xaa Xaa Glu Xaa Xaa Xaa Xaa Xaa Xaa Xaa Xaa
    50                  55                  60

Xaa Xaa Arg Xaa Xaa Xaa Xaa Xaa Ser Xaa Xaa Asn Xaa Gly Xaa Xaa
65                  70                  75                  80

Xaa Ala Xaa Asn Xaa Xaa Xaa Glu Xaa Xaa Xaa Gly Xaa Xaa Xaa Xaa
                85                  90                  95

Xaa Xaa Asp Ser Asp Asp Xaa Ile Xaa Xaa Xaa Xaa
            100                 105
```

<210> SEQ ID NO 14
<211> LENGTH: 37
<212> TYPE: PRT
<213> ORGANISM: Pasteurella multocida

<400> SEQUENCE: 14

```
Phe Ala Ala Gly Asn Val Ala Phe Ala Lys Lys Trp Leu Asn Lys Ser
1               5                   10                  15

Gly Phe Phe Asp Glu Glu Phe Asn His Trp Gly Gly Glu Asp Val Glu
            20                  25                  30

Phe Gly Tyr Arg Leu
        35
```

<210> SEQ ID NO 15
<211> LENGTH: 37
<212> TYPE: PRT
<213> ORGANISM: Mus musculus

<400> SEQUENCE: 15

```
Phe Ala Gly Gly Leu Phe Ser Ile Ser Lys Lys Tyr Phe Glu His Ile
1               5                   10                  15

Gly Ser Tyr Asp Glu Glu Met Glu Ile Trp Gly Gly Glu Asn Ile Glu
            20                  25                  30

Met Ser Phe Arg Val
        35
```

<210> SEQ ID NO 16

```
<211> LENGTH: 37
<212> TYPE: PRT
<213> ORGANISM: Artificial sequence
<220> FEATURE:
<223> OTHER INFORMATION: Consensus sequence for alignment of SEQ ID NOS:
      14 and 15
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (5)..(9)
<223> OTHER INFORMATION: any amino acid
<220> FEATURE:
<221> NAME/KEY: MISC_FEATURE
<222> LOCATION: (12)..(13)
<223> OTHER INFORMATION: any amino acid
<220> FEATURE:
<221> NAME/KEY: MISC_FEATURE
<222> LOCATION: (14)..(14)
<223> OTHER INFORMATION: Asn, Asp, Glu or Gln
<220> FEATURE:
<221> NAME/KEY: MISC_FEATURE
<222> LOCATION: (15)..(16)
<223> OTHER INFORMATION: any amino acid
<220> FEATURE:
<221> NAME/KEY: MISC_FEATURE
<222> LOCATION: (18)..(18)
<223> OTHER INFORMATION: any amino acid
<220> FEATURE:
<221> NAME/KEY: MISC_FEATURE
<222> LOCATION: (19)..(19)
<223> OTHER INFORMATION: Phe or Tyr
<220> FEATURE:
<221> NAME/KEY: MISC_FEATURE
<222> LOCATION: (23)..(23)
<223> OTHER INFORMATION: any amino acid
<220> FEATURE:
<221> NAME/KEY: MISC_FEATURE
<222> LOCATION: (24)..(24)
<223> OTHER INFORMATION: Asn, Asp, Glu or Gln
<220> FEATURE:
<221> NAME/KEY: MISC_FEATURE
<222> LOCATION: (25)..(25)
<223> OTHER INFORMATION: any amino acid
<220> FEATURE:
<221> NAME/KEY: MISC_FEATURE
<222> LOCATION: (30)..(30)
<223> OTHER INFORMATION: Asn, Asp, Glu or Gln
<220> FEATURE:
<221> NAME/KEY: MISC_FEATURE
<222> LOCATION: (31)..(31)
<223> OTHER INFORMATION: Ile or Val
<220> FEATURE:
<221> NAME/KEY: MISC_FEATURE
<222> LOCATION: (33)..(34)
<223> OTHER INFORMATION: any amino acid
<220> FEATURE:
<221> NAME/KEY: MISC_FEATURE
<222> LOCATION: (35)..(35)
<223> OTHER INFORMATION: Phe or Tyr
<220> FEATURE:
<221> NAME/KEY: MISC_FEATURE
<222> LOCATION: (36)..(36)
<223> OTHER INFORMATION: any amino acid
<220> FEATURE:
<221> NAME/KEY: MISC_FEATURE
<222> LOCATION: (37)..(37)
<223> OTHER INFORMATION: any amino acid

<400> SEQUENCE: 16

Phe Ala Xaa Gly Xaa Xaa Xaa Xaa Xaa Lys Lys Xaa Xaa Xaa Xaa Xaa
1               5                   10                  15

Gly Xaa Xaa Asp Glu Glu Xaa Xaa Xaa Trp Gly Gly Glu Xaa Xaa Glu
            20                  25                  30
```

Xaa Xaa Xaa Arg Xaa
        35

<210> SEQ ID NO 17
<211> LENGTH: 703
<212> TYPE: PRT
<213> ORGANISM: Pasteurella multocida

<400> SEQUENCE: 17

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
    130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

```
Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
            435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
            500                 505                 510

Ala Ala Val Ser Phe Ala Lys Gly Tyr Tyr Ile Gly Gln Leu Asp Ser
        515                 520                 525

Asp Asp Tyr Leu Glu Pro Asp Ala Val Glu Leu Cys Leu Lys Glu Phe
    530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
        595                 600                 605

Glu Asn Ala Val Asp Tyr Asp Met Phe Leu Lys Leu Ser Glu Val Gly
    610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile
    690                 695                 700

<210> SEQ ID NO 18
<211> LENGTH: 4
<212> TYPE: PRT
<213> ORGANISM: Artificial Sequence
<220> FEATURE:
<223> OTHER INFORMATION: motif for HAS proteins
<220> FEATURE:
<221> NAME/KEY: MISC_FEATURE
<222> LOCATION: (4)..(4)
<223> OTHER INFORMATION: Ser or Thr

<400> SEQUENCE: 18

Asp Gly Ser Xaa
```

```
<210> SEQ ID NO 19
<211> LENGTH: 7
<212> TYPE: PRT
<213> ORGANISM: Artificial Sequence
<220> FEATURE:
<223> OTHER INFORMATION: Motif for HAS proteins
<220> FEATURE:
<221> NAME/KEY: MISC_FEATURE
<222> LOCATION: (1)..(1)
<223> OTHER INFORMATION: Ser or Gly
<220> FEATURE:
<221> NAME/KEY: MISC_FEATURE
<222> LOCATION: (5)..(6)
<223> OTHER INFORMATION: any amino acid

<400> SEQUENCE: 19

Xaa Gly Pro Leu Xaa Xaa Tyr
 1               5

<210> SEQ ID NO 20
<211> LENGTH: 8
<212> TYPE: PRT
<213> ORGANISM: Artificial Sequence
<220> FEATURE:
<223> OTHER INFORMATION: Motif for HAS proteins
<220> FEATURE:
<221> NAME/KEY: MISC_FEATURE
<222> LOCATION: (5)..(5)
<223> OTHER INFORMATION: any amino acid

<400> SEQUENCE: 20

Gly Asp Asp Arg Xaa Leu Thr Asn
 1               5

<210> SEQ ID NO 21
<211> LENGTH: 14
<212> TYPE: PRT
<213> ORGANISM: Artificial Sequence
<220> FEATURE:
<223> OTHER INFORMATION: motif for HAS proteins
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (11)..(11)
<223> OTHER INFORMATION: Tyr or Phe or Trp
<220> FEATURE:
<221> NAME/KEY: MISC_FEATURE
<222> LOCATION: (12)..(12)
<223> OTHER INFORMATION: Phe or Cys

<400> SEQUENCE: 21

Leu Xaa Gln Gln Xaa Arg Trp Xaa Lys Ser Xaa Xaa Arg Glu
 1               5                  10

<210> SEQ ID NO 22
<211> LENGTH: 25
<212> TYPE: DNA
<213> ORGANISM: Artificial Sequence
<220> FEATURE:
```

<223> OTHER INFORMATION: primer

<400> SEQUENCE: 22
gaccttgata aagtgtgata agtcc                                    25

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
gcgaattcaa aggacagaaa atgaacacat tatcacaag                     39

<210> SEQ ID NO 24
<211> LENGTH: 41
<212> TYPE: DNA
<213> ORGANISM: Artificial Sequence
<220> FEATURE:
<223> OTHER INFORMATION: primer

<400> SEQUENCE: 24
gggaattctg cagttataga gttatactat taataatgaa c                  41

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
ctccagctgt aaattagaga taaag                                    25

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
gcacatagaa taaggcttta cgagc                                    25

<210> SEQ ID NO 27
<211> LENGTH: 5
<212> TYPE: PRT
<213> ORGANISM: Artificial Sequence
<220> FEATURE:
<223> OTHER INFORMATION: motif for HAS proteins

<400> SEQUENCE: 27

Asp Gly Ser Thr Asp
1               5

<210> SEQ ID NO 28
<211> LENGTH: 4
<212> TYPE: PRT
<213> ORGANISM: Artificial Sequence
<220> FEATURE:
<223> OTHER INFORMATION: motif for HAS proteins

```
<220> FEATURE:
<221> NAME/KEY: MISC_FEATURE
<222> LOCATION: (2)..(2)
<223> OTHER INFORMATION: any amino acid

<400> SEQUENCE: 28

Asp Xaa Asp Asp
1
```

DNA ENCODING HYALURONAN SYNTHASE FROM *PASTEURELLA MULTOCIDA* AND METHODS OF USE

CROSS REFERENCE TO RELATED APPLICATIONS

This application is a continuation of U.S. Ser. No. 10/217,613, filed Aug. 12, 2002, now U.S. Pat. No. 6,987,023, issued Jan. 17, 2006; which is a continuation of U.S. Ser. No. 09/283,402, filed Apr. 1, 1999, now abandoned; which claims benefit under 35 U.S.C. 119(e) of U.S. Ser. No. 60/080,414, filed on Apr. 2, 1998; each of which is hereby expressly incorporated by reference herein in its entirety. Said application U.S. Ser. No. 10/217,613 is also a continuation-in-part of U.S. Ser. No. 09/178,851, filed Oct. 26, 1998, now abandoned; which is hereby expressly incorporated by reference herein in its entirety.

STATEMENT AS TO FEDERALLY SPONSORED RESEARCH

This application was supported in part by a National Research Initiative grant for Sustaining Animal Health and Well-Being 94-37204-0929 from the U.S. Department of Agriculture. The United States Government may have rights in and to this application by virtue of this funding.

BACKGROUND OF THE INVENTION

1. Field of the Invention

The present invention relates to a DNA sequence encoding hyaluronan synthase from *Pasteurella multocida*. More particularly, the present invention relates to a DNA sequence encoding hyaluronan synthase from *Pasteurella multocida* which is capable of being placed into a recombinant construct so as to be able to express hyaluronan synthase in a foreign host. The present invention also relates to methods of using a DNA sequence encoding hyaluronan synthase from *Pasteurella multocida* to (1) make hyaluronan polymers of varying size distribution; (2) make hyaluronan polymers incorporating substitute or additional base sugars; (3) develop new and novel animal vaccines; and (4) develop new and novel diagnostic tests for the detection and identification of animal pathogens.

2. Brief Description of the Background Art

The polysaccharide hyaluronic acid ("HA") or hyaluronan is an essential component of higher animals that serves both structural and recognition roles. In mammals and birds, HA is present in large quantities in the skin, the joint synovial fluid, and the vitreous humor of the eye. Certain pathogenic bacteria, namely, Gram-positive Group A and C *Streptococcus* and Gram-negative *Pasteurella multocida* Carter Type A, produce extracellular capsules containing HA with the same chemical structure as the HA molecule found in their vertebrate hosts. This "molecular mimicry" foils attempts to mount a strong antibody response to the capsular polysaccharide. In contrast, capsular polysaccharides with different structures produced by other bacteria are often quite antigenic. The HA capsule also apparently helps the pathogens evade host defenses including phagocytosis.

Historically, researchers in the field have not succeeded in cloning or identifying Hyaluronan Synthase ("HAS") from *Pasteurella*. Bacterial HAS enzymes from Group A & C *Streptococcus* have been identified and cloned. HasA from *Streptococcus pyogenes* was the first HAS to be definitively identified. This integral membrane protein utilizes intracellular UDP-GlcA and UDP-GlcNAc as substrates. The nascent HA chain is extruded through the membrane to form the extracellular capsule. A *Xenopus* protein, DG42, has also been determined to be a HAS. Several human and murine homologs of DG42, named HAS1, HAS2 and HAS3, have also been identified. There is considerable similarity among these molecularly cloned mammalian enzymes at the amino acid level, but they reside on different chromosomes. The unique HAS from *P. multocida* has a primary structure that does not strongly resemble the previously cloned enzymes from *Streptococcus*, PBCV-1 virus or higher animals.

A viral HAS, with an ORF called A98R, has been identified as being 28-30% identical to the streptococcal and vertebrate enzymes. PBCV-1 (*Paramecium bursaria* Chlorella virus) produces an authentic HA polysaccharide shortly after infection of its Chlorella-like green algae host. A98R is the first virally encoded enzyme identified as producing a carbohydrate polymer.

Carter type A *P. multocida*, the causative agent of fowl cholera, is responsible for great economic losses in the U.S. poultry industry. Acapsular mutants of *P. multocida* do not thrive in the bloodstream of turkeys after intravenous injection, where encapsulated parental strains multiply quickly and cause death within 1 to 2 days. Spontaneously arising mutant strain which is acapsular, was also $10^5$-fold less virulent than wild-type, but the nature of the genetic defects in all the cases before the disclosed mutant (as described hereinafter) was not known.

*Pasteurella* bacterial pathogens cause extensive losses to U.S. agriculture. The extracellular polysaccharide capsule of *P. multocida* has been proposed to be a major virulence factor. The Type A capsule is composed of a polysaccharide, namely HA, that is identical to the normal polysaccharide in the host's body and thus invisible to the immune system. This "molecular mimicry" also hinders host defenses such as phagocytosis and complement-mediated lysis. Furthermore, HA is not strongly immunogenic since the polymer is a normal component of the host body. The capsules of other bacteria that are composed of different polysaccharides, however, are usually major targets of the immune response. The antibodies generated against capsular polymers are often responsible for clearance of microorganisms and long-term immunity.

Knowing the factors responsible for a pathogen's virulence provides clues on how to defeat the disease intelligently and efficaciously. In Type A *P. multocida*, one of the virulence factors is the protective shield of nonimmunogenic HA, an almost insurmountable barrier for host defenses. A few strains do not appear to rely on the HA capsule for protection, but utilize other unknown factors to resist the host mechanisms. Alternatively, these strains may possess much smaller capsules that are not detected by classical tests.

For chickens and especially turkeys, fowl cholera can be devastating. A few to 1,000 cells of some encapsulated strains can kill a turkey in 24-48 hours. Fowl cholera is an economically important disease in North America. Studies done in the late 1980s show some of the effects of fowl cholera on the turkey industry: (i) fowl cholera causes 14.7 to 18% of all sickness, (ii) in one state alone the annual loss was $600,000, (iii) it costs $0.40/bird to treat a sick flock with antibiotics, and (iv) it costs $0.12/bird for treatment to prevent infection.

Certain strains of Type A *P. multocida* cause pneumonic lesions and shipping fever in cattle subjected to stress. The subsequent reduction in weight gain at the feedlot causes major losses. The bovine strains are somewhat distinct from fowl cholera strains, but the molecular basis for these differences in host range preference is not yet clear. Type A also causes half of the pneumonia in swine. Type D *P. multocida* is most well known for its involvement in atrophic rhinitis, a high priority disease in swine.

Type D capsular polymer has an unknown structure that appears to be some type of glycosaminoglycan; this is the same family of polymers that includes HA. This disease is also precipitated by *Bordetella bronchiseptica,* but the condition is worse when both bacterial species are present. It is estimated that Type F causes about 10% of the fowl cholera caes. In this case, the capsular polymer is not HA, but a related polymer called chondroitin.

Currently, disease prevention on the fowl range is mediated by two elements: vaccines and antibiotics, as well as strict sanitation. The utility of the first option is limited, since there are many serotypes in the field and vaccines are only effective against a limited subset of the entire pathogen spectrum. Killed-cell vaccine is dispensed by labor-intensive injection, and the protection obtained is not high. Therefore, this route is usually reserved for the breeder animals. More effective live-cell vaccines can be delivered via the water supply, but it is difficult to dose a flock of thousands evenly. Additionally, live "avirulent" vaccines can sometimes cause disease themselves if the birds are otherwise stressed or sick. The most common reason for this unpredictability is that these avirulent strains arose from spontaneous mutations in unknown or uncharacterized genes. Protocols that utilize repeated alternating exposure to live and dead vaccines can protect birds only against challenge with the same serotype.

The second disease prevention option is antibiotics. These are used at either subtherapeutic doses to prevent infection or at high doses to combat fowl cholera in infected birds. The percentage of birds with disease may drop with drug treatment, but timely and extensive treatment is necessary. Late doses or premature withdrawal of antibiotics often results in chronic fowl cholera and sickly birds with abscesses or lesions that lead to condemnation and lost sales. Furthermore, since resistant strains of *P. multocida* continually arise and drug costs are high, this solution is not attractive in the long run. In addition, Type F *P. multocida* may cause 5-10% of fowl cholera in North America. A vaccine directed against Type A strains may not fully protect against this other capsular type if it emerges as a major pathogen in the future. In the cattle and swine industries, no vaccine has been totally satisfactory. Prophylactic antibiotic treatment is used to avoid losses in weight gain, but this option is expensive and subject to the microbial resistance issue.

In the present invention, enzymes involved in making the protective bacterial HA capsule have been identified at the gene/DNA level. The identification of these enzymes will lead to disease intervention by blocking capsule synthesis of pathogens with specific inhibitors that spare host HA biosynthesis. For example, a drug mimicking the substrates used to make HA or a regulator of the *P. multocida* HA synthase stops production of the bacterial HA polysaccharide, and thus blocks capsule formation. This is a direct analogy to many current antibiotics that have dissimilar effects on microbial and host systems. This approach is preferred because the *P. multocida* HA synthase and the vertebrate HA synthase are very different at the protein level. Therefore, it is likely that the enzymes also differ in reaction mechanism or substrate binding sites.

*P. multocida,* once stripped of its protective capsule shield is significantly more vulnerable a target for host defenses. Phagocytes readily engulfed and destroyed by the acapsular microbes. The host complement complex reaches and disrupts the sensitive outer membrane of bacteria. Antibodies are more readily generated against the newly exposed immunogens, such as the lipopolysaccharides and surface proteins that determine somatic serotype in *P. multocida.* These antibodies are better able to bind to acapsular cells later in the immune response. Thus, the immune response from vaccinations are more effective and more cost-effective. Capsule-inhibiting drugs are substantial additions to the treatment of fowl cholera.

The present invention and use of the capsule biosynthesis of Type A *P. multocida* aids in the understanding of the other capsular serotypes. DNA probes have been used to type A capsule genes to establish that Type D and F possess similar homologs.

High molecular weight HA also has a wide variety of useful applications—ranging from cosmetics to eye surgery. Due to its potential for high viscosity and its high biocompatibility, HA finds particular application in eye surgery as a replacement for vitreous fluid. HA has also been used to treat racehorses for traumatic arthritis by intra-articular injections of HA, in shaving cream as a lubricant, and in a variety of cosmetic products due to its physiochemical properties of high viscosity and its ability to retain moisture for long periods of time. In fact, in August of 1997 the U.S. Food and Drug Agency approved the use of high molecular weight HA in the treatment of severe arthritis through the injection of such high molecular weight HA directly into the affected joints. In general, the higher molecular weight HA that is employed the better. This is because HA solution viscosity increases with the average molecular weight of the individual HA polymer molecules in the solution. Unfortunately, very high molecular weight HA, such as that ranging up to $10^7$, has been difficult to obtain by currently available isolation procedures.

To address these or other difficulties, there is a need for new methods and constructs that can be used to produce HA having one or more improved properties such as greater purity or ease of preparation. In particular, there is a need to develop methodology for the production of larger amounts of relatively high molecular weight and relatively pure HA than is currently commercially available. There is yet another need to be able to develop methodology for the production of HA having a modified size distribution ($HA_{\Delta size}$) as well as HA having a modified structure ($HA_{\Delta mod}$).

The present invention, therefore, functionally characterizes the Type A *P. multocida* genes involved in capsule biosynthesis, assesses the role of the capsule as a virulence factor in fowl cholera, and has obtained the homologous genes involved in Type D and F capsule biosynthesis. With this information, vaccines have been developed utilizing "knock out" *P. multocida* genes that do not produce HAS. These acapsular avirulent strains have the ability to act as vaccines for fowl cholera or shipping fever.

SUMMARY OF THE INVENTION

The present invention relates to a novel HAS that produces HA. Using various molecular biology techniques, a gene for a new HAS was found in fowl cholera pathogen Type A *Pasteurella multocida.* This new HAS from *Pasteurella multocida,* ("PmHAS"), was cloned and shown to be functional in other species of bacteria.

Thus, a new source of HA has been identified. The DNA sequence of PmHAS may also be used to generate potential attenuated vaccine strains of *P. multocida* bacteria after knocking out the normal microbial gene by homologous recombination with a disrupted version. Additionally, the PmHAS DNA sequence allows for the generation of diagnostic bacterial typing probes for related *P. multocida* types that are agricultural pathogens of fowl, cattle, sheep and swine.

BRIEF DESCRIPTION OF THE SEVERAL VIEWS OF THE DRAWINGS

FIG. 1 is a partial sequence alignment of PmHAS *P. multocida* and other glycosyltransferases from other bacteria.

FIG. 2 is a sequence alignment of residues 342-383 of PmHAS as compared to residues 362-404 of the mammalian UDP-GalNAc:polypeptide GalNAc-transferase.

FIG. 15 is a Southern blot analysis of various capsule types of *P. multocida* with Type A capsule gene probes.

FIG. 16 is an electrophoretogram of the PCR of the Type A DNA and heterologous DNA with various Type A primers.

FIG. 19 is the molecular biological confirmation of the acapsular knockout mutant by Southern blot and PCR analyses.

FIG. 20E is a sequence comparison of Type A and F *P. multocida*.

DETAILED DESCRIPTION OF THE INVENTION

Figure 3:
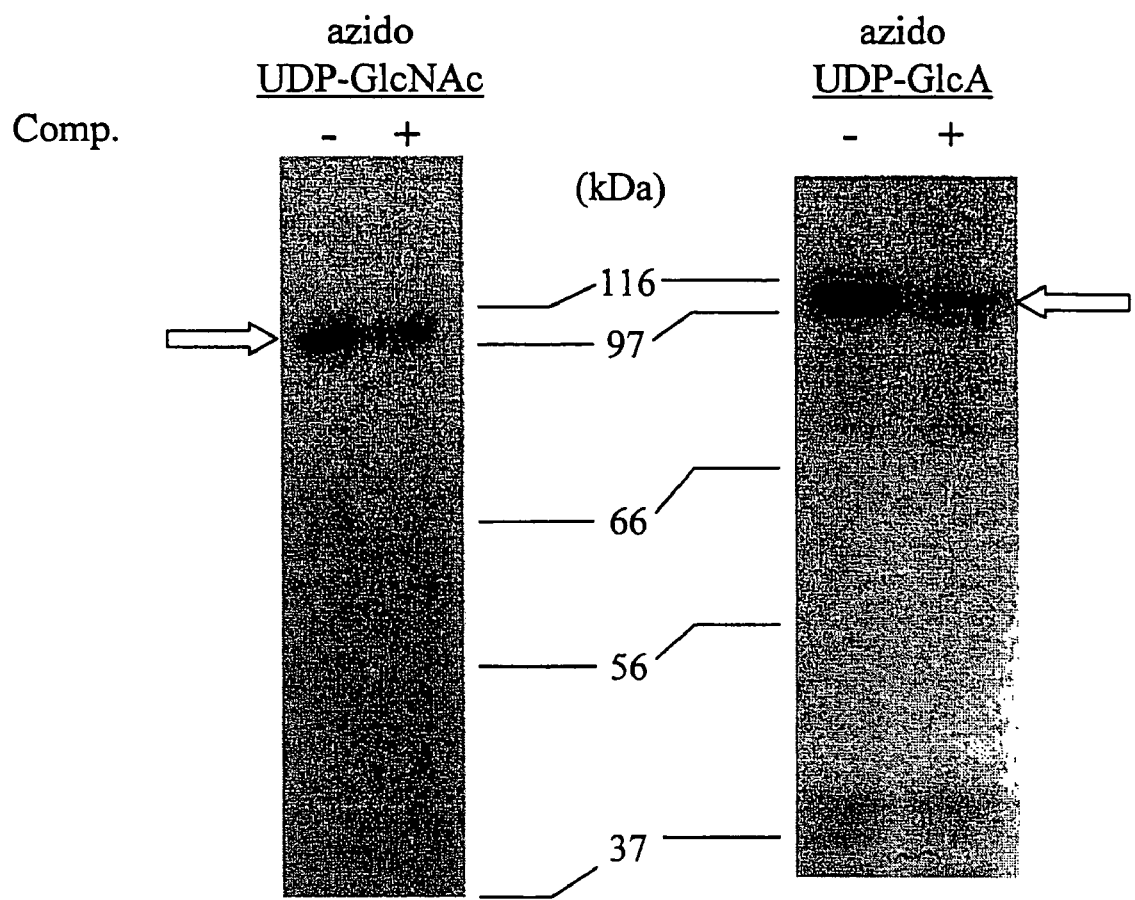
FIG. 3 is an autoradiogram representation of a photoaffinity labeling study with UDP-sugar analogs of PmHAS.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Hyaluronate Synthase ("HAS") coding sequence yet is isolated away from, or purified free from, unrelated genomic DNA, for example, total *Pasteurella multocida* or, for example, mammalian host genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified PmHAS gene refers to a DNA segment including HAS coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest, in this case PmHAS, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Due to certain advantages associated with the use of prokaryotic sources, one will likely realize the most advantages upon isolation of the HAS gene from the prokaryote *P. multocida*. One such advantage is that, typically, eukaryotic enzymes may require significant post-translational modifications that can only be achieved in a eukaryotic host. This will tend to limit the applicability of any eukaryotic HA synthase gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library, and (b) the ease of manipulation because the overall size of the coding region of a prokaryotic gene is significantly smaller due to the absence of introns. Furthermore, if the product of the PmHAS gene (i.e., the enzyme) requires posttranslational modifications, these would best be achieved in a similar prokaryotic cellular environment (host) from which the gene was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences which encode a PmHAS gene, that includes within its amino acid sequence an amino acid sequence in accordance with SEQ ID NO:1. Moreover, in other particular embodiments, the invention concerns isolated DNA segments and recombinant vectors incorporating DNA sequences which encode a gene that includes within its amino acid sequence the amino acid sequence of an HAS gene or DNA, and in particular to an HAS gene or cDNA, corresponding to *Pasteurella multocida* HAS. For example, where the DNA segment or vector encodes a full length HAS protein, or is intended for use in expressing the HAS protein, preferred sequences are those which are essentially as set forth in SEQ ID NO:1

Truncated PmHAS also falls within the definition of preferred sequences as set forth in SEQ ID NO:1. For instance, at the c terminus, approximately 270-272 amino acids may be removed from the sequence and still have a functioning HAS (SEQ ID NO:17). Those of ordinary skill in the art would appreciate that simple amino acid removal from either end of the PmHAS sequence can be accomplished. The truncated versions of the sequence simply have to be checked for HAS activity in order to determine if such a truncated sequence is still capable of producing HAS.

Nucleic acid segments having HA synthase activity may be isolated by the methods described herein. The term "a sequence essentially as set forth in SEQ ID NO:1 means that the sequence substantially corresponds to a portion of SEQ ID NO:1 and has relatively few amino acids which are not identical to, or a biologically functional equivalent of, the amino acids of SEQ ID NO:1. The term "biologically functional equivalent" is well understood in the art and is further defined in detail herein, as a gene having a sequence essentially as set forth in SEQ ID NO:1, and that is associated with the ability of prokaryotes to produce HA or a hyaluronic acid coat.

The art is replete with examples of practitioners ability to make structural changes to a nucleic acid segment (i.e., encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1019-1029 (1988) [" . . . according to the observed exchangeability of amino acid side chains, only four groups could be delineated; (i) Ile and Val; (ii) Leu and Met, (iii) Lys, Arg, and Gln, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481-497 (1991) [similarity parameters allow amino acid substitutions to be designed]; and, (3) Overington et al. "Environment-Specific Amino Acid Substitution Tables: Tertiary Templates and Prediction of Protein Folds," Protein Science 1:216-226 (1992) ["Analysis of the pattern of observed substitutions as a function of local environment shows that there are distinct patterns . . . " Compatible changes can be made.]

These references and countless others, indicate that one of ordinary skill in the art, given a nucleic acid sequence, could make substitutions and changes to the nucleic acid sequence without changing its functionality. Also, a substituted nucleic acid segment may be highly identical and retain its enzymatic activity with regard to its unadulterated parent, and yet still fail to hybridize thereto.

The invention discloses nucleic acid segments encoding an enzymatically active hyaluronate synthase from *P. multocida*—PmHAS. One of ordinary skill in the art would appreciate that substitutions can be made to the PmHAS nucleic acid segment listed in SEQ ID NO:2 without deviating outside the scope and claims of the present invention. Standardized and accepted functionally equivalent amino acid substitutions are presented in Table A.

TABLE A

| Amino Acid Group | Conservative and Semi-Conservative Substitutions |
| --- | --- |
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Another preferred embodiment of the present invention is a purified nucleic acid segment that encodes a protein in accordance with SEQ ID NO:1, further defined as a recombinant vector. As used herein, the term "recombinant vector" refers to a vector that has been modified to contain a nucleic acid segment that encodes an HAS protein, or fragment thereof. The recombinant vector may be further defined as an expression vector comprising a promoter operatively linked to said HAS encoding nucleic acid segment.

A further preferred embodiment of the present invention is a host cell, made recombinant with a recombinant vector comprising an HAS gene. The preferred recombinant host cell may be a prokaryotic cell. In another embodiment, the recombinant host cell is a eukaryotic cell. As used herein, the term "engineered" or "recombinant" cell is intended to refer to a cell into which a recombinant gene, such as a gene encoding HAS, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene.

In preferred embodiments, the HA synthase-encoding DNA segments further include DNA sequences, known in the art functionally as origins of replication or "replicons", which allow replication of contiguous sequences by the particular host. Such origins allow the preparation of extrachromosomally localized and replicating chimeric segments or plasmids, to which HA synthase DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HA synthase coding gene sequence together with an appropriate replication origin and under the control of selected control regions.

Thus, it will be appreciated by those of skill in the art that other means may be used to obtain the HAS gene or cDNA, in light of the present disclosure. For example, polymerase chain reaction or RT-PCR produced DNA fragments may be obtained which contain full complements of genes or cDNAs from a number of sources, including other strains of *Pasteurellas* or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HA synthase.

Once the DNA has been isolated it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both *Lactococcus* or *Bacillus* strains and *E. coli* are employed.

Vectors such as these, exemplified by the pSA3 vector of Dao and Ferretti or the pAT19 vector of Trieu-Cuot, et al., allow one to perform clonal colony selection in an easily manipulated host such as *E. coli,* followed by subsequent transfer back into a food grade *Lactococcus* or *Bacillus* strain for production of HA. These are benign and well studied organisms used in the production of certain foods and biotechnology products. These are advantageous in that one can augment the *Lactococcus* or *Bacillus* strain's ability to synthesize HA through gene dosaging (i.e., providing extra copies of the HA synthase gene by amplification) and/or inclusion of additional genes to increase the availability of HA precursors. The inherent ability of a bacterium to synthesize HA can also be augmented through the formation of extra copies, or amplification, of the plasmid that carries the HA synthase gene. This amplification can account for up to a 10-fold increase in plasmid copy number and, therefore, the HA synthase gene copy number.

Another procedure that would further augment HA synthase gene copy number is the insertion of multiple copies of the gene into the plasmid. Another technique would include integrating the HAS gene into chromosomal DNA. This extra amplification would be especially feasible, since the bacterial HA synthase gene size is small. In some scenarios, the chromosomal DNA-ligated vector is employed to transfect the host that is selected for clonal screening purposes such as *E. coli,* through the use of a vector that is capable of expressing the inserted DNA in the chosen host.

In certain other embodiments, the invention concerns isolated DNA segments and recombinant vectors that include within their sequence a nucleic acid sequence essentially as set forth in SEQ ID NO:2 The term "essentially as set forth in SEQ ID NO:2 is used in the same sense as described above and means that the nucleic acid sequence substantially corresponds to a portion of SEQ ID NO:2 and has relatively few codons which are not identical, or functionally equivalent, to the codons of SEQ ID NO:2 The term "functionally equivalent codon" is used herein to refer to codons that encode the same amino acid, such as the six codons for arginine or serine, as set forth in Table A, and also refers to codons that encode biologically equivalent amino acids.

It will also be understood that amino acid and nucleic acid sequences may include additional residues, such as additional N- or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzyme activity is concerned. The addition of terminal sequences particularly applies to nucleic acid sequences which may, for example, include various non-coding sequences flanking either of the 5' or 3' portions of the coding region or may include various internal sequences, which are known to occur within genes. Furthermore, residues may be removed from the N or C terminal amino acids and yet still be essentially as set forth in one of the sequences disclosed herein, so long as the sequence meets the criteria set forth above, as well.

Allowing for the degeneracy of the genetic code as well as conserved and semi-conserved substitutions, sequences which have between about 40% and about 80%; or more preferably, between about 80% and about 90%; or even more preferably, between about 90% and about 99%; of nucleotides which are identical to the nucleotides of SEQ ID NO:2 will be sequences which are "essentially as set forth in SEQ ID NO:2". Sequences which are essentially the same as those set forth in SEQ ID NO:2 may also be functionally defined as sequences which are capable of hybridizing to a nucleic acid segment containing the complement of SEQ ID NO:2 under standard or less stringent hybridizing conditions. Suitable standard hybridization conditions will be well known to those of skill in the art and are clearly set forth herein.

The term "standard hybridization conditions" as used herein, is used to describe those conditions under which substantially complementary nucleic acid segments will form standard Watson-Crick base-pairing. A number of factors are known that determine the specificity of binding or hybridization, such as pH, temperature, salt concentration, the presence of agents, such as formamide and dimethyl sulfoxide, the length of the segments that are hybridizing, and the like. When it is contemplated that shorter nucleic acid segments will be used for hybridization, for example fragments between about 14 and about 100 nucleotides, salt and temperature preferred conditions for hybridization will include 1.2-1.8×High Phosphate Buffer (HPB) at 40-50° C.

Naturally, the present invention also encompasses DNA segments which are complementary, or essentially complementary, to the sequence set forth in SEQ ID NO:2. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:2.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular amino acid and nucleic acid sequences of SEQ ID NO:1 and 2. Recombinant vectors and isolated DNA segments may therefore variously include the HAS coding regions themselves, coding regions bearing selected alterations or modifications in the basic coding region, or they may encode larger polypeptides which nevertheless include HAS-coding regions or may encode biologically functional equivalent proteins or peptides which have variant amino acids sequences.

The DNA segments of the present invention encompass biologically functional equivalent HAS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HAS protein or to test HAS mutants in order to examine HA synthase activity at the molecular level.

Also, specific changes to the HAS coding sequence can result in the production of HA having a modified size distribution or structural configuration. One of ordinary skill in the art would appreciate that the HAS coding sequence can be manipulated in a manner to produce an altered hyaluronate synthase which in turn is capable of producing hyaluronic acid having differing polymer sizes and/or functional capabilities. For example, the HAS coding sequence may be altered in such a manner that the hyaluronate synthase has an altered sugar substrate specificity so that the hyaluronate synthase creates a new hyaluronic acid-like polymer incorporating a different structure such as a previously unincorporated sugar or sugar derivative. This newly incorporated sugar could result in a modified hyaluronic acid having different functional properties, a hyaluronic acid having a smaller or larger polymer size/molecular weight, or both. As will be appreciated by one of ordinary skill in the art given the HAS coding sequences, changes and/or substitutions can be made to the HAS coding sequence such that these desired property and/or size modifications can be accomplished.

The term "modified structure" as used herein denotes a hyaluronic acid polymer containing a sugar or derivative not normally found in the naturally occurring HA polysaccharide. The term "modified size distribution" refer to the synthesis of hyaluronic acid molecules of a size distribution not normally found with the native enzyme; the engineered size could be much smaller or larger than normal.

Various hyaluronic acid products of differing size have application in the areas of drug delivery and the generation of an enzyme of altered structure can be combined with a hyaluronic acid of differing size. Applications in angiogenesis and wound healing are potentially large if hyaluronic acid polymers of about 20 monosaccharides can be made in good quantities. Another particular application for small hyaluronic acid oligosaccharides is in the stabilization of recombinant human proteins used for medical purposes. A major problem with such proteins is their clearance from the blood and a short biological half life. One present solution to this problem is to couple a small molecule shield that prevents the protein from being cleared from the circulation too rapidly. Very small molecular weight hyaluronic acid is well suited for this role and would be nonimmunogenic and biocompatible. Larger molecular weight hyaluronic acid attached to a drug or protein may be used to target the reticuloendothelial cell system which has endocytic receptors for hyaluronic acid.

One of ordinary skill in the art given this disclosure would appreciate that there are several ways in which the size distribution of the hyaluronic acid polymer made by the hyaluronate synthase could be regulated to give different sizes. First, the kinetic control of product size can be altered by decreasing temperature, decreasing time of enzyme action and by decreasing the concentration of one or both sugar nucleotide substrates. Decreasing any or all of these variables will give lower amounts and smaller sizes of hyaluronic acid product. The disadvantages of these approaches are that the yield of product will also be decreased and it may be difficult to achieve reproducibility from day to day or batch to batch.

Secondly, the alteration of the intrinsic ability of the enzyme to synthesize a large hyaluronic acid product. Changes to the protein can be engineered by recombinant DNA technology, including substitution, deletion and addition of specific amino acids (or even the introduction of prosthetic groups through metabolic processing). Such changes that result in an intrinsically slower enzyme could then allow more reproducible control of hyaluronic acid size by kinetic means. The final hyaluronic acid size distribution is determined by certain characteristics of the enzyme, that rely on particular amino acids in the sequence. Among the 20% of residues absolutely conserved between the streptococcal enzymes and the eukaryotic hyaluronate synthases, there is a set of amino acids at unique positions that control or greatly influence the size of the hyaluronic acid polymer that the enzyme can make. Specific changes in any of these residues can produce a modified HAS that produces an HA product having a modified size distribution. Engineered changes to seHAS, spHAS, pmHAS, or cvHAS that decrease the intrinsic size of the hyaluronic acid that the enzyme can make before the hyaluronic acid is released, will provide powerful means to produce hyaluronic acid product of smaller or potentially larger size than the native enzyme.

Finally, larger molecular weight hyaluronic acid made be degraded with specific hyaluronidases to make lower molecular weight hyaluronic acid. This practice, however, is very difficult to achieve reproducibility and one must meticulously repurify the hyaluronic acid to remove the hyaluronidase and unwanted digestion products.

Structurally modified hyaluronic acid is no different conceptually than altering the size distribution of the hyaluronic acid product by changing particular amino acids in the desired HAS or the spHAS. Derivatives of UDP-GlcNAc, in which the N-acetyl group is missing (UDP-GlcN) or replaced with another chemically useful group, are expected to be particularly useful. The strong substrate specificity must rely on a particular subset of amino acids among the 20% that are conserved. Specific changes to one or more of these residues creates a functional synthase that interacts less specifically with one or more of the substrates than the native enzyme. This altered enzyme could then utilize alternate natural or special sugar nucleotides to incorporate sugar derivatives designed to allow different chemistries to be employed for the following purposes: (i) covalently coupling specific drugs, proteins, or toxins to the structurally modified hyaluronic acid for general or targeted drug delivery, radiological procedures, etc. (ii) covalently cross linking the hyaluronic acid itself or to other supports to achieve a gel, or other three dimensional biomaterial with stronger physical properties, and (iii) covalently linking hyaluronic acid to a surface to create a biocompatible film or monolayer.

The present invention relates to a novel HAS that produces HA. Using various molecular biology techniques, a gene for a new HAS was found in fowl cholera pathogen Type A *Pasteurella multocida*. This new HAS from *Pasteurella multocida*, or PmHAS, has been cloned and shown to be functional in other species of bacteria. The PmHAS protein polymerizes authentic HA polysaccharide.

The carbohydrate produced by a recombinant *E. coli* transformed with PmHAS is recognized by the cartilage HA-binding protein and is sensitive to HA lyase digestion. Both of these reagents are regarded by those of ordinary skill in the art as being specific for HA polysaccharide. Also, both UDP-GlcA and UDP-GlcNAc were required for HA synthesis in vitro. Azido-UDP-GlcA and azido-UDP-GlcNAc, but not azido-UDP-Glc, specifically photoincorporated into PmHAS. As in the case of streptococcal HasA and *Xenopus* DG42, it appears that one polypeptide species, PmHAS, transfers two distinct sugar groups to the nascent HA chain.

Many encapsulated Gram-negative bacteria, including *E. coli, Neisseria meningitidis,* and *Hemophilus influenzae,* possess clusters of genes responsible for capsule biosynthesis organized in operons. These operons often contain genes encoding (i) enzymes required for sugar nucleotide precursor synthesis, (ii) glycosyltransferases for polymerizing the exopolysaccharide, and (iii) proteins implicated in polysaccharide export. The Type A *P. multocida* HA capsule operon contains (i) a KfaA analog, (ii) a HA synthase, and (iii) a putative UDP-Glc dehydrogenase. The Tn916 elements in the *P. multocida* acapsular mutants H and L were not integrated directly in the HAS gene but rather were located in the KfaA homolog gene.

As the PmHAS exists in a locus of at least several genes essential for making polysaccharide, a lesion or defect in any one of the capsule genes could affect HA production and capsule formation in *Pasteurella*. Thus, by disrupting an adjacent gene a vaccine could also be made. For example, if UDP-Glc dehydrogenase is removed or disrupted, no precursor sugar for HA synthase is available and HA cannot be made. Also, if Kfa or another transport associated gene is killed, then no surface HA is made by the microbe. Thus, the product of HA synthase in the natural *Pasteurella* microbe, i.e., an HA capsule, could be stopped by (a) disrupting precursor formation, or (b) disrupting the polymerization machinery, or (c) disrupting the transport machinery.

At the amino acid level, PmHAS is not as similar to the other cloned HASs as one of ordinary skill in the art would expect. Two potential short motifs, DGS(S/T) (SEQ ID NO:18) at residues 477-480 and DSD at residues 527-529 of PmHAS are present in HasA. Another similar DGS-containing motif is found repeated at residues 196-198 of PmHAS. The DG of the first motif and the DSD are conserved in all HASs. However, several absolutely conserved motifs ((S/G)GPLXXY (SEQ ID NO:19), GDDRXLTN (SEQ ID NO:20), and LXQQXRWXKS(Y/F/W)(F/C)RE) (SEQ ID NO:21) found in all previously cloned HASs are absent from PmHAS. Instead, a variety of bacterial glycosyltransferases align more closely with the sequence in the central portion of the *P. multocida* HAS protein. These enzymes, which have been either shown or predicted to transfer GlcNAc, galactose, or GalNAc groups, are roughly one-third the size of the PmHAS and their amino acid termini sequences align together with the middle of the PmHAS polypeptide, residues 430-540.

Sections of the first 420 residues of PmHAS show some similarity to portions of the mammalian UDP-GalNAc:polypeptide GalNAc-transferase. These observations may be a reflection of a possible domain structure within PmHAS. The last approximate 340 residues of the PmHAS are not significantly similar to other entries in the sequence data bases. Therefore, the *P. multocida* HAS is unique and is most likely the prototype of an entire new class of HAS.

PmHAS is roughly twice the size of the streptococcal, viral, or vertebrate HASs—972 versus 417-588 residues, respectively. Furthermore, the hydropathy plots of PmHAS and the other known HASs are dissimilar. Utilizing the TMPRED program, which is readily known and available to those of ordinary skill in the art on the World Wide Web, PmHAS is predicted to have only two candidate transmembrane helices (centered on residues 170 and 510), and both termini of the protein may be located in the cytoplasm. Topologically, these assumptions imply that one-third of the *P. multocida* polypeptide (approximately 340 residues) is located outside of the cytoplasm. On the other hand, a different topology is predicted for the other classes of HAS.

Reporter enzyme fusion analysis of streptococcal HAS confirms that a different topological arrangement exists in this enzyme consisting of (i) two transmembrane helices near the amino acid terminus, (ii) a putative cytoplasmic domain, followed by (iii) three membrane-associated regions at the carboxyl half of the protein. The connecting loops between membrane-associated regions are rather short (4-10 residues); therefore, the vast majority of the polypeptide chain is probably not extracellularly exposed.

The following detailed experimental steps and discussion of results, confirms that the present invention relates to a novel and unique PmHAS.

1. Molecular Cloning of PmHAS

Tn916 insertional mutagenesis and probe generation was first completed. Tn916 was used to disrupt and to tag the *P. multocida* HA biosynthesis locus. The Tn element on a nonreplicating plasmid, pAM150 was introduced into a wild-type encapsulated *P. multocida* strain (ATCC number 15742) by electroporation. Altered colony morphology was initially screened by visual examination with oblique lighting. The Wild-type strain forms large mucoid ("wet" appearance) colonies that appear iridescent (red and green coloration). Smaller, "drier" colonies lacking iridescence were chosen and streaked out. India ink staining and light microscopy were used as a secondary screen to assess the state of encapsulation. The position of the Tn elements in the mutant chromosome was mapped by Southern analysis.

The DNA sequences at the Tn-disrupted sites from several independently selected mutants were obtained by direct dideoxy sequence analysis of tagged chromosomal DNA. Briefly, a chimeric DNA fragment consisting of a 12-kb portion of the Tn916 element and a short region of the *P. multocida* DNA generated by HhaI digestion of mutant chromosomal DNA was purified by agarose gel electrophoresis (all of the wild type HhaI genomic fragments are less than or equal to 7 kb). The chimeric fragment served as the template in cycle sequencing reactions using $^{33}$P terminators and a Tn916 right arm terminus primer (5'-GACCTTGATAAAGTGTGATAAGTCC-3') (SEQ ID NO:22). The sequence data were used to design PCR primers. Gel-purified PCR products were labeled with digoxigenin utilizing the High Prime system manufactured by Boehringer Mannheim and well known to those of ordinary skill in the art.

The next step was the isolation of a functional HAS locus. A λ library of Sau3A partially digested wild type DNA was made using BamHI-cleaved λZap Express vector system produced by Stratagene. The plaque lifts were screened by hybridization with digoxigenin-labeled PCR product. *Escherichia coli* XLI-Blue MRF' was co-infected with individual purified positive λ clones and ExAssist helper phage to yield phagemids. The resulting phagemids were transfected into *E. coli* XLOLR cells to recover the plasmids.

The plasmids were transformed into a host more suitable for HA polysaccharide production, *E. coli* K5 (strain Bi8337-41). This strain produces UDP-GlcA, a required substrate for HA biosynthesis that is not found at significant levels in most laboratory strains. Additionally, K5 possesses many other genes essential for capsular polysaccharide transport in *E. coli*. Another host employed for expression studies was *E. coli* EV5, an acapsular derivative of a K1 strain which produces a polysialic acid capsule and which also possesses all the same general capsular polysaccharide transport machinery as K5, but does not have high levels of UDP-Glc dehydrogenase.

Cultures of the *E. coli* transformants with the candidate plasmids grown in completely defined medium were tested for HA polysaccharide production as described previously except that the cell pellets were extracted with 8 M urea, 0.01% SDS at 95 degrees Celsius for 2 minutes. The HA test assay produced by Pharmacia Biotech Inc., which is well known by those of ordinary skill in the art, employs a specific HA-binding protein to detect HA at concentrations greater than or equal to 0.1 μg/ml. Multiple determinations of HA levels were averaged. The HA concentration in bacterial cultures was normalized for differences in cell number by measuring the $A_{600}$ value and presenting the data as μg HA/ml/$A_{600}$ of bacteria. One plasmid, pPm7A, with a 5.8 kb insert conferred *E. coli* K5 with the ability to produce HA; no HA was produced by cells with vector plasmid alone. A truncated derivative of pPm7A containing an approximately 3.3 kb insert, called pPmΔ6e, could direct the biosynthesis of HA when transformed into *E. coli* K5. Therefore, the sequence of both strands of the pPm7A plasmid corresponding to the pPmΔ6e DNA was determined. A single complete 972-residue ORF, which we called PmHAS, was found and is shown in SEQ ID NO:1. The corresponding nucleotide sequence is shown in SEQ ID NO:2.

Expression of recombinant *P. multocida* HAS was then undertaken. The PmHAS ORF in the pPm7A insert was amplified by 13 cycles of PCR with Taq polymerase and primers corresponding to the sequence near the deduced amino and carboxyl termini (codons in capital letters: sense, 5'-gcgaattcaaaggacagaaaATGAAcACATTATCACAAG-3' (SEQ ID NO:23), and antisense, 5'-gggaattctgcagttaTAG-AGTTATACTATTAATAATGAAC-3' (SEQ ID NO:24); start and stop codons, respectively, in bold). Codon 2 (T->C) was altered (italic lowercase letter) to increase protein production in *E. coli*. The primers also contained EcoRI and PstI restriction sites (underlined letters) to facilitate cloning into the expression plasmid pKK223-3 (tac promoter; Pharmacia). The resulting recombinant construct, pPmHAS, was transformed into *E. coli* SURE cells (Stratagene) and this strain was used as the source of membrane preparations for in vitro HAS assays. Log phase cultures(LB broth, 30 degrees Celsius) were induced with 0.5 mM isopropylthiogalactoside for 3 hours before harvest. The plasmid was also transformed into *E. coli* K5; the resulting strain was examined for the presence of capsule by light microscopy and buoyant density centrifugation. The K5 bacterial cultures were not induced routinely because isopropylthiogalactopyranoside addition did not increase HA levels in LB or defined medium significantly.

Photoaffinity labeling of the native *P. multocida* HAS was then undertaken. The radiolabeled UDP sugar analogs, [$^{32}$P]azido-UDP-GlcA (3 mCi/μMol) and [$^{32}$P]azido-UDP-GlcNAc (2.5 mCi/μMol), were prepared and purified as described in the literature and known to one of ordinary skill in the art. Membrane preparations from *P. multocida* wild type in 50 mM Tris, 20 mM $MgCl_2$, pH 7, were incubated with either probe (final concentration, 20 μM) for 30 seconds on ice before irradiation with ultraviolet light (254 nm, 90 seconds). The proteins were precipitated with 5% trichloroacetic acid before SDS-polyacrylamide gel electrophoresis analysis. No radiolabel was incorporated if the irradiation step was omitted. As a specificity control, 10-fold molar excess of the normal UDP sugar was co-incubated with the probe and membranes. [$^{32}$P]azido-UDP-Glc (3 mCi/μMol) was also used as another control.

Approximately $8\times10^4$ Tn-containing transformants produced by several rounds of mutagenesis were screened for differences in colony morphology. By light spectroscopy with India Ink, the cells from small noniridescent colonies (n=4) possessed no detectable capsule (acapsular), whereas the cells from medium-sized iridescent colonies (n=8) appeared to have a capsule of about 10-25% of the diameter of the wild type (microcapsular). Two of the acapsular mutants, named H and L, which had Tn elements that mapped to the same HindIII or BstXI genomic fragments reverted to wild-type colony morphology at rates of approximately $10^{-3}$. The Tn element in each revertant had excised from the original position and reinserted at different, new locations as judged by Southern analysis; on the other hand, all acapsular subclones retained the Tn element at the original location. No significant HAS activity was detected in membrane preparations from mutant H cells, whereas substantial HAS activity was obtained from wild-type wild type cells (less than or equal to 0.7 versus 120 pmol transfer GlcA/mg protein/h, respectively). These findings suggest that the Tn elements in mutants H and L were indeed responsible for disrupting the HA biosynthesis locus.

In order to bridge the gap between the Tn insertion sites of two acapsular mutants, PCR using the mutant L chromosomal DNA template was performed with a primer derived from sequence at the mutant H disruption site, PmHF (5'-CTCCAGCTGTAAATTAGAGATAAAG-3') (SEQ ID NO:25), and a primer corresponding to the left terminus of Tn916, TnL2 (5'-GCACATAGAATAAGGCTTTACGAGC-3') (SEQ ID NO:26). A specific approximately 1 kb PCR product was obtained; alternatively, no product was formed if PmHR (inverse complement of PmHF) or the Tn916 right arm primer were substituted. The PCR product was used as a hybridization probe to obtain a functional copy of the *P. multocida* HAS.

Six positively hybridizing plaques were found after screening approximately $10^4$ plaques, and these phage were converted into plasmids. One plasmid, pPm7A, was found that could direct *E. coli* K5 to produce HA in vivo (20 μg HA/ml/$A_{600}$ of bacteria). *E. coli* K5 with control plasmids did not produce HA (less than or equal to 0.05 μg HA/ml/$A_{600}$). *E. coli* XLOLR or *E. coli* EV5 cells (which lack UDP-Glc dehydrogenase activity) do not produce HA even if they contain the pPm7A plasmid (less than or equal to 0.05 μg HA/ml/$A_{600}$). This genetic evidence implies that the insert of pPm7A does not encode a functional UDP-Glc dehydrogenase enzyme.

A truncated derivative of the pPm7A plasmid with the smallest insert capable of directing HA biosynthesis (85 μg HA/ml/$A_{600}$ of K5 bacteria), pPmΔ6e, contained a single complete ORF (SEQ ID NO:2) encoding a 972 residue protein as shown in SEQ ID NO:1. No obvious promoter is present in SEQ ID NO:2, but there is a predicted ribosome binding site labeled in bold "centered on nucleotides −10 to −7 and the two putative transmembrane regions predicted by TMPRED are underlined (Residues 162-182, and 503-522). The PmHAS of SEQ ID NO:1 is twice as large as streptococcal HasA. This protein is the HA synthase from *P. multocida*, PmHAS. The predicted $M_r$ is 111,923 and the calculated isoelectric point is 6.84. SEQ ID NO:2 is the nucleotide sequence for PmHAS.

This PmHAS was used as the query in BLASTP searches of the protein sequence data base. The central portion of PmHAS (residues 436-536) is most homologous to bacterial glycosyltransferases from a wide variety of genera, including *Streptococcus*, *Vibrio*, *Neisseria*, and *Staphylococcus*, that form exopolysaccharides or the carbohydrate portions of lipopolysaccharides (smallest sum probabilities, $10^{-22}$-$10^{-10}$, as shown in FIG. 1. FIG. 1 graphically depicts the sequence alignment of *P. multocida* HAS and other glycosyltransferases. The MULTALIN alignment illustrates that the central region of the PmHAS (residues 436-536) is most similar to the amino-terminal portions of various enzymes that produce other exopolysaccharides (*Streptococcus thermophilus* EpsI; Type 14 *S. pneumoniae* Cps14J) or the carbohydrate moiety of lipopolysaccharides (*H. Influenzae* LgtD homology). Only a few of the possible examples are shown in FIG. 1. *S. pyogenes* HasA (residues 61-168) has limited similarity to this depicted region of PmHAS.

The most notable sequence similarities are the DGSTD (SEQ ID NO:27) and DXDD (SEQ ID NO:28) motifs. Unexpectedly, there was no significant overall similarity of PmHAS to the streptococcal, viral, or vertebrate HASs with HASA having the smallest sum probability of 0.33. Only one short region of streptococcal HasA aligns with PmHAS in a convincing manner and is shown in FIG. 1.

A few segments of the first half of PmHAS are also similar to portions of the mammalian UDP-GalNAc: polypeptide GalNAc-transferase, an enzyme that initiates O-glycosylation of mucin-type proteins with the smallest sum probability being approximately $10^{-3}$, FIG. 2. As shown in FIG. 2, the sequence alignment of residues 342-383 of PmHAS are most similar to residues 362-404 of the mammalian UDP-GalNAc:polypeptide GalNAc-transferase. For both FIGS. 1 and 2, the identical residues are bold and underlined, and the consensus symbols are: !, either I or V; #, any one of N, D, E, or Q; %, either F or Y. The clusters of acidic residues are well conserved throughout the sequences.

The partial ORF (27 residues) downstream of PmHAS is very similar to the amino terminus of several UDP-Glc dehydrogenases from bacteria including *E. coli*, *Salmonella typhimurium*, and *Streptococcus pneumoniae* (67-74% identity). The severe truncation in the original pPm7A clone would be expected to result in complete loss of dehydrogenase activity. The other ORF (623 residues) upstream of PmHAS is very homologous to the *E. coli* K5 KfaA protein with a smallest sum probability of $10^{-52}$, a protein putatively involved in the transport of capsular polysaccharide out of the cell.

The predicted size of 972 residues (112 kDa) for PmHAS was confirmed by photoaffinity labeling of membrane preparations from *P. multocida* wild type. Both [$^{32}$P]azido-UDP-GlcA and [$^{32}$P]azido-UDP-GlcNAc probes photoincorporated into an approximately 110 kDa protein in an UV-dependent manner. FIG. 3 is a photoaffinity labeling of the PmHAS with UDP-sugar analogs. [$^{32}$P]azido-UDP-GlcA and [$^{32}$P]azido-UDP-GlcNAc were incubated with membrane preparations (45 μg of protein) isolated from wild-type *P. multocida* and irradiated with UV light. Autoradiograms (5 day exposures) of 10% SDS-PAGE gels are shown in FIG. 3. Both probes photolabel an approximately 110 kDa protein in an UV-dependent manner (the "−" lanes). In order to assess the specificity of photoincorporation, a parallel sample was treated identically except that the reaction mixtures included a 10-fold excess of unlabeled competitor (UDP-GlcNAc or UDP-GlcA, respectively; marked the "+" lanes). The band intensities are reduced in comparison to the "−" lanes. The standards are marked in kDa.

Figure 4:
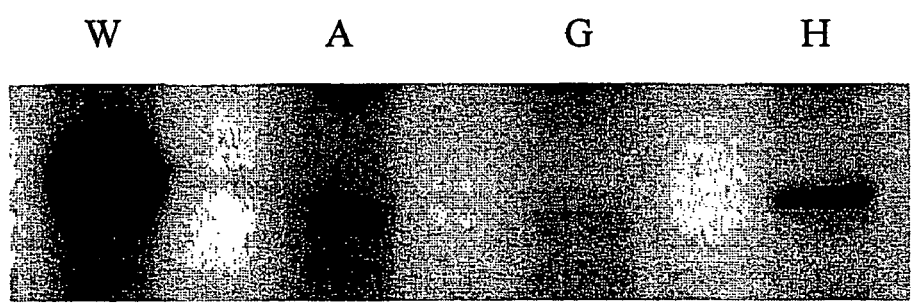
FIG. 4 is an autoradiogram depicting the reduced or absent photaffinity labeling of PmHAS in various Tn mutants of PmHAS.
Figure 6A:
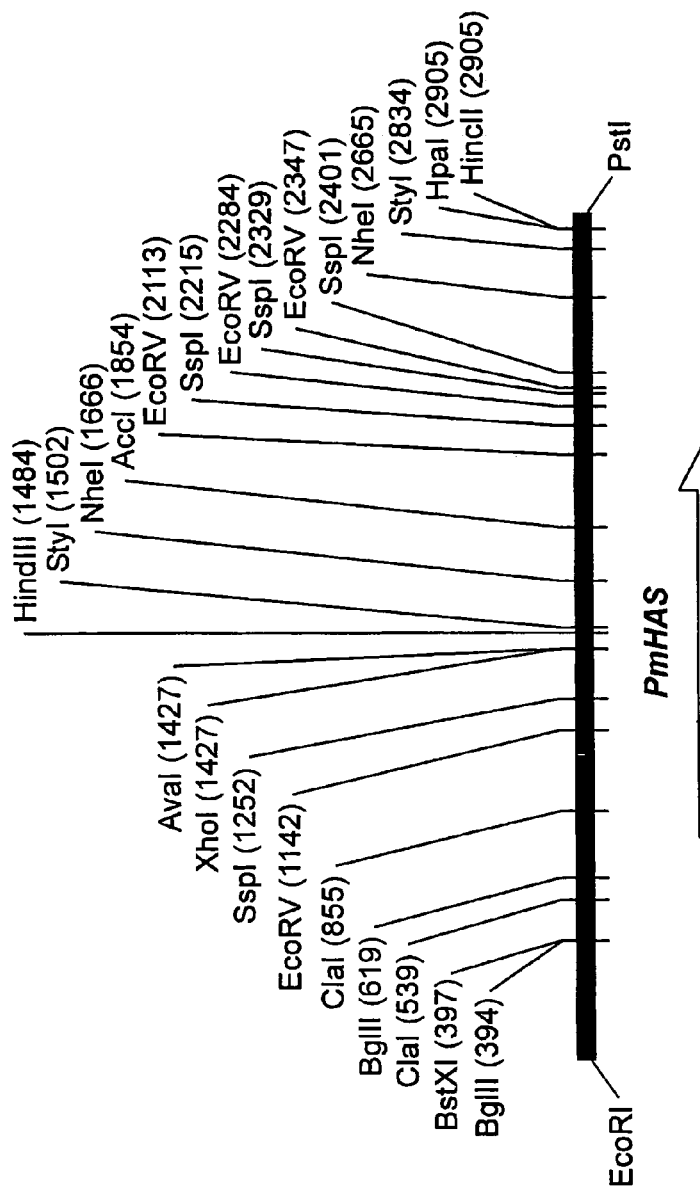
FIG. 6 graphically depicts the construction of pPmHAS and its subcloning into an expression vector.

Competition with the corresponding unlabeled natural UDP-sugar precursors lowered the extent of probe photoincorporation. In parallel experiments, [$^{32}$P]azido-UDP-Glc, an analog of the normal HA precursors, did not label this 110 kDa protein. Furthermore, membranes derived from Tn mutants had either no or very low amounts of azido-UDP-GlcA photoincorporation into this protein. As shown in FIG. 4, membrane preparations (60 μg of protein) from wild-type (W) or various acapsular Tn mutants (A, G, or H) were photolabeled with [$^{32}$P]azido-UDP-GlcA. The region of the autoradiogram in the vicinity of the approximate 110 kDa protein is shown in FIG. 4. No photoincorporation is seen in the A and G samples. The small extent of photolabelling in the H sample is due to the low rate of reversion observed with this particular mutant. The size of the photoaffinity labeled protein in the W sample corresponds well to the predicted $M_r$ of the cloned PmHAS ORF.

Membranes derived from *E. coli* SURE cells containing the pPmHAS plasmid, but not samples from cells with the vector pKK223-3 alone, synthesized HA in vitro when supplied with both UDP-GlcA and UDP-GlcNAc (25 versus less than or equal to 1.5 pMol GlcA transfer/mg protein/hour, respectively). No incorporation of [$^{14}$C]GlcA was observed if UDP-GlcNAc was omitted or if divalent metal ions were chelated with EDTA. The HAS activity derived from recombinant HAS was similar to the enzyme obtained from wild-type *P. multocida* membranes because $Mn^{2+}$ stimulated at least 10-fold more activity than $Mg^{2+}$.

Figure 5A:
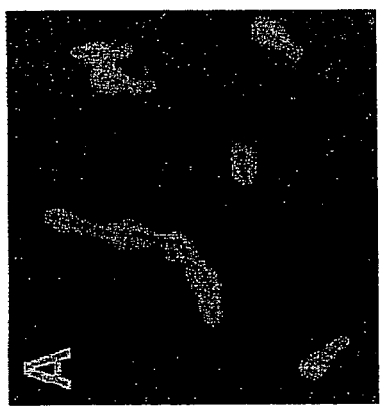
FIG. 5 depicts photomicrographs demonstrating HA production in recombinant *E. coli*.
Figure 5B:
Figure 6B:
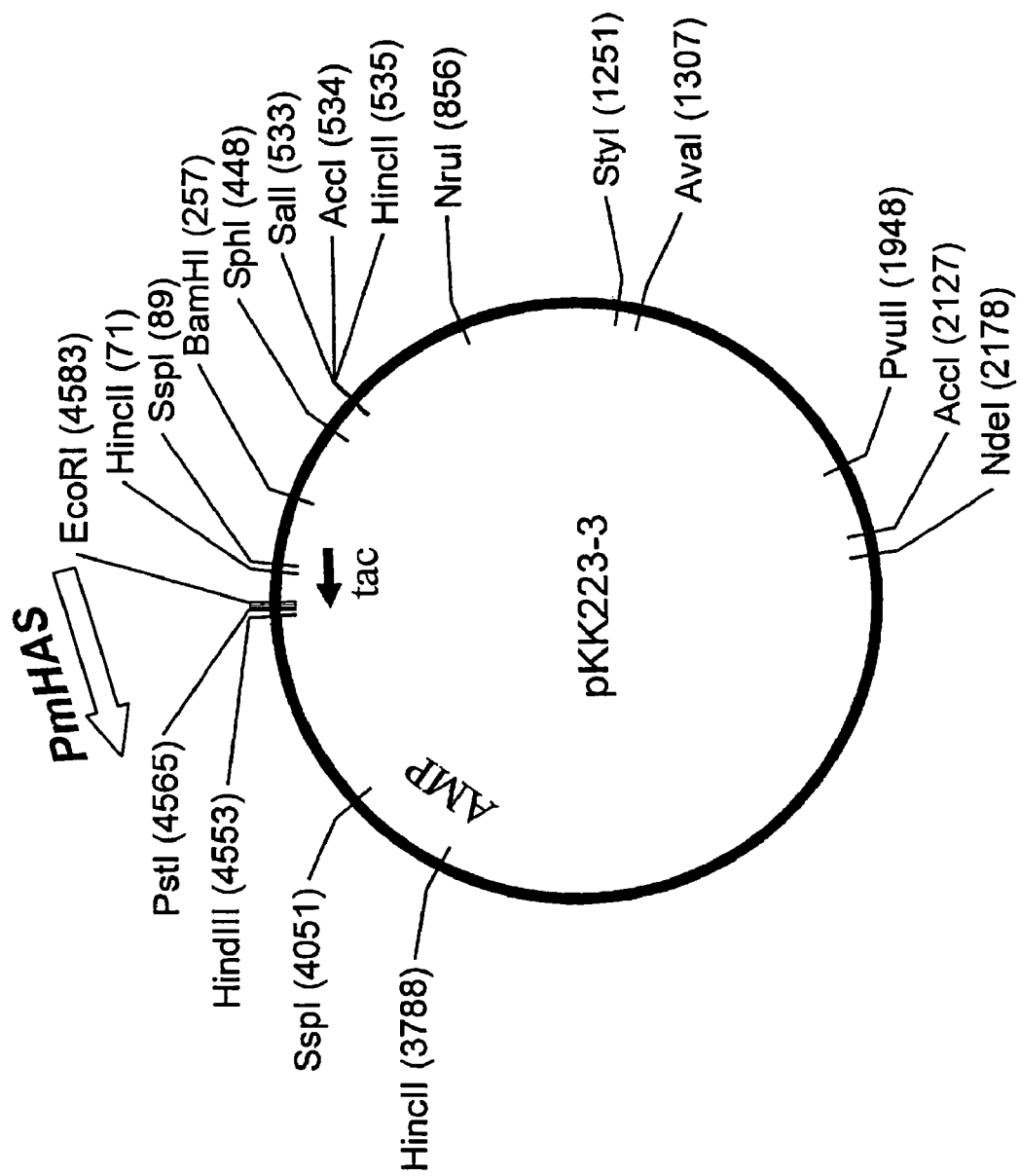

Cultures of recombinant *E. coli* were also tested for the presence of HA polysaccharide with a radiometric assay utilizing labeled HA-binding protein. *E. coli* K5 with pPmHAS produced 460 μg HA/ml/$A_{600}$. K5 cells with pKK223-3 vector alone did not produce HA (less than or equal to 0.05 μg HA/ml/$A_{600}$. For comparison, wild-type *P. multocida* wild type grown in the same media produced 1,100 μg HA/ml/$A_{600}$. *E. coli* K5 with pPmHAS produced such high levels of HA that the cells became encapsulated. As shown in FIG. 5, Panel A, the photomicrographs of recombinant *E. coli* with India ink staining (1,000× magnification) reveals that *E. coli* K5 cells with pPmHAS produce a substantial capsule that appears as a white halo around the cells.

The radius of the capsule of the recombinant strain was approximately 0.2-0.5 μm (assuming a bacterial cell width of 0.5 μm). This capsule could be removed by treatment with either bovine testicular hyaluronidase or *Streptomyces* HA lyase. As shown in FIG. 5, Panel B, the capsular material was removed from the *E. coli* K5(pPmHAS) cells by brief treatment with *Streptomyces* HA lyase. Thus, PmHAS directs polymerization of the HA polysaccharide.

Neither the native K5 host strain nor transformants containing pKK223-3 vector possessed a readily observable capsule as determined by light spectroscopy. K5 cells with pPmHAS were also deemed encapsulated by buoyant density centrifugation. The recombinant cells floated on top of the 58% Percoll cushion, whereas the vector control cells or hyaluronidase-treated recombinant cells pelleted through the Percoll cushion.

The p/PmHAS plasmid in *E. coli* K5 is the first generation system for making recombinant HA with PmHAS; other optimized vectors and/or hosts may give greater yields, and these other optimized vectors and/or hosts are herein contemplated for use with the present invention. One of ordinary skill in the art, given this disclosure, would be capable of optimizing such vectors and/or hosts.

2. Enzymological Characterization of PmHAS

Protein was determined by the Coomassie dye-binding assay utilizing a bovine serum albumin standard. *P. multocida* wild type (American Type Culture Collection 15742), a highly virulent turkey strain that forms very mucoid colonies, was maintained on brain/heart infusion medium under aerobic conditions at 37 degrees Celsius. An acapsular mutant of the strain which formed smaller, "drier" colonies, named TnA, was generated by a newly described Tn916 insertational mutagenesis method described herein.

Total membranes from *P. multocida* were prepared by a modification of the method for producing HA synthase from *E. coli* with recombinant plasmids containing hasA. Cells were grown with vigorous shaking to mid-log phase (0.4-0.8 $A_{600}$) and then bovine testicular hyaluronidase (Sigma Type V, 20 units/mL final) was added to remove the capsule. After 40 min., the cells were chilled on ice and harvested by centrifugation (2000×g for 15 min). The cells were washed twice PBS by repeated suspension and centrifugation, and the cell pellet could be stored at −80 degrees Celsius. All of the following steps were performed on ice unless noted otherwise.

The cells were resuspended by pipetting in ¹⁄₄₀₀ the original culture volume of 20% sucrose and 30 mM Tris, pH 8.0, containing the protease inhibitors pepstatin and leupeptin. Cell lysis was carried out by using lysozyme digestion (addition of ¹⁄₁₀ the suspended volume of 4 mg/mL enzyme in 0.1 M EDTA, 40-min incubation) followed by ultrasonic disruption (power setting 3, three cycles of 30 s on/off; Heat Systems W-380 with microprobe). Before the ultrasonification step, sodium thioglycolate was added to the mixture (0.1 mM final concentration) following the addition of phenylmethanesulfonyl fluoride. In all the remaining manipulations, the PBS also contained freshly added thioglycolate at the same concentration.

The lysate was treated with DNase and RNase (1 μg/mL each, 10 min at 4 degrees Celsius) and the cellular debris was removed by low-speed centrifugation (10000×g for 1 hour). The supernatant fraction was diluted 6-fold with PBS and the membrane fraction was harvested by ultracentrifugation (100000×g for 1 hour). The pellet was washed twice by repeated suspension in PBS containing 10 mM $MgCl_2$ followed by ultracentrifugation. For generating membrane preparations used in metal specificity studies, $MgCl_2$ was omitted and replaced with 0.2 mM EDTA during the wash steps. Membrane preparations were suspended in 50 mM Tris, pH 7, and 0.1 mM thioglycolate, at a concentration of 1-3 mg/mL protein and stored at −80 degrees Celsius.

HA synthase activity was routinely detected by incorporation of the radiolabel derived from the sugar nucleotide precursor UDP-[$^{14}$C]GlcA (0.27 Ci/mmol, ICN), into higher molecular weight products. The various assay buffers, described in the figure legends, also contained 0.3 mM DTT. Assays (100 μL final volume were initiated by addition of membranes to the reaction mixture and incubation at 37 degrees Celsius. After 1 hour, the reactions were terminated by addition of SDS (2% final) and mixing. For the kinetic studies, the product and precursors were separated by descending paper chromatography (Whatman 3M with 65:35 ethanol/1M ammonium acetate, pH 5.5). The HA polysaccharide at the origin of the paper chromatogram was eluted with water before liquid scintillation counting. The assays were typically performed under conditions in which no more than 5% of the precursors were consumed by limiting amounts of enzyme.

Controls to verify incorporation into authentic HA included omission of the required second sugar nucleotide precursor or digestion using the specific hyaluronidase from *Streptomyces hyalurolyticus*. Gel-filtration chromatography with SEPHACRYL™ S-200 (Pharmacia) in PBS was used to assess the molecular weight of the radiolabeled polymer formed in vitro under optimized assay conditions. These samples were treated as for paper chromatography except that, after termination, they were heated at 95 degrees Celsius for 2 minutes and clarified by centrifugation (15000×g for 7 minutes) before application to the column.

EDTA (0.2 mM) was used to chelate any metal ions present in assay mixtures to verify metal dependence of the HAS activity. Various divalent metals, including Mg, Mn, Cu, Co, and Ni, were tested as their chloride salts. The $K_m$ values of the substrates were estimated by titration of one sugar nucleotide concentration while holding the other radiolabeled precursor at a constant and saturating concentration. For these studies, UDP-[$^3$H]GlcNAc (30 Ci/mmol, NEN) was employed as well as the UDP-[$^{14}$C]GlcA precursor.

*P. multocida* cells produce a readily visible extracellular HA capsule, and since the streptococcal HasA is a transmembrane protein, membrane preparations of the fowl cholera pathogen were tested. In early trials, crude membrane fractions derived from ultrasonication alone possessed very low levels if UDP-GlcNAc-dependent UDP-[$^4$C]GlcA incorporating into HA [approximately 0.2 pmol of GlcA transfer (μg of proteins)$^{-1}$h$^{-1}$] when assayed under conditions similar to those for measuring streptococcal HAS activity. The enzyme from *E. coil* with the recombinant hasA plasmid was also recalcitrant to isolation at first. These results were in contrast to the easily detectable amounts obtained from *Streptococcus* by similar methods.

An alternative preparation protocol using ice-cold lysozyme treatment in the presence of protease inhibitors in conjunction with ultrasonication allowed the substantial recovery of HAS activity from both species of Gram-negative bacteria. Specific activities of 5-10 pmol of GlcA transfer (μg of protein)$^{-1}$h$^{-1}$ were routinely obtained for crude membranes of wild-type *P. multocida* with the new method. In the absence of UDP-GlcNAc, virtually no radioactivity (less than 1% of identical assay with both sugar precursors) from UDP-[$^{14}$C]GlcA was incorporated into higher molecular weight material. Membranes prepared from the acapsular mutant, TnA, posssessed no detectable HAS activity when supplemented with both sugar nucleotide precursors. Gel-filtration analysis using a Sephacryl S-200 column indicates that the molecular mass of the majority of the $^{14}$C-labeled product synthesized in vitro is $\geq 8 \times 10^4$ Da since the material elutes in the void volume; such a value corresponds to a HA molecule composed of at least 400 monomers. This product is also sensitive to *Streptomyces* hyaluronidase digestion but resistant to Pronase treatment.

Figure 7:
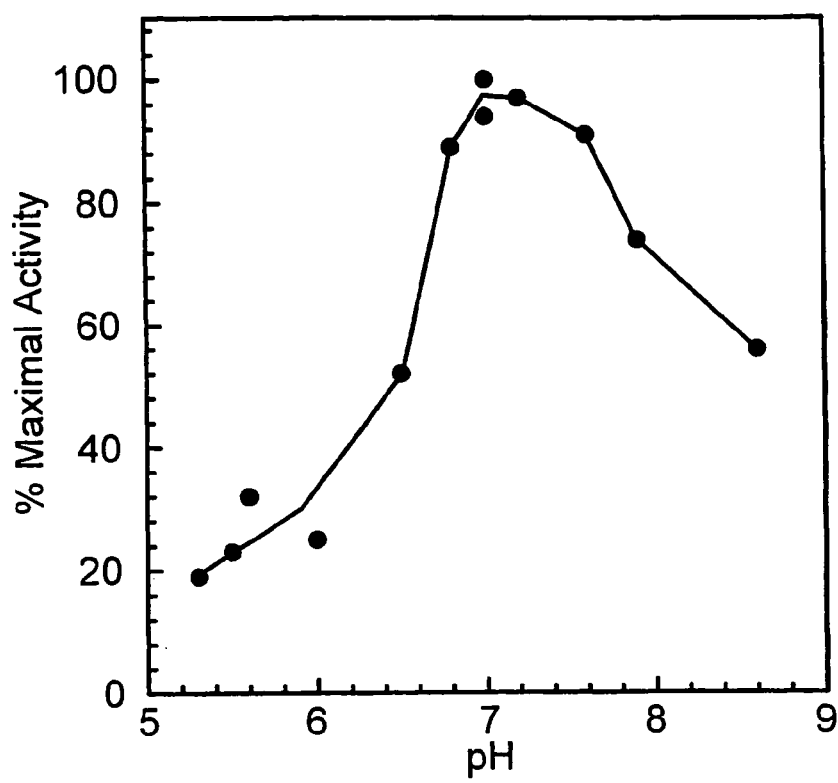
FIG. 7 depicts the pH dependence of PmHAS activity.

The parameters of the HAS assay were varied to maximize incorporation of UDP-sugars into polysaccharide by *P. multocida* membranes. Streptococcal HasA requires $Mg^{2+}$ and therefore this metal ion was included in the initial assays of *P. multocida* membranes. The *P. multocida* HAS was relatively active from pH 6.5 to 8.6 in Tris-type buffers with an optimum at pH 7, FIG. 7. FIG. 7 depicts the pH dependence of *P. multocida* HAS activity. The incorporation of [$^{14}$C]GlcA into HA polysaccharide catalyzed by membranes (38 μg of protein) was measured in reactions buffered at various pH values (50 mM Tris/2-(N-(morpholino)ethanesulfonic acid, bis-Tris/HCl, or tris/Hcl; no major buffer ion-specific effects were noted). The incubation mixture also contained 20 mM $MgCl_2$, 120 μM UDP-GlcA ($4.5 \times 10^4$ dpm/assay), and 300 μM UDP-GlcNAc. The incorporation of the assay using the optimal buffer, pH 7 Tris, was set to 100% activity. A broad pH optimum around neutrality was observed.

The HAS activity was linear with respect to the incubation time at neutral pH for at least 1 hour. The *P. multocida* enzyme was apparently less active at higher ionic strengths because the addition of 100 mM NaCl to the reaction containing 50 mM Tris, pH 7, and 20 mM $MgCl_2$ reduced sugar incorporation by approximately 50%.

Figure 8:
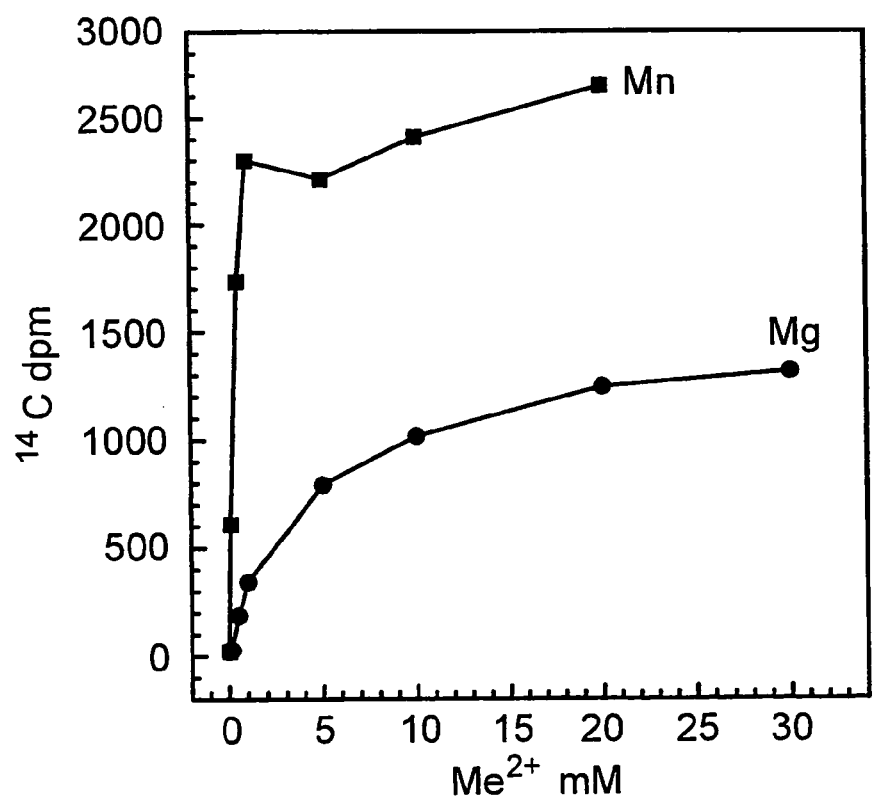
FIG. 8 depicts metal dependence of HAS activity.

The metal ion specificity of the *P. multocida* HAS was assessed at pH 7, FIG. 8. FIG. 8 depicts metal dependence of HAS activity. The production of HA was measured in the presence of increasing concentrations of Mg (circles) or Mn (squares) ion. The membranes (46 μg of protein), prewashed with 0.2 mM EDTA were incubated in a mixture of the metal ion in 50 mM Tris, pH 7, 120 μM UDP-GlcA ($4.5 \times 10^4$ dpm/assay), and 300 μM UDP-GlcNAc for 1 hour. The background with no metal present (22 dpm) was subtracted from each point. Mn is more effective than Mg.

Under metal-free conditions in the presence of EDTA, no incorporation of radiolabeled precursor into polysaccharide was detectable (<0.5% of maximal signal). $Mn^{2+}$ gave the highest incorporation rates at the lowest ion concentrations for the tested metals (mg, Mn, Co, Cu, and Ni). $Mg^{2+}$ gave about 50% of the $Mn^{2+}$ stimulation but at 10-fold higher concentrations. $Co^{2+}$ or $Ni^{2+}$ at 10 mM supported lower levels of activity (20% or 9%, respectively, of 1 mM $Mn^{2+}$ assays), but membranes supplied with 10 mM $Cu^{2+}$ were inactive. Indeed, mixing 10 mM $Cu^{2+}$ and 20 mM $Mg^{2+}$ with the membrane preparation resulted in almost no incorporation of label into polysaccharide (<0.8% of Mg only value).

Initial characterization of the *P. multocida* HAS was performed in the presence of $Mg^{2+}$. The binding affinity of the enzyme for its sugar nucleotide precursors was assessed by measuring the apparent $K_M$ value. Incorporation of [$^{14}$C]GlcA or [$^3$H]GlcNAc into polysaccharide was monitored at varied concentrations of UDP-GlcNAc or UDP-GlcA, respectively, FIGS. 9 and 10, respectively.

Figure 9:
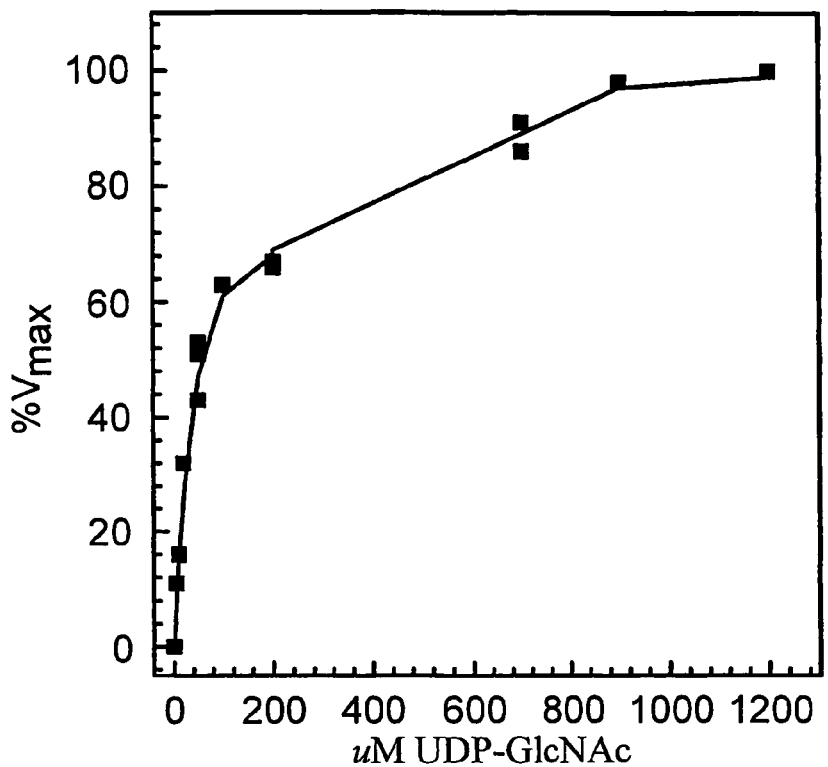
FIG. 9 depicts HAS activity dependence on UDP-GlcNAc concentration.

FIG. 9 depicts HAS activity dependence on UDP-GlcNAc concentration. Membranes (20 μg of protein) were incubated with increasing concentrations of UDP-GlcNAc in buffer containing 50 mM Tris, pH 7, 20 mM $MgCl_2$, and 800 μM UDP-GlcA ($1.4 \times 10^5$ dpm of $^{14}$C) for 1 hour. The background radioactivity (identical assay but no added UDP-GlcNAc) was subtracted from each point. The highest specific incorporation rate into HA (average approximately 780 dpm/hour) in the titration was defined a $V_{max}$ for normalization to 100%.

Figure 10:
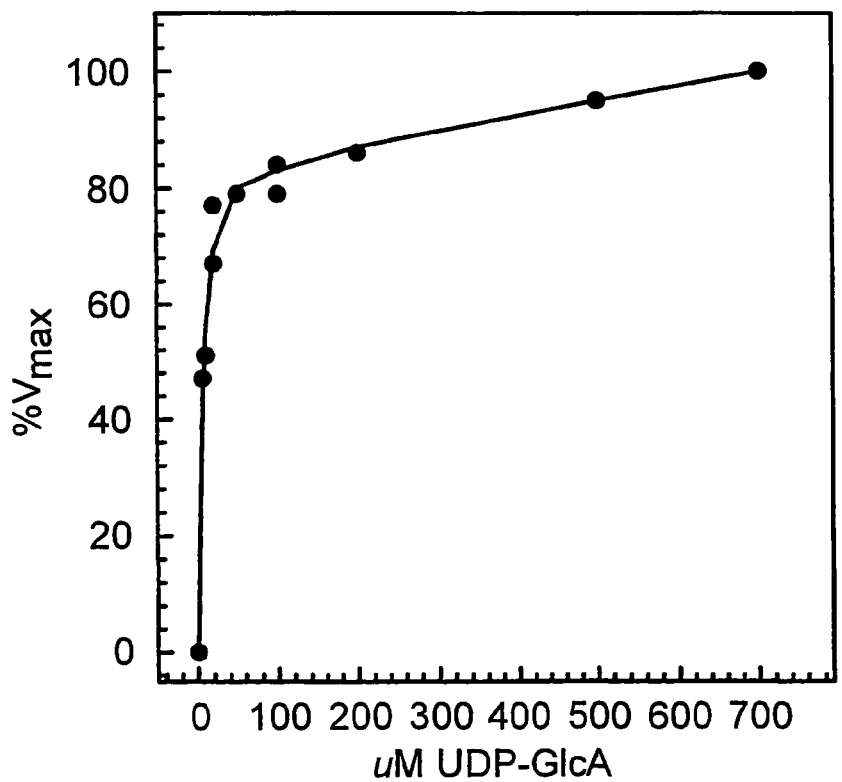
FIG. 10 depicts HAS activity dependence on UDP-GlcA concentration.

FIG. 10 depicts HAS activity dependence on UDP-GlcA concentration. In experiments parallel to those described in FIG. 9, increasing amounts of UDP-GlcA were incubated with 1 mM UDP-GlcNAc ($2.7 \times 10^5$ dpm of $^3$H) under the same general buffer and assay conditions. The background radioactivity (assay with no added UDP-GlcA) was subtracted from each point. The data is presented as in FIG. 9. Specific incorporation at $V_{max}$ averaged approximately 730 dpm/hour.

Figure 11:
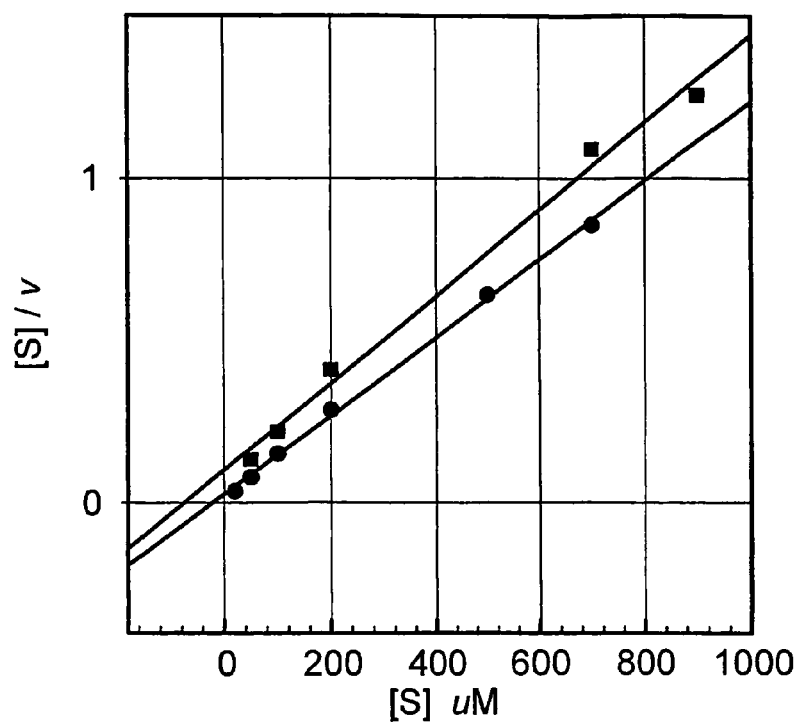
FIG. 11 is a Hanes-Woolf plot estimation of $V_{MAX}$ and $K_m$.

In $Mg^{2+}$ containing buffers, the apparent $K_M$ values ~20 μM for UDP-GlcA and ~75 μM for UDP-GlcNAc were determined utilizing Hanes-Woolf plots ([S]/v versus [S]) of the titration data shown in FIG. 11. FIG. 11 depicts the Hanes-Woolf plot estimation of $V_{max}$ and $K_M$. The specific incorporation data used to generate FIG. 9 (squares) and FIG. 10 (circles) were graphed as [S]/v versus [S]. The parallel slopes, which correspond to $1/V_{max}$, indicate that the maximal velocities for the sugar nucleotide precursors were equivalent. The x-axis intercept, which signifies $-K_M$, yielded $K_M$ values of 75 and 20 μM for UDP-GlcNAc and UDP-GlcA, respectively.

The $V_{max}$ values for both sugars were the same because the slopes were equivalent. In comparison to the results from assays with $Mg^{2+}$, the $K_M$ value for UDP-GlcNAc was increased by about 25-50% to ~105 μM and the $V_{max}$ increased by a factor of 2-3 fold in the presence of $Mn^{2+}$. These values are represented in Table I.

TABLE I

| membrane wash | assay ion | $K_M$(μM) | $V_{max}$(pmol/h) |
| --- | --- | --- | --- |
| Mg | Mg | 75 ± 5 | 114 ± 36 |
| EDTA | Mg | 55 ± 25 | 98 ± 1 |
| EDTA | Mn | 105 ± 5 | 380 ± 70 |

As stated previously, the HA capsules of pathogens *P. multocida* and *S. pyogenes* are virulence factors that aid the evasion of host defenses. The HA synthase enzyme from either bacterial source utilizes UDP-sugars, but they possess somewhat different kinetic optima with respect to pH and metal ion dependence and $K_M$ values. Both enzymes are most active at pH 7; however, the PmHAS functions better on the alkaline side of the pH optimum up to at least pH 8.6. On the other hand, the spHAS reportedly displays more activity at slightly acidic pH and is relatively inactive above pH 7.4. The *P. multocida* enzymes utilizes $Mn^{2+}$ more efficiently than $Mg^{2+}$ under the in vitro assay conditions. The PmHAS binds the UDP-sugars more tightly than streptococcal HasA. The measured $K_M$ values for the PmHAS in crude membranes are about 2-3 fold lower for each substrate than those obtained from the HAS found in streptococcal membranes.

3. Use of the PmHAS for Vaccinations

The DNA sequence of PmHAS may also be used to generate potential attenuated vaccine strains of *P. multocida* bacteria after knocking out the normal microbial gene by homologous recombination with a disrupted version. Additionally, the PmHAS DNA sequence allows for the generation of diagnostic bacterial typing probes for related *P. multocida* types that are agricultural pathogens of fowl, cattle, sheep and swine.

There are at least five different types of the bacterial pathogen *P. multocida* with distinct capsule antigens. Fowl cholera or avian pasteurellosis, which is mostly caused by Type A strains, is a widespread, economically damaging disease in commercial poultry. An acute outbreak of fowl cholera is usually detected only when the birds suddenly collapse as symptoms often appear just a few hours prior to death. Although little is known about the molecular basis for the virulence of *P. multocida*, apparently one of the pathogen's virulent strains possesses a polysaccharide capsule, and their colonies display a mucoid or "wet" morphology on agar plates. White blood cells have difficulty engulfing and inactivating the bacteria and the complement complex cannot contact the bacterial membrane to cause lysis. The major capsule component of the Carter Type A *P. multocida*, which is responsible for perhaps 90-95% of fowl cholera disease, is the polysaccharide HA and HA does not illicit an immune response in virtually all members of the Animal Kingdom. Even if an immune response did occur, it would present a problem for the bird because of the repercussions of autoimmune reactions. Type A *P. multocida* strains are also prominent causes of swine and bovine pneumatic pasteurellosis, and shipping fever in cattle.

Two other *P. multocida* capsular types, Type D and Type F, are less well studied but are prevalent pathogens in North America. Type F is isolated from about 5-10% of fowl cholera cases. Type D is also a cause of pneumonia in cattle, sheep, and swine. Isolates from the pneumonic lesions of these domestic animals were analyzed from capsule type and about 25-40% were Type D and the rest were Type A. Additionally, the Type D strain is intimately involved in swine atrophic rhinitis. The capsules of these Type D and Type F microbes are composed of different polysaccharides with unknown structures, but they are apparently similar to chondroitan, a prevalent molecule on the vertebrate body. The general backbone structure of chondroitan, repeating (β1,4)GlcA(β1,3)GalNAc units, is very similar to HA. It is not surprising, therefore, that the Type D and F polysaccharides are poorly immunogenic.

Typically, the antibodies against bacterial surface components derived from previous infections (or vaccinations) are an important means for white blood cells to adhere to a bacterium during phagocytosis; this feature usually makes the immune response extremely effective in fighting disease. Thus, the presence of capsules composed of non-immunogenic polymers, such as HA or chondroitan-like sugars, compromise the efficiency of all phases of the host defenses. *Streptococcus pyogenes,* a human pathogen, also employs a HA capsule as molecular "mimicry" to protect itself from host defenses. Acapsular *S. pyogenes* mutants cannot survive in blood and are 100 fold less virulent than the wild-type in mice. Many virulent *E. coli* strains possess capsules comprised of other polysaccharides that mimic host molecules and aid the cell in eluding the immune system. The capsules of all these pathogenic bacteria are clever evolutionary adaptations that must be overcome in order to defeat the disease.

Previous investigations have focused on the capsule of *P. multocida* and its role in virulence. As for Type A fowl strains, wild-type encapsulated bacteria and various acapsular forms were tested for their ability to survive challenges by isolated host defenses (white blood cells and complement) or to cause infection and death of live fowl. The acapsular bacteria were typically: (a) spontaneously arising mutants; (b) chemically-induced mutants; or (c) wild-type bacteria treated with hyaluronidase [HAase], a specific HA-degrading enzyme. In general, capsule-deficient Type A bacteria were more readily killed by isolated host defenses in vitro.

Turkey serum killed both mutant and HAase-treated cells, while the wild-type cells multiplied. The complement system was involved, since the killing ability was lost by heat or calcium-chelator treatment of the serum prior to incubation with bacteria. That encapsulated wild-type cells consume or reduce the level of complement in sera without inactivation indicates that the complex binds to but cannot lyse the cells. Turkey macrophages and heterophils phagocytose both acapsular variants and HAase-treated cells more avidly than wild-type cells.

In live animal testing, the spontaneous mutants were $10^3$ to $10^5$-fold less virulent than the corresponding wild-type parent strain, as assessed by $LD_{50}$ (i.e. the lethal does for 50% of the tested animals). This enormous difference shows the importance of the capsule in pathogenesis by Type A strains. The fate of the bacteria in live turkeys also depended on encapsulation; only wild-type cells survived in the liver. Fifteen to twenty-four hours after injection, wild-type cells were found in the blood at a $10^5$-fold higher concentration than the unencapsulated mutants. Another role for the HA capsule is adhesion and colonization. Certain cells in the vertebrate body possess specific HA-binding proteins on their surface; potentially the bacteria could adhere to the host via this protein/HA interaction.

Likewise, the capsules of Type D and Type F *P. multocida* are implicated as virulence factors that confer the microbes with resistance to phagocytosis. When Type D or F cells are treated with chondroitinase, the microbes lose their capsule and are more readily phagocytosed in vitro. Furthermore, these polymers are not strongly immunogenic. From in vivo testing, encapsulated Type D strains produced more severe nasal lesions in swine and had a much lower $LD_{50}$ in mice than unencapsulated variants ($10^2$ vs. $10^{7-8}$ cells, respectively).

In the case of the Type A and D mutants studied above, however, the genetic nature of their defects were not known, and there was no facile method for mapping the mutations. Particularly with chemical mutagenesis, there is likely to be more than one mutation in any given "mutant". Furthermore, it was not shown that HA production was completely eradicated in the "acapsular" mutants; thin capsules not detectable by colony morphology, light microscopy or chemical test could still exist. More sensitive radiometric and buoyant density assays are required for detection of even small capsules.

Utilizing these new methods, it has been determined that one strain used in several virulence assays and reported as acapsular, actually possesses a very thin HA capsule. Therefore, it is important to determine the effects from a truly acapsular strain.

Historically, the genes involved in *P. multocida* capsule production were not known. Several genes residing in the capsule locus of another bacterium in a related genus, *Haemophilus influenzae,* were mapped and sequenced, but the molecular details of the biosynthetic apparatus are not available. Even in *E. coli,* a very well studied Gram-negative organism, the exact role of every putative gene product is not well understood, although the loci of capsule formation has been thoroughly mapped and the DNA sequences obtained for several capsule types.

The cloning and sequencing of the HA biosynthesis locus of *Streptococcus pyogenes* has been reported. This microbe, like *P. multocida,* utilizes a HA capsule to evade human defenses. The HA operon contains three genes arranged in tandem on an approximately 4 kb of DNA. The first gene, hasA, encodes the 45.1 kDa HA synthase that polymerizes the two sugar nucleotide precursors, UDP-GlcA and UDP-GlcNAc, to form the HA polysaccharide. The second gene, hasB, encodes a 45.5 kDa UDP-glucose dehydrogenase which converts UDP-glucose (UDP-Glc) into UDP-GlcA for HA biosynthesis. The third gene, hasC, encodes a 34 kDa UDP-glucose pyrophosphorylase which forms UDP-Glc from UTP and glucose-1-phosphate. There is an auxiliary enzyme dedicated to forming UDP-sugars for capsule biosynthesis; another "housekeeping" gene residing elsewhere in the chromosome supplies UDP-Glc for the bacterium's normal metabolic pathways. UDP-GlcNAc is present in all eubacteria due to its role in cell wall synthesis. Therefore, the HA synthase and dehydrogenase are the only two exogenous proteins needed to direct HA polysaccharide synthesis in heterologous bacteria. *S. pyogenes* HA synthase, which is predicted to be a membrane protein with transmembrane helices, probably both polymerizes HA and transports the growing polysaccharide chain to the outside of the cell.

As previously discussed above, the gene responsible for capsule production of HA in *P. multocida,* has been isolated and sequenced. (See e.g., SEQ. ID Nos. 1 and 2.) This gene is disclosed and claimed as part of the present invention. As also discussed previously, the polymers of the *P. multocida* capsules pose a dilemma for host defenses. Using the PmHAS gene sequence information, recombinantly produced *P. multocida* strains having the HA synthesis gene "knocked out" will disrupt the bacterial capsular synthesis of *P. multocida*. Using the "knocked out" strain as a vaccine will allow the host organism to fend off challenges by the pathogen in the field.

As discussed above, Tn916, a versatile and proven mutagen, inserts into the chromosome of *P. multocida* at various apparently quasi-random locations. The Tn was introduced into the cells on a "suicide" plasmid—i.e. one that cannot replicate in *P. multocida*—via electroporation. The Tn mobilized or jumped off the plasmid and into the genome at a frequency of about 4,000 events/microgram of DNA. The resulting progeny possessed the tetracycline resistance gene from Tn916 and were easily selectable by the drug.

Also discussed above was the fact that a panel of independent transposon mutants defective in capsule biosynthesis from the virulent parental strain were generated. After using a combination of visual and biochemical screening of the approximately $10^5$ transfected colonies, two classes of capsule defects have been found which result in microcapsular or acapsular mutants. The first class (seven independent strains) possessed a very small capsule of HA, hence named microcapsular. The encapsulated wild-type strain produces large mucoid, iridescent colonies on media plates and the individual cells form a capsule with a thickness approximately equal to the cell body diameter as measured by light microscopy. In comparison, the microcapsular strains form smaller, iridescent colonies that appear somewhat drier on media plates; the capsule thickness of the individual cell is on the order of one quarter (or less) of the wild-type.

Four mutants (four independent strains) appeared to be truly acapsular forming small, dry colonies on media plates. No capsule was detected by light microscopy. The buoyant density of the acapsular strain, which depends on the state of encapsulation, was equivalent to wild-type cells that were stripped of their capsule by hyaluronidase treatment. These strains also lacked HA synthase activity; exogenous radiolabeled UDP-sugar precursors were added to the preparations derived from these mutants but no HA polysaccharide was formed.

Two of the acapsular mutants, TnH and TnL, possessed the interesting property that at a frequency of about $10^{-3}$, occasional revertants with a wild-type capsule phenotype appeared on media plates. The revertant cells possessed a wild-type capsule as deemed by light microscopy and radiometric assay for HA polysaccharide. The molecular explanation is that occasionally the Tn excised neatly from the capsule gene (no added or deleted bases) and integrates elsewhere in the chromosome. The resulting encapsulated progeny on media plates are readily observable. This reversion phenomenon is classic genetic proof that the Tn in these two strains was responsible for mutating an important site necessary for capsule synthesis. However, due to this relative instability, a Tn-derived mutant is unsuitable for an attenuated vaccine strain; at some frequencey, virulent forms could arise.

Southern blotting was used to map the location of the Tn in both the original acapsular mutants and the encapsulated revertants. TnH and TnL have a Tn element in the same locus as deemed by the pattern after HindIII or BstXI digestion as shown in FIG. 12. FIG. 12 is a Southern blot mapping of the Tn mutants. Chromosomal DNA from an assortment of capsule mutants, encapsulated revertants, and controls were digested with HindIII. The DNA was separated by gel electrophoresis and subjected to Southern blot analysis. The Tn probe recognizes two bands for each transposon due to an internal restriction site (forms a large 10 kb and a small 5 kb arm). The Tn probe does not hybridize with DNA from the parental strain without a Tn (lane 0). Multiple DNA preparations derived from separate colonies of the acapsular mutants TnH (H) and TnL (L) or individual encapsulated revertants (noted with underlined letters) were run. All the mutants had a single Tn element insertion, except for TnL which usually had 2 copies of the Tn (one of the subcultured strains had 3 copies). TnW (W) is a mucoid Tn-containing control strain. The positions of the lambda HindIII markers (λ) for 23.1, 9.4, and 6.6 kb (top to bottom) are marked.

The Tn element in the acapsular mutants H and L (which have no HA synthase activity), and a representative microcapsular mutant, TnD (D), map to the same position. Upon reversion to the mucoid phenotype, the relative Tn element moved to a new location in every case. The disrupted DNA from the mutants was isolated at this locus and probes were generated for the capsule genes.

Subsequent sequence analysis determined that the TnH and TnL insertions were approximately 1 kb apart. In all cases, the revertants of these mutants lost the Tn at the original position and gained a new Tn at different sites (i.e. FIG. 12, lanes with the underlined letters). Alternatively, there has never been an observed reversion of any of the microcapsular mutants to the encapsulated form. The Tn responsible for all of the microcapsular mutants (typified by TnD) mapped to the same 17 kilobase HindIII fragment as the TnH and TnL mutants. This co-localization was confirmed by mapping with BstXI as well.

In the other acapsular mutants, TnA and TnG, the Tn elements were located in other irrelevant genes and the HA capsule locus was rendered nonfunctional by spontaneous mutations. The occasional spontaneous mutation is to be expected; in fact, in similar studies of the streptococcal capsule locus, 12 out of 13 strains were the result of spontaneous mutations.

The Tn916 insertional mutagenesis was used to identify and clone the DNA involved in HA capsule biosynthesis of *P. multocida*. In accomplishing this task, three steps were used: (i) sequencing of host DNA at a Tn insertion site utilizing a primer corresponding to DNA at the terminus of Tn916, (ii) designing PCR primers for the capsule gene based on the new sequences to amplify the DNA segment between two Tn elements, and (iii) screening wild-type genomic libraries in lambda virus for a functional clone utilizing the capsule locus-specific PCR product as a hybridization probe.

The key step in obtaining the *P. multocida* DNA adjacent to the Tn was the use of the recently formulated direct sequencing technique which has been fully described in DeAngelis, P. L. (1998) "Transposon Tn916 insertional mutagenesis of *Pasteurella multocida* and direct sequencing of the disruption site," *Microbial Pathogenesis*, which is fully incorporated by reference herein. The *P. multocida* genome from all capsular types contains many sites for the restriction enzyme HhaI; thus almost every DNA fragment in the digest is less than 7 kilobases (kb) and is shown in FIG. 13, lane "O".

Figure 12:
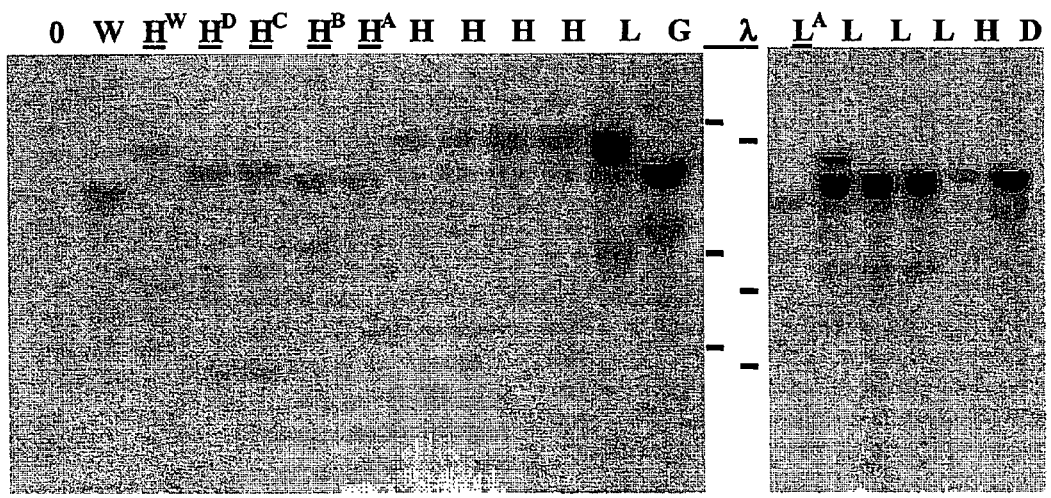
FIG. 12 is a Southern blot mapping of Tn mutants.
Figure 13:
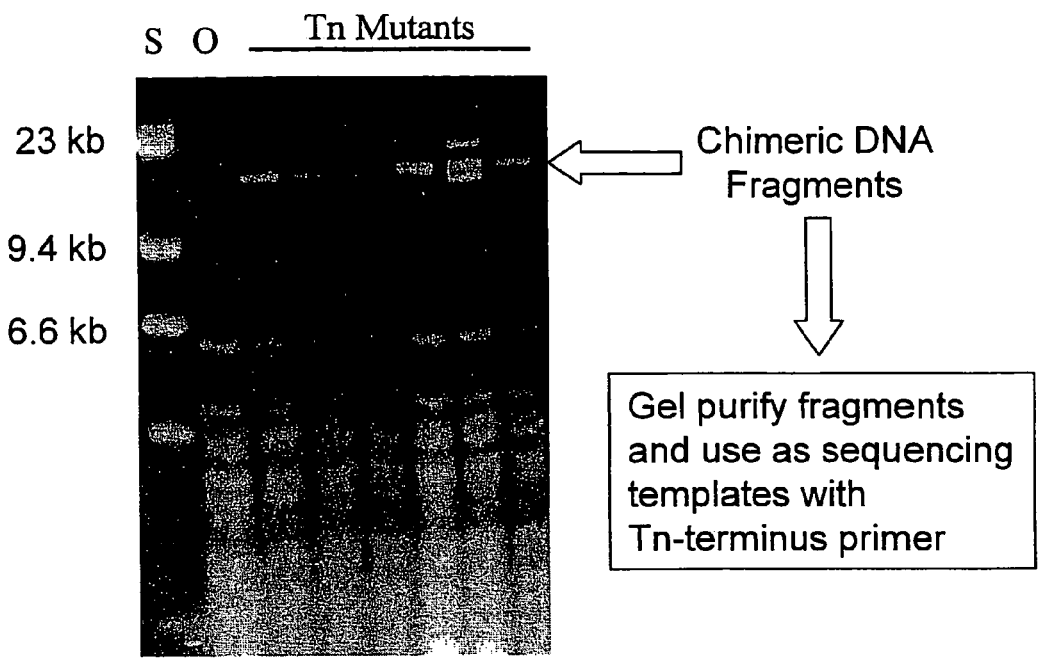
FIG. 13 depicts chimeric DNA templates for sequence analysis of Tn disruption sites.

FIG. 13 depicts chimeric DNA templates for sequence analysis of Tn disruption sites. Through this method, the DNA sequence of any gene interrupted by the Tn916 element can be rapidly and directly obtained. The method capitalizes on the differential sensitivity of the Tn element and the type A *P. multocida* genome to the restriction enzyme HhaI. The 16 kb Tn element has only one HhaI site resulting in 12 and 4 kb fragments upon digestion. Therefore, any gene interrupted by the Tn element will have an additional 12 kb of DNA. The increase in HhaI fragment size allows the facile resolution of the Tn-tagged gene from the rest of the chromosomal DNA by conventional agarose electrophoresis. This 0.7% gel shows the HhaI digest pattern of chromosomal DNAs from the parental strain without a Tn (lane 0), and several Tn-containings mutants (Tn mutant lanes). The lambda/HindIII markers (lane S) are denoted in kb. The chimeric Tn/genomic DNA fragments that migrate at approximately 13-17 kb (marked with the arrow) are only found in the Tn mutants. Note that lane L has three chimeric bands; this particular mutant has three Tn elements (see FIG. 12).

The chimeric DNA can be isolated and used directly as a sequencing template; no cloning or PCR is required. The resulting large chimeric DNA molecule, which is readily separated from the rest of the small genomic fragments by agarose gel electrophoresis, serves as the template in cycle sequencing reactions. A sequencing primer corresponding to the right-hand terminus of the Tn916 directs elongation outward into the disrupted DNA. Thus, sequence data at the disruption site of mutant DNA can be routinely obtained without PCR amplification or cloning the template DNA.

Figure 14:
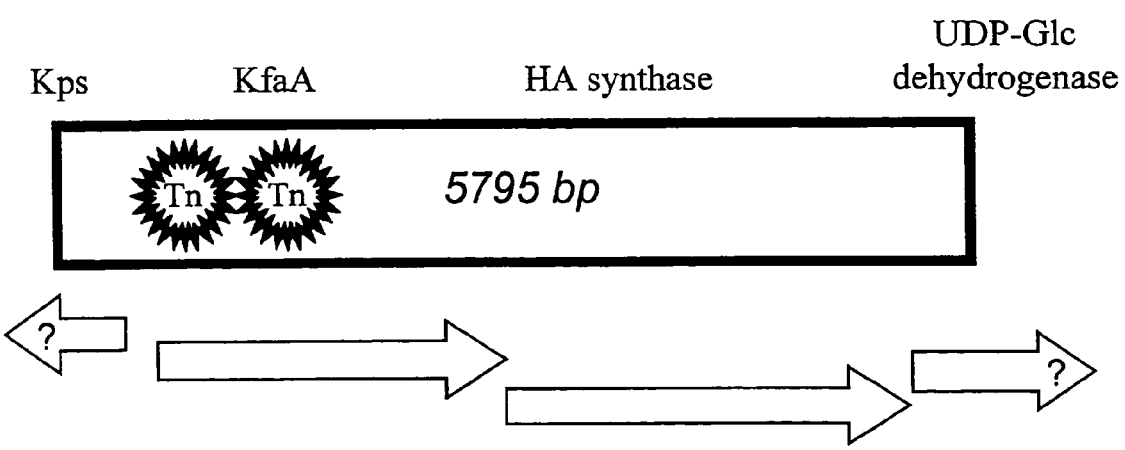
FIG. 14 is a diagrammatic representation of a portion of the HA biosynthesis locus of Type A *P. multocida*.

The new sequence information was used to design PCR primers for amplification of the region of DNA between the TnL and TnH mutants. A specific 1 kb product was used as a hybridization probe to obtain a 5.8 kb portion of the capsule biosynthesis operon of Type A *P. multocida*, as outlined in FIG. 14 which shows the schematic of HA biosynthesis locus of Type A *P. multocida.* As FIG. 14 depicts, the insert of a Type A genomic DNA clone that could direct biosynthesis of HA in *E. coli* was sequenced. It was found that the open reading frames encode: two proteins similar to *E. coil* molecules implicated in polysaccharide transport, Kps and KfaA; a HA synthase that polymerizes HA polysaccharide; and a precursor forming enzyme, UDP-glucose dehydrogenase. Deletion analysis of the original plasmid showed that an intact HA synthase was essential for HA production in heterologous bacteria. The location of the original Tn insertions corresponding to TnH and TnL are marked with stars. The Tn insertion events apparently caused polar mutations that stopped expression of the downstream HA synthase and dehydrogenase genes. Thus, by using sequence analysis, the intact open reading frames of the novel PmHAS and a putative polysaccharide transport homolog, similar to *E. coli* KfaA, were found. The data also shows that an UDP-Glc dehydrogenase homolog, which makes UDP-GlcA precursor, and another transporter protein, an *E. coli* kps gene homolog, are present near the HA synthase.

The single 110 kDa protein from *P. multocida,* PmHAS, directs HA capsule production in *E. coli.* The capsule of the recombinant cells produced with the PmHAS on a plasmid was as thick as the virulent wild type strain. The capsular material was deemed authentic HA by its susceptibility to specific HA lyase digestion and its reactivity with selective HA-binding protein. Interestingly, PmHAS is not very similar to the other HASs at the amino acid level.

In order to make stable isogenic mutants of *P. multocida,* a modification of a mutagenesis method employed with *P. haemolytica* was employed. A knockout cassette for targeted inactivation by a double crossover of the HA synthase was made. A promoterless chloramphenicol resistance gene (cat) was inserted into the middle of the entire PmHAS open reading frame (at the XhoI site), and cloned into a plasmid (pKK223-3) that does not stably replicate in *P. multocida.* The plasmid was transformed into encapsulated wild-type strain and the cells were plated on media with chloramphenicol. When integrated into the target gene, the intact PmHAS protein is no longer formed. The cat gene is transcribed by the endogenous capsule gene promoter; the downstream gene, UDP-glucose dehydrogenase should not be affected. Therefore, true isogenic mutants are formed.

Three isogenic acapsular mutants have been isolated. None of these mutants were detected as having capsules under light microscopy and India ink staining. The HA synthase was disrupted at both the DNA and biochemical levels. See e.g., Table II. By Western blot analysis using an antibody directed against a portion of the PmHAS enzyme, the acapsular knockout mutant was missing the approximately 110 KDa band, the PmHAS enzyme, found in the wild-type parent. In combination with the data in Table II (the lack of polysaccharide production), no functional PmHAS is found in the knockout strain.

Certain regions are common or very similar between genes of the various capsular types. This is shown in the Southern blot analysis of Type D or F DNA depicted in FIG. 15. As depicted in FIG. 15, chromosomal DNA from Type A, F, or D strains was digested with either HindIII or EcoRI (right or left lane, respectively, for each probe) and subjected to Southern blotting. Digoxigenin-labeled PCR product probes corresponding to regions of either the kfaA homolog (K) or HA synthase (H) genes from Type A were used to detect homologous sequences in bacteria of other capsule types (bands marked with stars). KfaA homologs are apparent in both Type F and D. A very similar synthase homolog is found in Type F, but not in Type D. The probes are suitable for screening libraries. The lambda/HindIII standards are marked in kilobases.

Type F has regions that are similar to both probes, while Type D was only similar to the transporter protein probe. PCR was used with several sets of primers corresponding to the Type A sequences to amplify Type D or F genomic DNA as shown in FIG. 16. PCR of heterologous DNA with Type A primers is depicted in FIG. 16. Various primer pairs corresponding to the kfaA homolog gene (Panel A) or the HA synthase gene (Panel B) of the Type A strain were used to amplify genomic DNA isolated from several other *P. multocida* strains with different capsule types. Forty cycles (94° C., 30 sec; 42° C., 30 sec; 72° C., 60 sec) of polymerase chain reaction with Taq enzyme were performed.

The reaction mixes were separated on a 10/0 agarose gel and stained with ethidium (lanes: A, Type A; D, Type D; F, Type F; 0, no template control. Standards (S) are the 100 bp ladder, the 1 and 0.5 kb bands are marked with arrows. The P-I primer pair shows products for all three capsule types, but the Type D product is smaller than the other products. The P-II and P-III pairs amplify Type A and F DNA only. In contrast, the P-IV and P-V pairs amplify Type A only. It appears that the Type A and F capsule loci are more similar to each other than to type D. The PCR products from the P-I primer pair will serve as good hybridization probes for the capsule locus from other types.

Figures 17, 18:
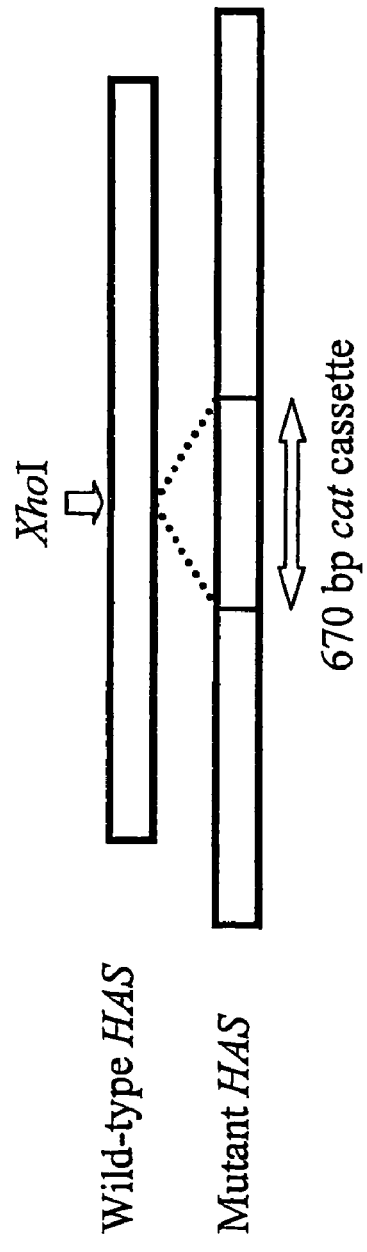
FIG. 17 is a partial sequence comparison of type A and F KfaA homologs and *E. coli* KfaA.
FIG. 18 is a schematic of wild-type HAS gene versus a knockout mutant gene.

Not all combinations of primers yielded PCR products with the heterologous template DNA. 0.2-1 kb portions of Type F genes encoding the HA synthase or the capsule polysaccharide transporter analog were amplified. Also amplified was a 1 kb region of the Type D genome encoding the transporter protein. Sequence analysis of several PCR products revealed homologous yet distinct sequences. Overall, this data suggests that the Type A and F strains are more related to each other and not as similar to type D. Sequence comparison of Type A and F KfaA homologs and *E. coli* KfaA is shown in FIG. 17. The PCR product that was generated by amplification of Type F DNA with the P-I primer set (see FIG. 16) was gel-purified and sequenced with one of the original primers. It was found that the type A and F sequences were very similar at the amino acid level; this partial alignment of the protein sequences shows that in this region the sequences are largely identical with some mismatches (the differences are underlined in FIG. 17). Overall, the *P. multocida* sequences are quite homologous to the *E. coli* KfaA protein, which is implicated in polysaccharide transport (the identical residues are bolded in FIG. 17). These PCR products will also be useful as hybridization probes to obtain functional capsule loci from Type D or F genomic libraries. The cloned DNA also allows the construction of gene knockout plasmids: wherein, the resulting mutant strains are useful for virulence assays or vaccines.

The production of the bacterial capsule of *P. multocida* involves at least the following steps: (i) synthesis of sugar nucleotide precursors; (ii) polymerization of precursors to form the capsular polysaccharide; and (iii) export or transport of the polysaccharide to the extracellular space where capsule assembly occurs. Of course, there are potential regulatory genes or factors that control enzyme levels or enzymatic activity, but the focus is on the major structural enzymes of the pathway. In *E. coli*, the candidate type 2 capsule genes encoding enzymes for this process are located together at a single site on the bacterial chromosome. *E. coli* strains that make capsules with different structures have varied enzymes for step (i) and (ii) above, but all appear to share a common transport/export machinery for step (iii).

It has been discovered that in *S. pyogenes*, a single integral membrane enzyme polymerizes the precursor sugars, and also transports the HA polysaccharide across the membrane. Type A *P. multocida* has four different genes that are involved in each of the three biosynthetic steps for bacterial capsule production. (See FIG. 14) The similarity of the *P. multocida* polysaccharide transporter to the *E. coli* homolog at the protein level suggests that the general functions of some other capsule genes may also be similar to these two species.

The role of the capsule as a virulence factor in fowl cholera has been assessed. In order to avoid pitfalls and caveats encountered in studies of bacterial capsules and virulence, defined mutants were compared to the wild-type microbes. Isogenic Type A mutants having disrupted capsule genes were tested for their ability to avoid preexisting or preimmune host defenses in vitro, as well as to infect living fowl in vivo. The stable isogenic mutants were produced according to the methods described hereinabove. Using a disrupted version of the PmHAS gene on a plasmid (see FIG. 18) and homologous recombination, a recombinant *P. multocida* strain was created that had lost the ability to make a hyaluronan capsule. The strain was further analyzed at both the DNA and biochemical levels. We found that the functional HA synthase gene was replaced with a defective gene containing a cat cassette disruption by both Southern blot and PCR analyses. (See FIG. 19).

Confirmation of gene disruption is shown in FIG. 19. Panel A is a Southern blot analysis. Chromosomal DNA from various strains was digested with HindIII, separated on a 0.7% agarose gel, and transferred to nitrocellulose. The blot was hybridized with a *P. multocida* HAS gene probe. Two bands were detected due to an internal HindIII restriction site in PmHAS gene. Lane M is the mucoid transformant; Lane KO is the acapsular knockout mutant; Lane P is the parental strain. The addition of the 670 bp cat cassette causes the size shift of the upper band in the KO lane (marked with an arrow).

Panel B of FIG. 19 is a PCR analysis. The DNA in cell lysates from various strains was amplified by 35 cycles of PCR with a pair of oligonucleotide primers that flank the XhoI site of PmHAS. The length of the amplicon from the normal, wild-type gene is 650 base pairs. The PCR reactions were separated on a 1% agarose gel and visualized with ethidium bromide. Lane M is the mucoid transformant; Lane KO is the acapsular knockout mutant; Lane P is the parental strain; Lane C is the cloned PmHAS plasmid control; and Lane S are the size standards. The PCR product produced by the knockout mutant template is approximately 1,300 bp (marked with arrow); this band is composed of the 670 bp cat cassette and the 650 bp derived from PmHAS. No wild-type amplicon is detected in the knockout strain reaction, therefore, homologous recombination mediated by a double crossover event occurred.

Furthermore, utilizing a sensitive radiochemical assay for HA polysaccharide, it was found that the mutant strain did not produce HA, and is shown in Table II which lists the HA production of various strains.

TABLE II

| Strain | HA polysaccharide (nanograms/ml per $OD_{600}$) |
|---|---|
| P = wild type parent | 1,200 |
| M = Mucoid transformant | 1,200 |
| KO = Acapsular knockout mutant | ≦0.05 |

The strains listed in Table II were overnight cultures of the various strains which were tested for the presence of HA polysaccharide using the specific radiometric assay outlined hereinabove. The cultures were normalized by spectrophotometry and the data was presented as the concentration of HA in a culture with an absorbance of 1.0 at 600 nm. The wild-type parent or a mucoid, encapsulated transformant synthesized substantial amounts of HA. In contrast, no detectable HA was produced by the acapsular knockout mutant (KO). Thus, the role of the capsule in virulence could be assessed. The methodology employed could also be used to construct other mutants of *P. multocida* and one of ordinary skill in the art, given the disclosure of the present invention, could accomplish such a task.

Animal testing has compared the in vivo pathogenicity of the mutants to complemented mutant controls and wild-type Type A *P. multocida*. The knockout strain of Type A *Pas-* teurella multocida ATCC 15742, (which causes fowl cholera), was shipped to the USDA Research Station in Ames, Iowa for virulence testing. Using targeted homologous recombination, capsule biosynthesis of the knockout strain has been disrupted and the knockout strain was predicted to be 1,000-fold less virulent.

The virulence testing was carried out to check the safety of the KO strain as a vaccine strain. Turkey eggs were hatched in clean conditions and raised to the age of two weeks. The poults were injected with various concentrations of bacteria (either wild-type parent or the knockout strain). The bacterial count was enumerated by spectroscopy and colony counting after plating. The animals were injected intramuscularly and placed in a biological containment pen. The inoculated poults (groups of 6 or 7 per microbial dose ranging from about 80 to $10^7$ bacteria in 10 fold steps)were observed. The general appearance, level of activity and morbidity was checked for 6 days. Dead or dying birds were autopsied and checked for the presence of lesions, abscesses, and organ failure.

The results of the in vivo experiments are summarized in Table III.

TABLE III

| Strain | No. of cells per injection | Mortality rate |
| --- | --- | --- |
| Wild-type wild type | $8 \times 10^3$ | 43% |
| Wild-type wild type | 860 | 17% |
| Mutant w/HAS knockout | $1 \times 10^7$ | 0% |

The point of this type of testing was to assess the general trends of infection with respect to encapsulation of the pathogen. For each determination, white turkeys were inoculated with a titered amount of bacteria IM. Symptoms and death of the turkeys was measured and tabulated in order to compare the relative virulence of the mutants. Protection trials will be conducted in order to determine if immunized turkeys can survive a challenge with wild-type virulent organisms.

Type A knockout strains that infect cattle and rabbits have also been prepared. Testing will be conducted in vivo in order to determine both the pathogenicity of these knockout strains as well as protection trials to determine if the immunized animals can survive a challenge with wild-type virulent organisms.

Two main types of protection experiments will be performed. First, passive immunization is done. One chicken is infected with the potential vaccine KO strain and a sample of its serum (with protective antibodies) is taken about 1-2 weeks after inoculation. This sera or derived purified antibody is injected into a naive chicken. The naive chicken is challenged with wild-type strain. The bird, if it receives protective antibody, will survive the challenge with the otherwise lethal wild-type bacteria.

Second, active immunization will be undertaken. In this case, the same chicken is sequentially infected with the potential vaccine KO strain, and a few weeks later, the bird is challenged with a normally lethal dose of wild-type bacteria. In this case antibody-mediated and cell mediated immunity are tested.

Using the present invention, it is predicted that there are similarities in the capsule loci of the various encapsulated types of P. multocida because of the close structural similarity of the polysaccharides. The present invention also relates to a homologous Type F P. multocida gene ("PmCS"). The PmCS sequence information is provided in SEQ ID NO:3. The Type F gene is approximately 85% identical to the Type A gene and the sequence comparison is shown in FIG. 20. This homology was found at the DNA level between the cloned type A capsule genes and certain regions of the Type D and F genomes by Southern blotting and PCR, as shown in FIGS. 15, 16, and 17. Libraries of Type F genomic DNA in lambda phage were screened to isolate the homologous capsule loci. Libraries of Type D genomic DNA in lambda phage will be screened to isolate the homologous capsule loci and one of ordinary skill in the art would appreciate and understand that the Type D capsule loci can be determined in exactly the same manner as with the Type A and F. The type A and F PmHAS sequences are 89% similar.

The Type F polysaccharide synthase gene was obtained by using a PCR product hybridization probe, FIG. 16, joining the HAS homolog and the Kfa homolog. A 3 kb amplicon was produced using genomic DNA from a Type F strain and the appropriate primers from a Kfa and synthase regions. This material was labeled with digoxigenin and used to obtain a clone and subsequently a plasmid from a Type F genomic DNA library in Lambda ZAP Express library (as described for the Type A cloning. The positively hybridizing clone was sequenced. As in the case of the Type A HA synthase gene, PmHAS, the functionality was checked by expression in the pKK223-3 (Pharmacia) vector in E. coli. It was found that this enzyme incorporated in vitro UDP-GalNAc and UDP-GlcA into high molecular weight polymer as expected for a chondroitin molecule.

The capsular polysaccharide synthases were monitored with antibodies and Western blot analysis. The antibodies were generated against a synthetic peptide that corresponds to a shared, homologous region (12-20 amino acid residues) of the synthase enzymes. Western blots confirmed that both Type A and Type F P. multocida had an immunoreactive 110 kDa protein by SDS-PAGE.

Figure 21:
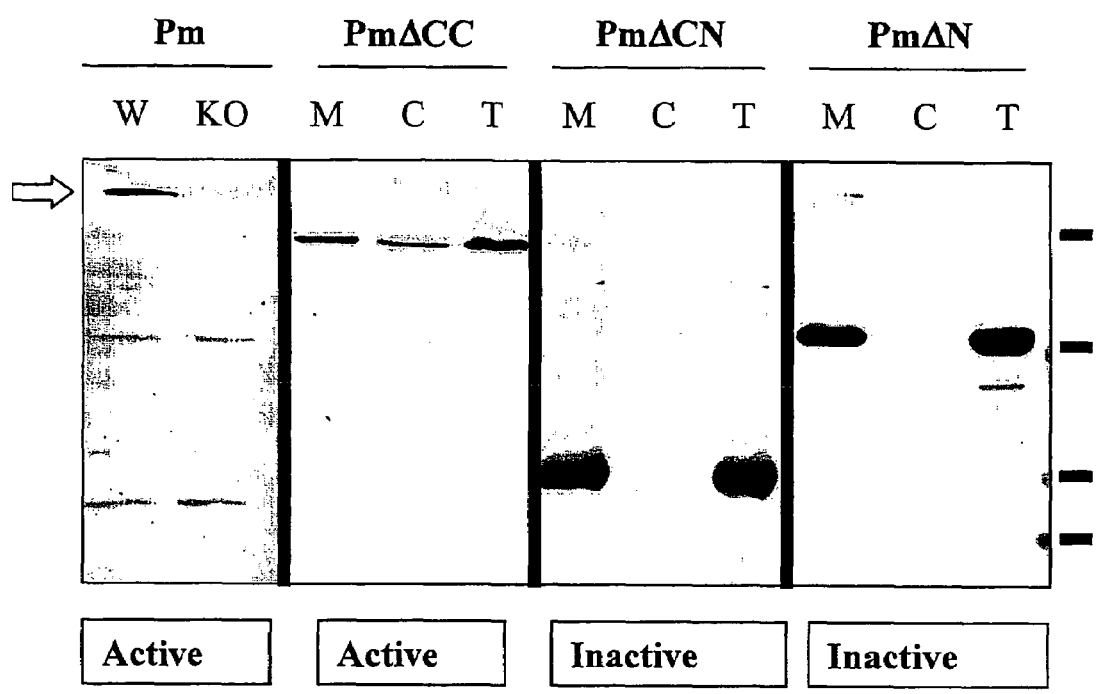
FIG. 21 is a Western blot anaylsis of native and recombinant PmHAS proteins.

FIG. 21 is a Western blot analysis of native and recombinant PmHAS proteins. The native PmHAS and various recombinant truncated PmHAS-derived proteins made in E. coli were compared on SDS-PAGE gels. For the recombinant samples, the total lysate (T), the membranes (M), and the cytoplasm (C) were subjected to Western blotting with an anti-PmHAS antibody. The original protein found in native Pasteurella multocida (Pm, lane W; marked with an arrow) migrates at about 110 kDa; the knockout vaccine strain (KO lane) is missing this band. The native PmHAS and a recombinant version missing a portion of the carboxyl terminus (PmΔCC) had HA synthase activity. The other truncated constructs were inactive.

4. Use of the PmHAS in Diagnostic Applications

The present invention also relates to the generation of useful probes that facilitate the identification of Type A, D, and F P. multocida or P. haemolytica in the field. The diagnosis of which particular strain is present in animals is currently determined by serology, agglutination, or DNA fingerprinting after restriction analysis. The former two methods can be problematic, frequently yield false identification, and vary depending on the source of typing antiserum. Capsular serology of the Carter Types A, D, and F does not even employ an antibody because these polymers are such poor immunogens. Instead, laborious assays involving enzymatic digestion or cell flocculation with acriflavine are routinely employed. DNA fingerprinting is accurate, but it relies on extensive knowledge of numerous type strains on file. Sets of capsule-specific primers will be used to readily perform these epidemiological studies, specifically by using rapid, facile PCR analysis to identify pathogenic isolates in half a day with minimal handling and no subculturing. Once the pathogen is identified, a more informed decision could be made on the choice of antibiotic or vaccine.

The utility of the use of capsule DNA information to quickly ascertain the type of *P. multocida* is obvious in light of the problems with current typing methods. Either hybridization or PCR-based typing is envisioned as practical, sensitive, and rapid. One specific embodiment would be to bring an appropriately labeled or tagged synthase DNA probe (or by extension a capsule locus gene which differs among capsule type) that by virtue of its uniqueness can be distinguished under appropriate hybridization conditions (e.g. complementary gene and probes hybridize to yield a signal while nonidentical gene from another capsular type does not hybridize thus no signal is obtained). Another specific embodiment would be to design PCR primers that can distinguish the capsule types. An amplicon of the correct size would signify a particular capsule type; no amplicon signifies another distinct capsule type.

In the current state of the art, several PCR primer pairs which give distinguishable and different size bands in a single reaction can be envisioned. Such a multiplex method would allow many reactions to be performed simultaneously. The knowledge of the DNA sequence of the various capsule biosynthesis loci, in particular the synthases, allows these tests to rapidly distinguish the various pathogenic strains.

Thus, it should be apparent that there has been provided in accordance with the present invention an isolated and sequenced PmHAS and a methods for making and using the PmHAS and knockout strains of *P. multocida* that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

I claim:

1. A purified and isolated nucleic acid sequence encoding enzymatically active hyaluronan synthase wherein the enzymatically active hyaluronan synthase is a single protein that polymerizes UDP-GlcA and UDP-GlcNAc to form hyaluronic acid, the nucleic acid sequence selected from the group consisting of:
   (a) the nucleic acid sequence as set forth in SEQ ID NO:2; and
   (b) a nucleic acid sequence encoding an enzymatically active hyaluronan synthase, wherein a complement of the nucleic acid sequence is capable of hybridizing to the nucleic acid sequence of SEQ ID NO:2 under standard hybridization conditions comprising 1.2-1.8× HPB at 40-50° C.

2. A procaryotic or eucaryotic host cell transformed or transfected with a nucleic acid segment according to claim 1 in a manner allowing the host cell to express hyaluronic acid.

3. An isolated and purified nucleic acid segment encoding enzymatically active hyaluronan synthase from *Pasteurella*, wherein the enzymatically active hyaluronan synthase is a single protein that polymerizes UDP-GlcA and UDP-GlcNAc to form hyaluronic acid, wherein a complement of the nucleic acid sequence is capable of hybridizing to the nucleic acid sequence of SEQ ID NO:2 under standard hybridization conditions comprising 1.2-1.8×HPB at 40-50° C.

4. A cDNA sequence according to claim 3.

5. A procaryotic or eucaryotic host cell transformed or transfected with a nucleic acid segment according to claim 3 in a manner allowing the host cell to express hyaluronic acid.

6. An isolated and purified nucleic acid segment encoding enzymatically active hyaluronan synthase from *Pasteurella*, wherein the enzymatically active hyaluronan synthase is a single protein that polymerizes UDP-GlcA and UDP-GlcNAc to form hyaluronic acid, wherein the nucleic acid segment is as set forth in SEQ ID NO:2.

7. A cDNA sequence according to claim 6.

8. A procaryotic or eucaryotic host cell transformed or transfected with a nucleic acid segment according to claim 6 in a manner allowing the host cell to express hyaluronic acid.

9. An isolated and purified nucleic acid segment encoding enzymatically active hyaluronan synthase from *Pasteurella*, wherein the enzymatically active hyaluronan synthase is a single protein that polymerizes UDP-GlcA and UDP-GlcNAc to form hyaluronic acid, and wherein the nucleic acid segment is at least 85% identical to SEQ ID NO:2.

10. A cDNA sequence according to claim 9.

11. A procaryotic or eucaryotic host cell transformed or transfected with a nucleic acid segment according to claim 9 in a manner allowing the host cell to express hyaluronic acid.

12. An isolated and purified nucleic acid segment encoding enzymatically active hyaluronan synthase from *Pasteurella*, wherein the enzymatically active hyaluronan synthase is a single protein that polymerizes UDP-GlcA and UDP-GlcNAc to form hyaluronic acid, wherein the hyaluronan synthase has SEQ ID NO:18 and at least two DSD motifs therein, and wherein a complement of the nucleic acid sequence is capable of hybridizing to the nucleic acid sequence of SEQ ID NO:2 under standard hybridization conditions comprising 1.2-1.8×HPB at 40-50° C.

13. A cDNA sequence according to claim 12.

14. A procaryotic or eucaryotic host cell transformed or transfected with a nucleic acid segment according to claim 12 in a manner allowing the host cell to express hyaluronic acid.

15. An isolated and purified nucleic acid segment encoding enzymatically active hyaluronan synthase from *Pasteurella*, wherein the enzymatically active hyaluronan synthase is a single protein that polymerizes UDP-GlcA and UDP-GlcNAc to form hyaluronic acid, and wherein the hyaluronate synthase encoded by the nucleic acid segment is at least 89% identical to SEQ ID NO:1.

16. A cDNA sequence according to claim 15.

17. A procaryotic or eucaryotic host cell transformed or transfected with a nucleic acid segment according to claim 15 in a manner allowing the host cell to express hyaluronic acid.

18. An isolated and purified nucleic acid segment encoding enzymatically active hyaluronan synthase, wherein the enzymatically active hyaluronan synthase is a single protein that polymerizes UDP-GlcA and UDP-GlcNAc to form hyaluronic acid, wherein the nucleic acid segment is as set forth in SEQ ID NO:17.

19. A cDNA sequence according to claim 18.

20. A procaryotic or eucaryotic host cell transformed or transfected with a nucleic acid segment according to claim 18 in a manner allowing the host cell to express hyaluronic acid.

* * * * *

UNITED STATES PATENT AND TRADEMARK OFFICE
CERTIFICATE OF CORRECTION

PATENT NO. : 7,232,684 B2 Page 1 of 1
APPLICATION NO. : 11/124215
DATED : June 19, 2007
INVENTOR(S) : Paul DeAngelis It is certified that error appears in the above-identified patent and that said Letters Patent is hereby corrected as shown below:

Column 5, line 53: Delete "20E" and replace with -- 20 --.

Column 7, line 45: Delete "Anoles" and replace with -- Angles --.

Column 20, line 44: Delete "*coil*" and replace with -- *coli* --.

Column 20, line 61: Delete "Sepharcyl" and replace with -- SEPHACRYL™ --.

Column 27, line 54: Delete "*coil*" and replace with -- *coli* --.

Signed and Sealed this

Eighth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,232,684 B2
APPLICATION NO. : 11/124215
DATED : June 19, 2007
INVENTOR(S) : Paul L. DeAngelis It is certified that error appears in the above-identified patent and that said Letters Patent is hereby corrected as shown below:

In the Specifications:

Column 1, lines 23-27: Delete entirety of paragraph and replace with -- This invention was made with government support under Contract Number MCB9876193 awarded by the National Science Foundation. The government has certain rights in the invention. --

Signed and Sealed this

Nineteenth Day of October, 2010

David J. Kappos
*Director of the United States Patent and Trademark Office*